(12) United States Patent
Bongartz et al.

(10) Patent No.: US 9,120,821 B2
(45) Date of Patent: Sep. 1, 2015

(54) PIPERIDINE/PIPERAZINE DERIVATIVES

(71) Applicant: Janssen Pharmaceutica NV, Beerse (BE)

(72) Inventors: Jean-Pierre Andre Marc Bongartz, Turnhout (BE); Lieven Meerpoel, Beerse (BE); Gustaaf Maria Boeckx, Oud-Turnhout (BE); Guy Rosalia Eugeen Van Lommen, Berlaar (BE); Christophe Francis Robert Nestor Buyck, Hamme (BE); Daniel Obrecht, Battwil (CH); Philipp Ermert, Allschwil (CH); Anatol Luther, Binzen (DE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 14/456,054

(22) Filed: Aug. 11, 2014

(65) Prior Publication Data

US 2014/0350012 A1  Nov. 27, 2014

Related U.S. Application Data

(62) Division of application No. 12/663,009, filed as application No. PCT/EP2008/056983 on Jun. 5, 2008, now Pat. No. 8,835,437.

(30) Foreign Application Priority Data

Jun. 8, 2007 (EP) .................................... 07109865

(51) Int. Cl.
| | |
|---|---|
| A61K 31/454 | (2006.01) |
| C07D 401/10 | (2006.01) |
| C07D 403/10 | (2006.01) |
| C07D 513/04 | (2006.01) |
| C07D 231/12 | (2006.01) |
| C07D 239/26 | (2006.01) |
| C07D 239/42 | (2006.01) |
| C07D 249/08 | (2006.01) |
| C07D 249/12 | (2006.01) |
| C07D 271/06 | (2006.01) |

(Continued)

(52) U.S. Cl.
CPC ............ *C07D 513/04* (2013.01); *C07D 231/12* (2013.01); *C07D 239/26* (2013.01); *C07D 239/42* (2013.01); *C07D 249/08* (2013.01); *C07D 249/12* (2013.01); *C07D 271/06* (2013.01); *C07D 271/107* (2013.01); *C07D 401/10* (2013.01); *C07D 487/04* (2013.01)

(58) Field of Classification Search
None
See application file for complete search history.

(56) References Cited

U.S. PATENT DOCUMENTS

| 4,698,352 A | 10/1987 | Narita et al. |
| 5,429,770 A | 7/1995 | Closs et al. |

(Continued)

FOREIGN PATENT DOCUMENTS

| CN | 1749256 A | 3/2006 |
| EP | 030371 A | 6/1981 |

(Continued)

OTHER PUBLICATIONS

International Search Report, International Application No. PCT/EP2008/056983, Date of Mailing of International Search Report, Nov. 6, 2008.

(Continued)

*Primary Examiner* — Emily Bernhardt

(57) ABSTRACT

The invention further relates to a DGAT inhibitor of formula (I)

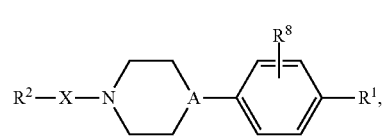

including any stereochemically isomeric form thereof, wherein A represents CH or N; X represents —$NR^x$—C(=O)—; —Z—C(=O)—; —Z—$NR^x$—C(=O)—; —S(=O)p-; —C(=S)—; —$NR^x$—C(=S)—; —Z—C(=S)—; —Z—$NR^x$—C(=S)—; —O—C(=O)—; —C(=O)—C(=O)—; $R^1$ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5- or 6-membered heterocycle; wherein each of said heterocycles may optionally be substituted; $R^2$ represents $R^3$; $R^3$ represents $C_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphtalenyl, 2,3-dihydro-1,4-benzo-dioxinyl, 1,3-benzodioxolyl, 2,3-dihydrobenzofuranyl or 6-membered aromatic heterocycle may optionally be substituted; a N-oxide thereof, a pharmaceutically acceptable salt thereof or a solvate thereof.

The invention further relates to methods for preparing such compounds, pharmaceutical compositions comprising said compounds as well as the use as a medicine of said compounds.

10 Claims, No Drawings

(51) Int. Cl.
*C07D 487/04* (2006.01)
*C07D 271/107* (2006.01)

(56) References Cited

U.S. PATENT DOCUMENTS

| | | | |
|---|---|---|---|
| 5,574,055 | A | 11/1996 | Borgulya et al. |
| 5,789,412 | A | 8/1998 | Halazy et al. |
| 6,492,368 | B1 | 12/2002 | Dorsch et al. |
| 6,884,868 | B1 | 4/2005 | Tojo Takashi et al. |
| 6,887,889 | B2 * | 5/2005 | Hobbs et al. ................. 514/331 |
| 7,186,683 | B2 | 3/2007 | Henriksen et al. |
| 2003/0055055 | A1 | 3/2003 | Teuber et al. |
| 2003/0060472 | A1 | 3/2003 | Learmonth et al. |
| 2004/0038858 | A1 | 2/2004 | Dorsch et al. |
| 2004/0162282 | A1 | 8/2004 | Pennell et al. |
| 2004/0220191 | A1 | 11/2004 | Schwink et al. |
| 2005/0059650 | A1 | 3/2005 | Jones et al. |
| 2005/0209241 | A1 | 9/2005 | Jolidon |
| 2006/0030612 | A1 | 2/2006 | Steffan |
| 2007/0021339 | A1 | 1/2007 | Alloza Miravete et al. |
| 2007/0207999 | A1 | 9/2007 | Stadtmueller et al. |
| 2007/0249620 | A1 | 10/2007 | Kutura et al. |

FOREIGN PATENT DOCUMENTS

| | | |
|---|---|---|
| EP | 0321131 A | 6/1989 |
| EP | 0378207 A | 7/1990 |
| EP | 0630954 A | 12/1994 |
| EP | 0657440 A | 6/1995 |
| EP | 1764360 A | 3/2007 |
| GB | 1383906 A | 2/1974 |
| JP | 11139969 | 5/1999 |
| JP | 2005-206492 A | 8/2005 |
| JP | 2005-330266 A | 12/2005 |
| JP | 2007-131584 A | 5/2007 |
| WO | WO 96/01820 A | 1/1996 |
| WO | WO 96/10822 A | 1/1996 |
| WO | WO 96/02525 A1 | 2/1996 |
| WO | WO 96/21648 A1 | 7/1996 |
| WO | WO 97/05877 A | 2/1997 |
| WO | WO 97/05878 A | 2/1997 |
| WO | WO 97/30995 A1 | 3/1997 |
| WO | WO 98/24766 A | 6/1998 |
| WO | WO 99/16751 A | 8/1999 |
| WO | WO 00/05225 A1 | 2/2000 |
| WO | WO 00/32582 | 6/2000 |
| WO | WO 00/71107 | 11/2000 |
| WO | WO 01/58885 A | 8/2001 |
| WO | WO 01/95856 A2 | 12/2001 |
| WO | WO 01/97810 | 12/2001 |
| WO | WO 01/97821 A1 | 12/2001 |
| WO | WO 02/20501 | 3/2002 |
| WO | WO 02/48117 A1 | 6/2002 |
| WO | WO 02/055012 A1 | 7/2002 |
| WO | WO 02/081460 | 10/2002 |
| WO | WO 03/064386 A | 8/2003 |
| WO | WO 03/076421 A1 | 9/2003 |
| WO | WO 03/076422 A1 | 9/2003 |
| WO | WO 03/082864 A | 10/2003 |
| WO | WO 03/087057 A1 | 10/2003 |
| WO | WO 2004/018439 A1 | 3/2004 |
| WO | WO 2004/047755 A2 | 6/2004 |
| WO | WO 2004/069792 A2 | 8/2004 |
| WO | WO 2004/072025 A | 8/2004 |
| WO | WO 2004/100881 A2 | 11/2004 |
| WO | WO 2004/110375 A | 12/2004 |
| WO | WO 2005/072740 A3 | 8/2005 |
| WO | WO 2006/004200 A1 | 1/2006 |
| WO | WO 2006/034441 A1 | 3/2006 |
| WO | WO 2006/038039 A | 4/2006 |
| WO | WO 2006/044775 A | 4/2006 |
| WO | WO 2006/047277 A1 | 5/2006 |
| WO | WO 2006/064189 A1 | 6/2006 |
| WO | WO 2006/067071 A1 | 6/2006 |
| WO | WO 2006/086445 A3 | 8/2006 |
| WO | WO 2006/094842 A | 9/2006 |
| WO | WO 2006/105127 A2 | 10/2006 |
| WO | WO 2006/106326 A | 10/2006 |
| WO | WO 2006/113919 A2 | 10/2006 |
| WO | WO 2006/113919 A3 | 10/2006 |
| WO | WO 2006/134317 A | 12/2006 |
| WO | WO 2007/071023 A1 | 6/2007 |
| WO | WO 2007/071966 A1 | 6/2007 |
| WO | WO 2007/096351 A1 | 8/2007 |
| WO | WO 2007/100990 A | 9/2007 |
| WO | WO 2008/003766 A2 | 1/2008 |
| WO | WO 2008/052638 A1 | 5/2008 |
| WO | WO 2008/122787 A1 | 10/2008 |
| WO | WO 2008/141976 A1 | 11/2008 |
| WO | WO 2008/148849 A2 | 12/2008 |
| WO | WO 2008/148851 A1 | 12/2008 |
| WO | WO 2008/148868 A1 | 12/2008 |
| WO | WO 2009/147170 A2 | 12/2009 |

OTHER PUBLICATIONS

International Preliminary Report on Patentability, relating to International Application No. PCT/EP2008/056983, Date of Completion of IPER, Sep. 14, 2009.
Extended EP Search Report relating to EP Application No. 07109865.1.
Aarmadaka et al., "Synthesis and Evaluation of Urea and Thiourea Derivatives of Oxazolidinones as Antibacterial Agents.", Chem. Pharm. Bull., Feb. 1, 2007, pp. 236-240, vol. 55.
Abstract RN854989-58-5, Jul. 13, 2005.
Abstract RN859099-41-5, Aug. 9, 2005.
Abstract RN859135-44-7, Aug. 9, 2005.
Abstract RN859646-88-1, Aug. 11, 2005.
Abstract RN860081-71-6, Aug. 12, 2005.
Abstract RN860458-98-6, Aug. 15, 2005.
Abstract RN861994-10-7, Aug. 29, 2005.
Abstract RN884476-57-7, May 16, 2006.
Abstract RN892188-37-3, Jul. 12, 2006.
Abstract RN892208-87-6, Jul. 12, 2006.
Abstract RN897172-00-8, Jul. 28, 2006.
Abstract RN897548-47-9, Jul. 31, 2006.
Abstract RN898117-91-4, Aug. 2, 2006.
Abstract RN898111-33-6, Aug. 2, 2006.
Birch et al., "DGAT1 inhibitors as anti-obesity and anti-diabetic agents", *Current Opinion in Drug Discovery & Development*, 2010, pp. 489-496, vol. 13(4).
Bose et al., "Glucagon-like Peptide 1 Can Directly Protect the Heart Against Ischemia/Reperfusion Injury.", Diabetes, Jan. 2005, vol. 54, pp. 146-151.
Buhman et al., "DGAT1 Is Not Essential for Intestinal Triacylglycerol Absorption or Chylomicron Synthesis.", J. Biol. Chem. Jul. 12, 2002, vol. 277(28), pp. 25474-25479.
Cao et al., "Targeting Acyl-CoA:Diacylglycerol Acyltransferase 1 (DGAT1) With Small Molecule Inhibitors for the Treatment of Metabolic Diseases.", J. Biol. Chem., 2011, pp. 41838-41851, vol. 286.
Cases et al., "Cloning of DGAT2, a Second Mammalian Diacylglycerol Acyltransferase, and Related Family Members.", J. Biol. Chem., Oct. 19, 2001, vol. 276(42), pp. 38870-38876.
Cases et al., "Identification of a gene encoding an acyl CoA:diacylglycerol acyltransferase, a key enzyme in triacylglycerol synthesis.", Proc. Natl. Acad. Sci., Oct. 1998, vol. 95, pp. 13018-13023.
Chen et al., "DGAT and Triglyceride Synthesis: A New Target for Obesity Treatment?", Trends Cardiovasc. Med., 2000, vol. 10(5), pp. 188-192.
Chen et al., "Enhancing energy and gluconse metabolism by disruption triglyceride synthesis; Lessons from mice lacking DGAT1.", Nutrition & Metabolism, Jan. 31, 2006; pp. 1-4, vol. 3(10).
Chen et al., "Increased insulin and leptin sensitivity in mice lacking acyl CoA:diacylglycerol acyltransferase 1.", J. Clin. Invest., 2002, vol. 109(8), pp. 1049-1055.
Chen et al., "Inhibition of Triglyceride Synthesis as a Treatment Strategy for Obesity. Lessons from DGAT1-Deficient Mice.", Arterioscler. Thromb. Vasc. Biol., 2005, pp. 482-486, vol. 25.
Database Registry, Apr. 17, 2007, XP002458843.

(56) References Cited

OTHER PUBLICATIONS

Database Registry, Aug. 3, 2005, XP002501332.
Database Registry, Aug. 5, 2005, XP002501333.
Database Registry, Aug. 8, 2005, XP002501334.
Database Registry, Aug. 8, 2005, XP002501335.
Database Registry, Mar. 22, 2004, XP002459101.
Database Registry, Mar. 22, 2004, XP002459102.
Database Registry, Mar. 22, 2004, XP002459103.
Database Registry, Nov. 3, 2004, XP002459099.
Farese et al., "Lipopenia and Skin Barrier Abnormalities in DGAT2-deficient Mice.", J. Biol. Chem., Mar. 19, 2004, pp. 11767-1176, vol. 279(12).
Farese et al., "Triglyceride synthesis: insights from the cloning of diacylglycerol acytransferase.", Curr. Opin. Lipidol. 2000, vol. 11, pp. 229-234.
Glass et al., "4-(4-Guanidinobenzoyl)-2-Imidazolones And Related Compounds: Phosphodiesterase Inhibitors and Novel Cardiotonics With Combined Histamine H2 Receptor Agonist and PDE III Inhibirot Activity.", Archiv. Der Pharmazie, 1995, vol. 328 (10), pp. 709-719, XP009002222.
Griffett et al., "Effects of 6-[p(4-phenylacetylpiperazine-1-yl)phenyl1]-4, 5-dihydro-3(2 H)pyridazinone (CCI 17810) and aspirin on platelet aggregation and adhesiveness.", Database, Medline, British J. of Pharmacology, Apr. 1981, vol. 72(4), pp. 697-705, XP002459094, (Abstract).
Guanming et al., "Synthesis and Platelet Aggregation Inhibitory Activity of Pyridazines.", Chinese J. Med. Chem., 1994, pp. 162-170, vol. 4.
Jiang et al., "Synthesis and platelet aggregation inhibitory activity of 6-(4-substituted phenyl)-4,5-dihydro-3(2H)-pyridazinones.", Database CA, Chemical Abstracts Service, XP002459098 (Abstract Only).
Khalaj et al., "Synthesis and antibacterial activity of 2-(4-substituted phenyl)-3(2H)-isothiazolones.", European Journal of Med. Chem., Aug. 2004, vol. 39(8), pp. 699-705, Paris, France, XP004523234.
Kuwabara et al., "A Nove Novel Selective Peroxisome Proliferator-Activated Receptor Agonist, 2-Methyl-c-5-[4-[5-methyl-2-(4-methylphenyl)-4-oxazolyl]butyl]-1,3-dioxane-r-2-carboxylic acid (NS-220),Potently Decreases Plasma Triglyceride and Glucose Levels and Modifies Lipoprotein Profiles in KK-Ay Mice.", J. Pharmacol. Exp. Ther., 2004, pp. 970-977, vol. 309(3).
Lee et al., "Inhibition of Diaclyglycerol Acyltransferase by Alkamides Isolated from the Fruits of Piper longum and Piper nigrum.", J. Agric. Food Chem., 2006, pp. 9759-9763, vol. 54.
Lewis et al., "Disordered fat storage and mobilization in the pathogenesis of insulin resistance and type 2 diabetes.", Endocrine Reviews, 2002, vol. 23(1), pp. 201-229.
Malloy and Kane, Pathogenesis and treatment in cardiomyopathy., Adv. Intern. Med., 2001, vol. 47, pp. 111-136.

Matsuda and Tomoda, "DGAT inhibitors for obesity", *Current Opinion in Investigational Drugs*, 2007, pp. 836-841, vol. 8(10).
Nikolaidis et al., "Glucagon-Like Peptide-1 Limits Myocardial Stunning following Brief Coronary Occlusion and Reperfusion in Conccious Canines.", Journal of Pharm. and Experimental Therapeutics, 2005, vol. 312(1), pp. 303-308.
Oelkers et al., "Characterizations of Two Human Genes Encoding Acyl Coenzyme A: Cholesterol Acyltransferase-related Enzymes.", J. Biol. Chem., Oct. 8, 1998, vol. 273(41), pp. 26765-26771, U.S.A.
Okawa et al., "Role of MGAT2 and DGAT1 in the release of gut peptides after triglyceride ingestion", *Biochemical and Biophysical Research Communications*, 2009, pp. 377-381, vol. 390.
Pearson et al., "Preparation of Functionalized P-Phenylenediamine Derivatives using Arene-Iron Chemistry.", J. of Org. Chem., 1996, vol. 61(4), pp. 1297-1305, Easton, US, XP002938137.
Perry et al., "Evidence of GLP-1-mediated neuroprotection in an animal model of pyridoxine-induced peripheral sensory neuropathy.", Experimental Neurology, 2007, vol. 203(2), pp. 293-301.
Phillipsh et al., "Structure-antibacterial activity of arylcarbonyl— and arylsulfonyl-piperazine 5-Triazolylmethyl oxazolidinones.", Eur.J.Med. Chem., Nov. 29, 2006, pp. 214-225, vol. 42.
Shandala et al., "Reactions of Acetylenic Esters with Cyclic Ketones and Substituted Acetophenones.", Journal f. prakt. Chemic. Band, 1979, pp. 899-904, vol. 321(6).
Smith et al., "Obesity resistance and multiple mechanisms of triglyceride synthesis in mice lacking Dgat.", Nature Genetics May 2000, vol. 25(1), pp. 87-90.
Stone et al., "Lipopenia and Skin Barrier Abnormalities in DGAT2-deficient Mice.", J. Biol. Chem., Mar. 19, 2004, vol. 279(12), pp. 11767-11776.
Vippangunta et al., "Crystalline Solids.", Advanced Drug Delivery Reviews, 2001, pp. 3-26, vol. 48.
Watt, M.J., "Storing Up Trouble: Does Accumulation of Intramyocellular Triglyceride Protect Skeletal Muscle from Insulin Resistance?", Clinical and Experimental Pharmacolgy and Physiology, 2009, pp. 5-11, vol. 36.
Wu, et al., "Synthesis and platelet agregation inhibitory activities of 6-[4(4-substituted-piperazine-1-yl)phenyl]-5-methyl-4,5-dihydro-3(2H)-pyridazinone derivatives.", Database CA, Chemical Abstracts Service, XP002459096.
Zhang et al., "Synthesis and platelet aggrregation inhibitory activity of pyridazinones.", Database CA, Chemical Abstracts Service, XP002459097.
Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095, (ABSTRACT).
Abstract RN892693-34-4, Jul. 16, 2006, (From STN Files).

* cited by examiner

PIPERIDINE/PIPERAZINE DERIVATIVES

CROSS REFERENCE TO RELATED APPLICATIONS

This application is a divisional of U.S. patent application Ser. No. 12/663,009, filed Dec. 4, 2009, which is the US national stage of Application No. PCT/EP2008/056983, filed Jun. 5, 2008, which application claims priority from EP 07109865.1, filed Jun. 8, 2007.

FIELD OF THE INVENTION

The present invention relates to the use of a DGAT inhibitor, in particular a DGAT1 inhibitor, for the manufacture of a medicament for the prevention or the treatment of a disease by elevating the levels of one or more satiety hormones, in particular GLP-1. The present invention also concerns piperidine/piperazine derivatives having DGAT inhibitory activity, in particular DGAT1 inhibitory activity. The invention further relates to methods for their preparation and pharmaceutical compositions comprising them. The invention also relates to the use of said compounds for the manufacture of a medicament for the prevention or the treatment of a disease mediated by DGAT, in particular DGAT 1.

BACKGROUND TO THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv. Intern. Med.* (2001) 47:11 1). Additionally, hypertriglyceridemia is often an adverse consequence of cancer therapy (see, Bast, et al. *Cancer Medicine*, 5th Ed., (2000) B.C. Decker, Hamilton, Ontario, CA).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol (DAG) and fatty acyl CoA to form triglycerides (TG) at the endoplasmic reticulum (reviewed in Chen and Farese, *Trends Cardiovasc. Med.* (2000) 10: 188 and Farese, et al, *Curr. Opin. Lipidol.* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 (human DGAT1) and ARGP2 (human ACAT2) now have been cloned and characterized (Cases, et al, *Pro.c Nat.l Acad. Sci.* (1998) 95:13018; Oelkers, et al, *J. Biol. Chem.* (1998) 273:26765). The gene for mouse DGAT1 has been used to create DGAT knock-out mice to better elucidate the function of the DGAT gene.

Unexpectedly, mice unable to express a functional DGAT1 enzyme (Dgat1−/− mice) are viable and still able to synthesize triglycerides, indicating that multiple catalytic mechanisms contribute to triglyceride synthesis (Smith, et al, *Nature Genetics* (2000) 25:87). Other enzymes that catalyze triglyceride synthesis, for example, DGAT2 and diacylglycerol transacylase, also have been identified (Cases, et al, *J. Biol. Chem.* (2001) 276:38870). Gene knockout studies in mice have revealed that DGAT2 plays a fundamental role in mammalian triglyceride synthesis and is required for survival. DGAT2 deficient mice are lipopenic and die soon after birth, apparently from profound reductions in substrates for energy metabolism and from impaired permeability barrier function in the skin. (Farese, et al., *J. Biol. Chem.* (2004) 279: 11767).

Significantly, Dgat1−/− mice are resistant to diet-induced obesity and remain lean. Even when fed a high fat diet (21% fat) Dgat1−/− mice maintain weights comparable to mice fed a regular diet (4% fat) and have lower total body triglyceride levels. The obesity resistance in Dgat1−/− mice is not due to decreased caloric intake, but the result of increased energy expenditure and decreased resistance to insulin and leptin (Smith, et al, *Nature Genetics* (2000) 25:87; Chen and Farese, *Trends Cardiovasc. Med.* (2000) 10: 188; and Chen, et al, *J. Clin. Invest.* (2002) 109:1049). Additionally, Dgat1−/− mice have reduced rates of triglyceride absorption (Buhman, et al, *J. Biol. Chem.* (2002) 277:25474). In addition to improved triglyceride metabolism, Dgat1−/− mice also have improved glucose metabolism, with lower glucose and insulin levels following a glucose load, in comparison to wild-type mice (Chen and Farese, *Trends Cardiovasc. Med.* (2000) 10: 188).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically inhibit the catalytic activity of DGAT, in particular DGAT1.

We have now unexpectedly found that the compounds of the present invention exhibit DGAT inhibitory activity, in particular DGAT1 inhibitory activity, and can therefore be used to prevent or treat a disease associated with or mediated by DGAT, such as for example obesity, type II diabetes, heart disease and cancer. The compounds of the invention differ from the prior art compounds in structure, in their pharmacological activity, pharmacological potency, and/or pharmacological profile.

We have also unexpectedly found that DGAT inhibitors can be used to elevate the levels of one or more satiety hormones, in particular glucagon-like-peptide-1 (GLP-1) and therefore DGAT inhibitors, in particular DGAT1 inhibitors, can also be used to prevent or treat a disease which can benefit from elevated levels of a satiety hormone, in particular GLP-1. Glucagon-like peptide 1 (GLP-1) is an intestinal hormone which generally stimulates insulin secretion during hyperglycemia, suppresses glucagon secretion, stimulates (pro) insulin biosynthesis and decelerates gastric emptying and acid secretion. GLP-1 is secreted from L cells in the small and large bowel following the ingestion of fat and proteins. GLP-1 has been suggested, among other indications, as a possible therapeutic agent for the management of type 2 non-insulin-dependent diabetes mellitus as well as related metabolic disorders, such as obesity.

Thus, by the present finding, a disease which can benefit from elevated levels of GLP-1 can be treated with small molecules (compared to large molecules such as proteins or protein-like compounds, e.g. GLP-1 analogues).

BACKGROUND PRIOR ART

WO 2006/034441 discloses heterocyclic derivatives and their use as stearoyl CoA desaturase inhibitors (SCD-1 inhibitors).

WO 2006/086445 relates to a combination therapy of a SCD-1 inhibitor and another drug to treat adverse weight gain.

WO 2006/004200 and JP2007131584 relate to urea and amino derivatives having DGAT inhibitory activity.

WO 2004/047755 relates to fused bicyclic nitrogen-containing heterocycles having DGAT inhibitory activity.

WO2005/072740 relates to an anorectic action of a compound having DGAT inhibitory activity.

DESCRIPTION OF THE INVENTION

The present invention relates to the use of a DGAT inhibitor for the manufacture of a medicament for the prevention or the treatment, in particular for the treatment, of a disease which can benefit from elevated levels of one or more satiety hormones, in particular GLP-1.

The present invention further relates to a compound of formula

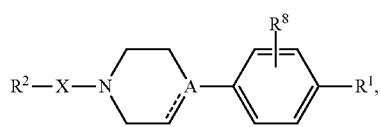

(I)

including any stereochemically isomeric form thereof, wherein

A represents CH or N;

the dotted line represents an optional bond in case A represents a carbon atom;

X represents —NR$^x$—C(=O)—; —Z—C(=O)—; —Z—NR$^x$—C(=O)—; —S(=O)p-; —C(=S)—; —NR$^x$—C(=S)—; —Z—C(=S)—; —Z—NR$^x$—C(=S)—; —O—C(=O)—; —C(=O)—C(=O)—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl or amino; and wherein two hydrogen atoms attached to the same carbon atom in $C_{1-6}$alkanediyl may optionally be replaced by $C_{1-6}$alkanediyl;

R$^x$ represents hydrogen or $C_{1-4}$alkyl;

R$^1$ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5- or 6-membered heterocycle; wherein each of said heterocycles may optionally be substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)-aminocarbonyl; $C_{1-6}$alkylcarbonyl; amino; mono- or di($C_{1-6}$alkyl)amino; R$^5$R$^4$N—$C_{1-6}$alkyl; $C_{3-6}$cycloalkyl-NR$^x$—; aryl-NR$^x$—; Het-NR$^x$—; $C_{3-6}$cycloalkyl-$C_{1-4}$alkyl-NR$^x$—; aryl$C_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; HetC$_{1-4}$alkyl; Het-C(=O)—; Het-C(=O)—$C_{1-4}$alkyl; Het-O—;

R$^2$ represents R$^3$;

R$^3$ represents $C_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphtalenyl, 2,3-dihydro-1,4-benzodioxinyl, 1,3-benzodioxolyl, 2,3-dihydrobenzofuranyl or 6-membered aromatic heterocycle may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; —S(=O)$_p$—$C_{1-4}$alkyl; R$^5$R$^4$N—C(=O)—; R$^5$R$^4$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; HetC$_{1-4}$alkyl; Het-C(=O)—$C_{1-4}$alkyl; Het-C(=O)—; Het-O—;

R$^4$ represents hydrogen; $C_{1-4}$alkyl optionally substituted with hydroxyl or $C_{1-4}$alkyloxy; R$^7$R$^6$N—$C_{1-4}$alkyl; $C_{1-4}$alkyloxy; Het; aryl; R$^7$R$^6$N—C(=O)—$C_{1-4}$alkyl;

R$^5$ represents hydrogen or $C_{1-4}$alkyl;

R$^6$ represents hydrogen; $C_{1-4}$alkyl; $C_{1-4}$alkylcarbonyl;

R$^7$ represents hydrogen or $C_{1-4}$alkyl; or

R$^6$ and R$^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

R$^8$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl p represents 1 or 2;

provided that the following compounds

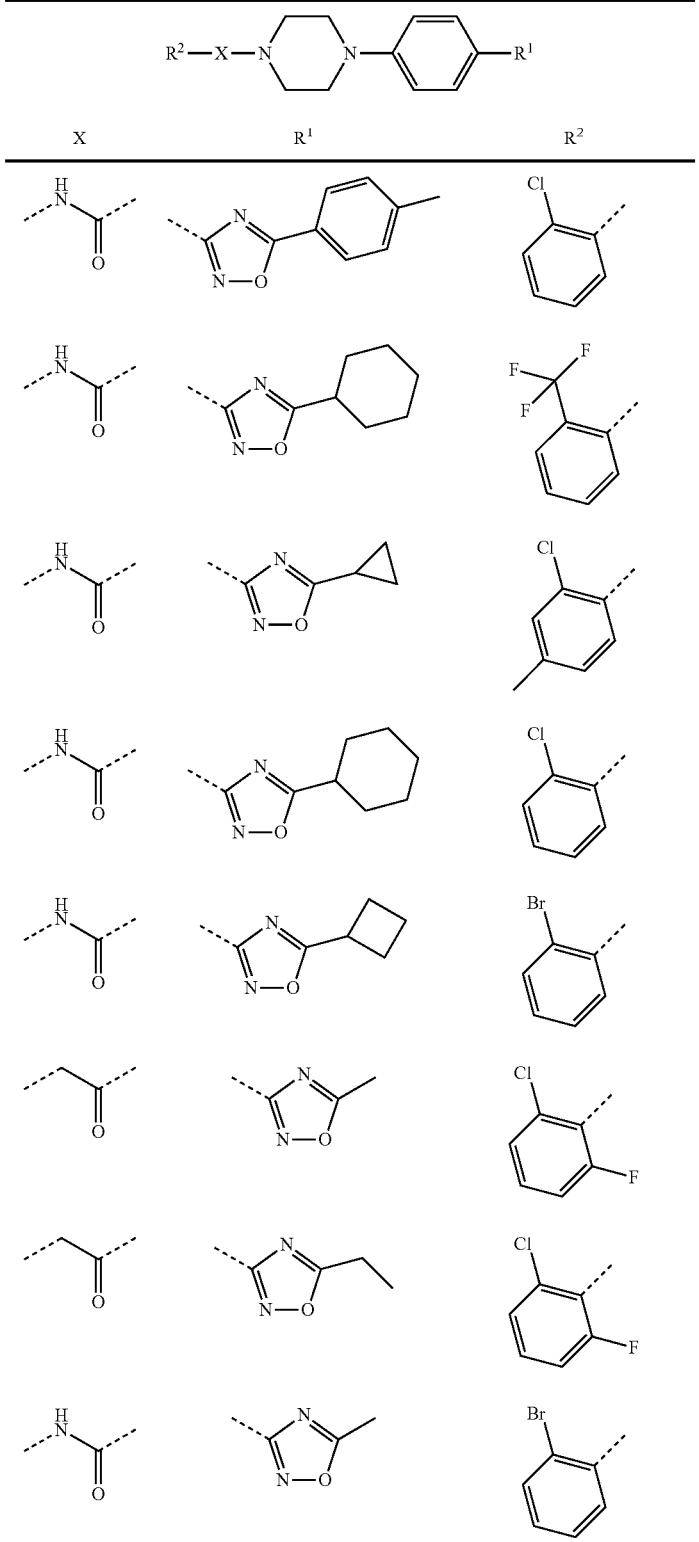

-continued
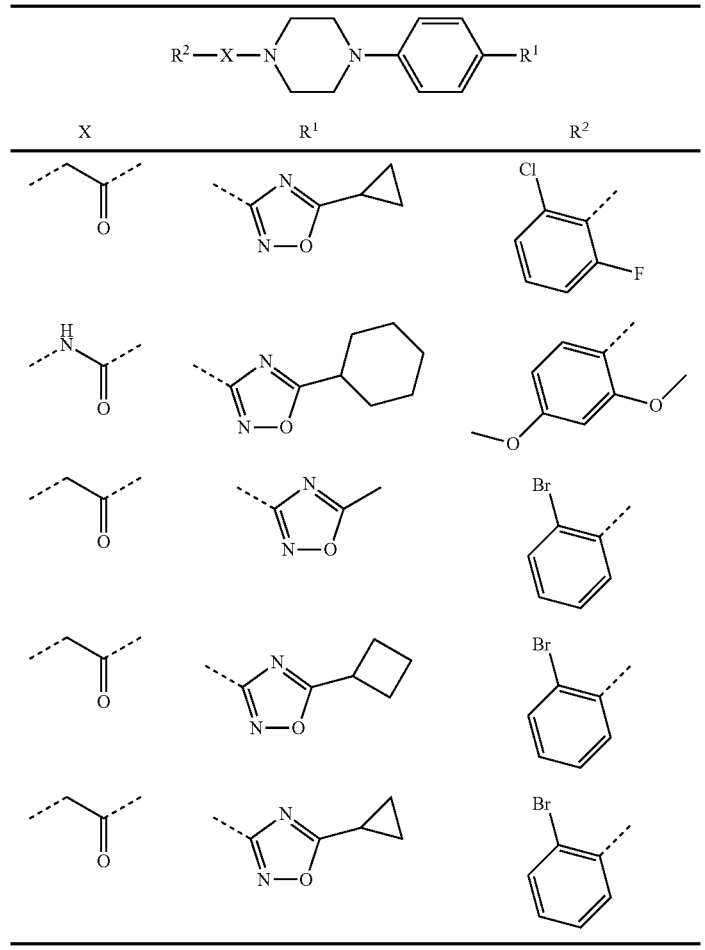
are excluded;
a N-oxide thereof, a pharmaceutically acceptable salt thereof or a solvate thereof.
The invention also relates to a compound of formula (I) as described above, provided that the following compounds
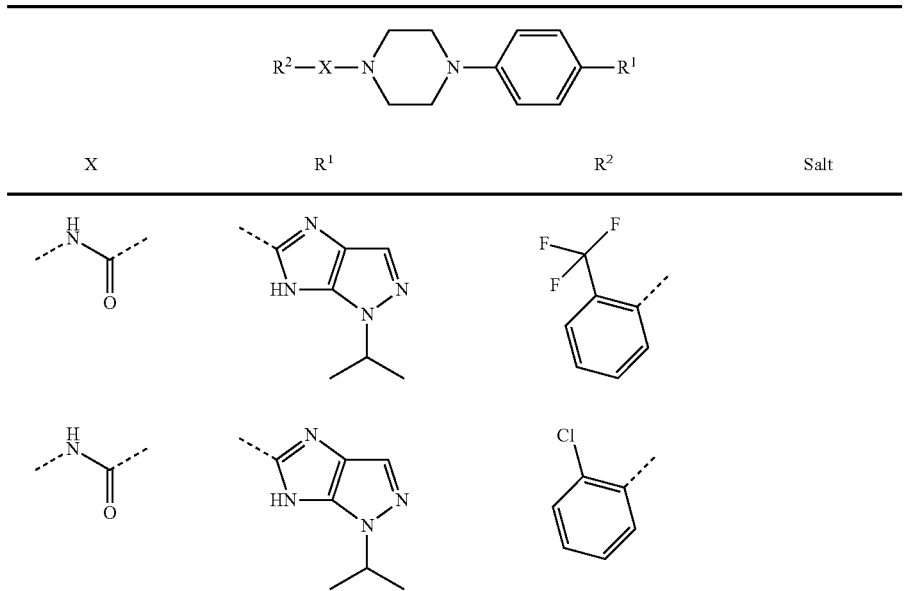

-continued

| X | R¹ | R² | Salt |
|---|----|----|------|

-continued
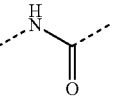
| X | R¹ | R² | Salt |
|---|----|----|------|
| 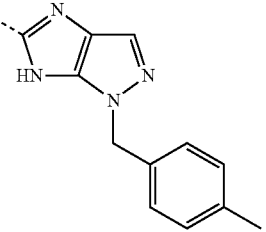 | 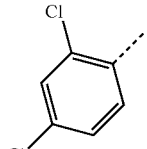 | 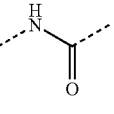 | |
| 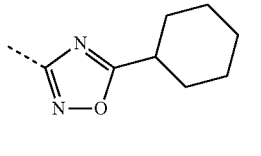 | 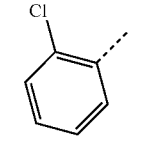 | 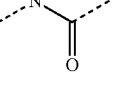 | |
| 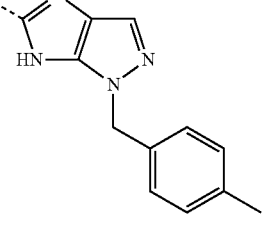 | 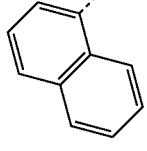 | 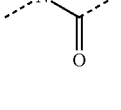 | |
| 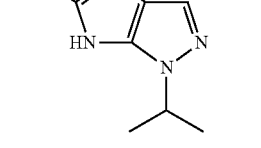 | 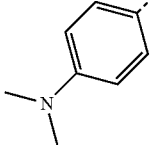 | 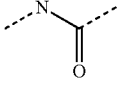 | |
| 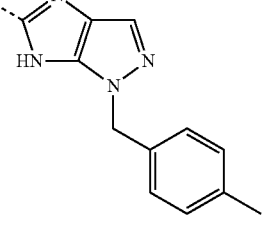 | 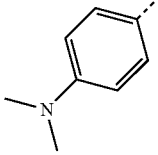 | 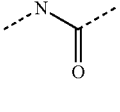 | |
| 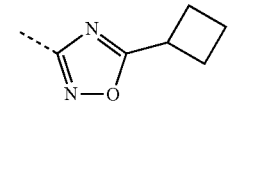 | 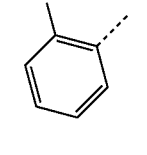 | 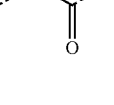 | |
| 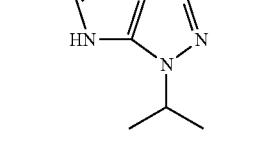 | 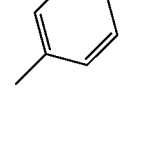 | | |

-continued

| X | R¹ | R² | Salt |
|---|---|---|---|
| —NH—C(=O)— | 5-(1-isopropyl-1H-imidazo[4,5-c]pyrazol-5-yl) | 4-methoxyphenyl | |
| —NH—C(=O)— | 5-(1-(4-methylbenzyl)-1H-imidazo[4,5-c]pyrazol-5-yl) | 2-methoxyphenyl | |
| —NH—C(=O)— | 5-(1-isopropyl-1H-imidazo[4,5-c]pyrazol-5-yl) | 2-methoxyphenyl | |
| —NH—C(=O)— | 5-(1-isopropyl-1H-imidazo[4,5-c]pyrazol-5-yl) | 3-methylphenyl | |
| —NH—C(=O)— | 5-(1-isopropyl-1H-imidazo[4,5-c]pyrazol-5-yl) | 4-(methylthio)phenyl | |
| —C(=O)— | 5-methyl-1,2,4-oxadiazol-3-yl | 2-chloro-6-fluorophenyl | |
| —NH—C(=O)— | 5-(1-isopropyl-1H-imidazo[4,5-c]pyrazol-5-yl) | naphthalen-2-yl | |
| —CH₂—NH—C(=O)— | 5-(1-isopropyl-1H-imidazo[4,5-c]pyrazol-5-yl) | phenyl | |

-continued

| X | R¹ | R² | Salt |
|---|----|----|------|
| -NH-C(=O)- | 5-(1-isopropyl-1H-pyrazolo[3,4-d]imidazol-5-yl) | 3-methoxyphenyl | |
| -NH-C(=O)- | 5-(1-isopropyl-1H-pyrazolo[3,4-d]imidazol-5-yl) | 3-morpholinophenyl | |
| -NH-C(=O)- | 5-(1-isopropyl-1H-pyrazolo[3,4-d]imidazol-5-yl) | benzo[d][1,3]dioxol-5-yl | |
| -C(=O)- | 5-ethyl-1,2,4-oxadiazol-3-yl | 2-chloro-6-fluorophenyl | |
| -NH-C(=O)- | 5-(1-(4-methylbenzyl)-1H-pyrazolo[3,4-d]imidazol-5-yl) | 4-methoxyphenyl | |
| -NH-C(=O)- | 5-(1-(4-methylbenzyl)-1H-pyrazolo[3,4-d]imidazol-5-yl) | phenyl | |
| -NH-C(=O)- | 5-(1-(4-methylbenzyl)-1H-pyrazolo[3,4-d]imidazol-5-yl) | cyclopropyl | |

-continued

| X | R¹ | R² | Salt |
|---|---|---|---|

-continued
| X | R¹ | R² | Salt |
|---|---|---|---|
| 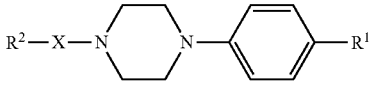 | 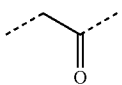 | 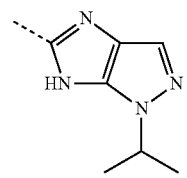 | |
| 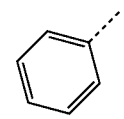 | 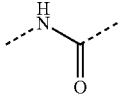 | 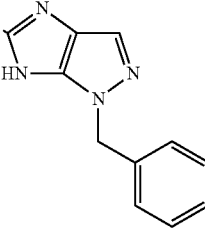 | |
| 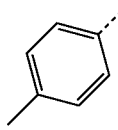 | 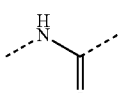 | 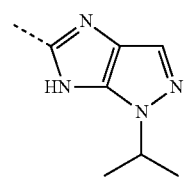 | |
| 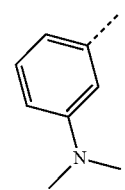 | 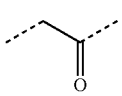 | 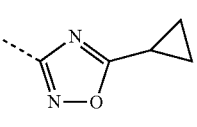 | |
| 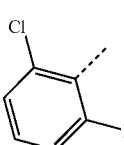 | 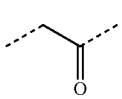 | 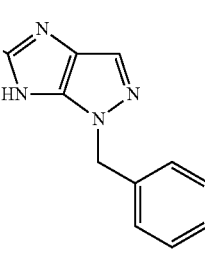 | |
| 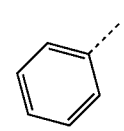 | 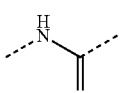 | 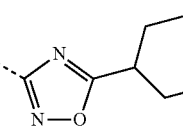 | |
| 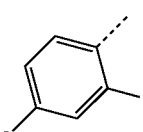 | 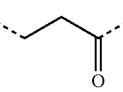 | 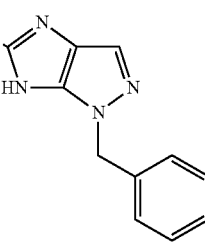 | |

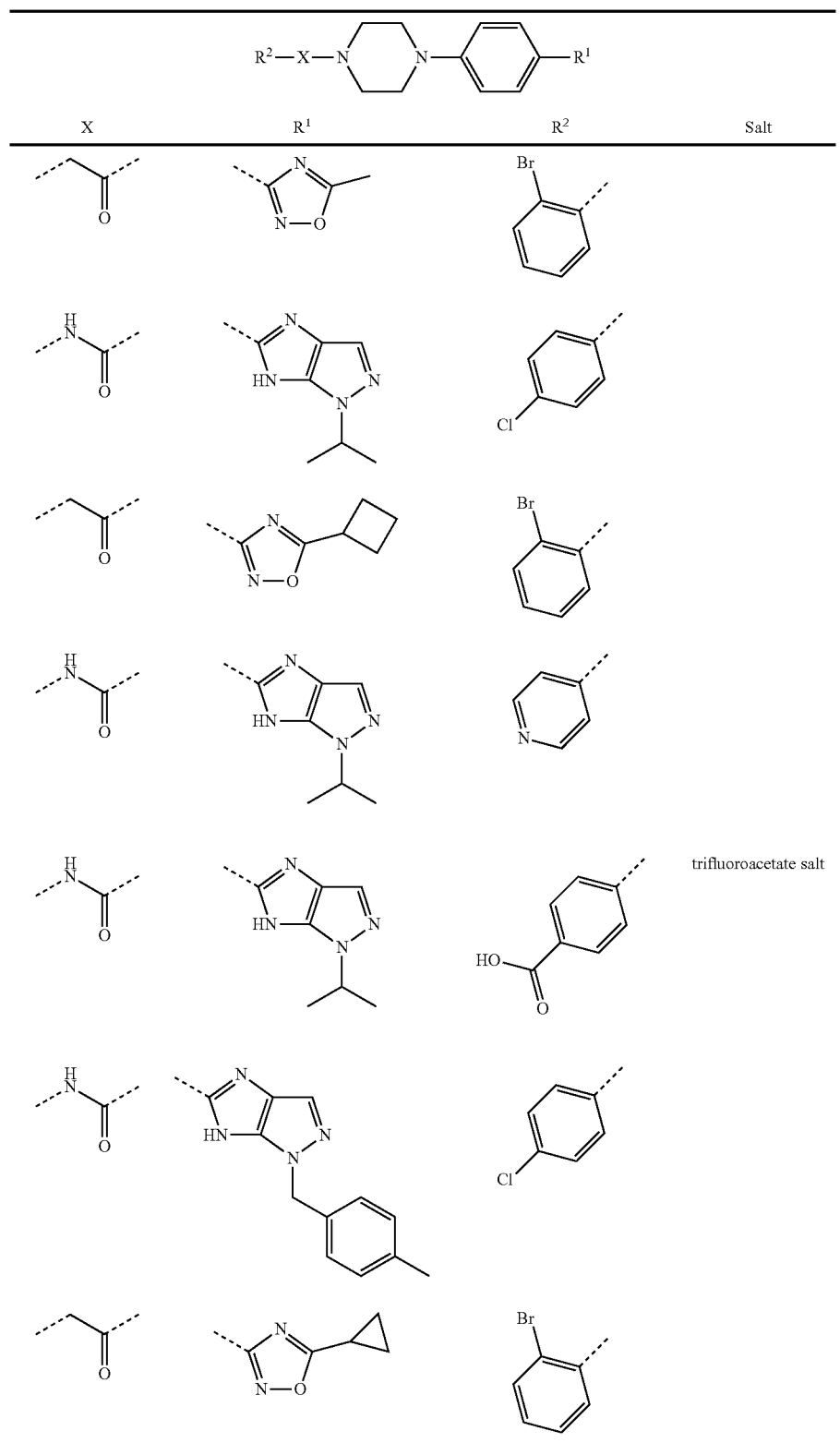

are excluded.

The present invention further relates to the use of a compound of formula (I''') for the manufacture of a medicament for the prevention or the treatment of a disease mediated by DGAT, in particular the present invention relates to the use of a compound of formula (I''') for the manufacture of a medicament for the prevention or the treatment of a disease which can benefit from inhibition of DGAT, in particular for the treatment of a disease which can benefit from inhibition of DGAT, in particular DGAT1, wherein the compound of formula (I''') is a compound of formula

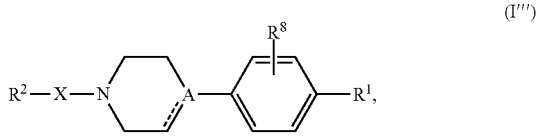

including any stereochemically isomeric form thereof, wherein
A represents CH or N;
the dotted line represents an optional bond in case A represents a carbon atom;
X represents —NR$^x$—C(=O)—; —Z—C(=O)—; —Z—NR$^x$—C(=O)—; —S(=O)p-; —C(=S)—; —NR$^x$—C(=S)—; —Z—C(=S)—; —Z—NR$^x$—C(=S)—; —O—C(=O)—; —C(=O)—C(=O)—;
Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl or amino; and wherein two hydrogen atoms attached to the same carbon atom in $C_{1-6}$alkanediyl may optionally be replaced by $C_{1-6}$alkanediyl;
R$^x$ represents hydrogen or $C_{1-4}$alkyl;
R$^1$ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5- or 6-membered heterocycle; wherein each of said heterocycles may optionally be substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)-aminocarbonyl; $C_{1-6}$alkylcarbonyl; amino; mono- or di($C_{1-6}$alkyl)amino; R$^5$R$^4$N—$C_{1-6}$alkyl; $C_{3-6}$cycloalkyl-NR$^x$—; aryl-NR$^x$—; Het-NR$^x$—; $C_{3-6}$cycloalkyl-$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—;
R$^2$ represents R$^3$;
R$^3$ represents $C_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphtalenyl, 2,3-dihydro-1,4-benzodioxinyl, 1,3-benzodioxolyl, 2,3-dihydrobenzofuranyl or 6-membered aromatic heterocycle may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; —S(=O)$_p$—$C_{1-4}$alkyl; R$^5$R$^4$N—C(=O)—; R$^5$R$^4$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—;
R$^4$ represents hydrogen; $C_{1-4}$alkyl optionally substituted with hydroxyl or $C_{1-4}$alkyloxy; R$^7$R$^6$N—$C_{1-4}$alkyl; $C_{1-4}$alkyloxy; Het; aryl; R$^7$R$^6$N—C(=O)—$C_{1-4}$alkyl;
R$^5$ represents hydrogen or $C_{1-4}$alkyl;
R$^6$ represents hydrogen; $C_{1-4}$alkyl; $C_{1-4}$alkylcarbonyl;
R$^7$ represents hydrogen or $C_{1-4}$alkyl; or
R$^6$ and R$^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;
R$^8$ represents hydrogen, halo, $C_{1-4}$alkyl, $C_{1-4}$alkyl substituted with hydroxyl;
aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;
Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three or four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl
p represents 1 or 2;
a N-oxide thereof, a pharmaceutically acceptable salt thereof or a solvate thereof.

The present invention also relates to the use of a compound of formula (I) or (I''') for the manufacture of a medicament for the prevention or the treatment of a disease which can benefit from elevated levels of one or more satiety hormones, in particular GLP-1, in particular the present invention relates to the use of a compound of formula (I) for the manufacture of a medicament for the treatment of a disease which can benefit from elevated levels of GLP-1.

The present invention further relates to the use of a compound of formula (I) for the manufacture of a medicament for the prevention or the treatment of a disease mediated by DGAT, in particular the present invention relates to the use of a compound of formula (I) for the manufacture of a medicament for the prevention or the treatment of a disease which can benefit from inhibition of DGAT, in particular for the treatment of a disease which can benefit from inhibition of DGAT, in particular DGAT1.

As used hereinbefore or hereinafter $C_{0-3}$alkyl as a group or part of a group defines straight or branched chain saturated hydrocarbon radicals having from 0 (then it represents a direct bond) to 3 carbon atoms such as methyl, ethyl, propyl, 1-methyl-ethyl; $C_{1-2}$alkyl as a group or part of a group defines straight or branched chain saturated hydrocarbon radicals having 1 or 2 carbon atoms such as methyl, ethyl; $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-5}$alkyl as a group or part of a group defines straight or branched chain saturated hydrocarbon radicals having from 1 to 5 carbon atoms such as the group defined for $C_{1-4}$alkyl and pentyl, 2-methylbutyl and the like; $C_{1-6}$alkyl as a group or part of a group defines straight or branched chain saturated hydrocarbon radicals having from 1 to 6 carbon atoms such as the group defined for $C_{1-4}$alkyl and for $C_{1-5}$alkyl and hexyl, 2-methylpentyl and the like; $C_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl and the like; $C_{2-6}$alkenyl as a group or part of a group defines straight or branched chain hydrocarbon radicals having from 2 to 6 carbon atoms and having a double bond such as ethenyl, propenyl, butenyl, pentenyl, hexenyl, 3-methylbutenyl and the like; $C_{2-6}$alkenediyl defines straight or branched chain bivalent hydrocarbon radicals having from 2 to 6 carbon atoms and having a double bond such as 1,2-ethenediyl, 1,3-propenediyl, 1,4-butenediyl, 1,5-pentenediyl and the like; $C_{2-6}$alkynediyl as a group or part of a group defines straight or branched chain bivalent hydrocarbon radicals having from 2 to 6 carbon atoms and having a triple bond such as 1,2-ethynediyl, 1,3-propynediyl, 1,4-butynediyl, 1,5-pentynediyl and the like;

$C_{3-6}$cycloalkyl is generic to cyclopropyl, cyclobutyl, cyclopentyl and cyclohexyl.

The term halo is generic to fluoro, chloro, bromo and iodo. As used hereinbefore or hereinafter, polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoro-ethyl and the like. In case more than one halogen atoms are attached to a $C_{1-6}$alkyl group within the definition of polyhalo$C_{1-6}$alkyl, they may be the same or different.

As used herein before, the term (=O) forms a carbonyl moiety when attached to a carbon atom, a sulfoxide moiety when attached to a sulfur atom and a sulfonyl moiety when two of said terms are attached to a sulfur atom. Oxo means =O.

The radical $R^1$ as defined hereinabove may be an optionally substituted 5-membered monocyclic heterocycle containing at least 2 heteroatoms, an optionally substituted 6-membered aromatic monocyclic heterocycle or an optionally substituted 5-membered heterocycle containing at least 2 heteroatoms fused with a phenyl, cyclohexyl or a 5- or 6-membered heterocycle.

A 5-membered monocyclic heterocycle as defined hereinabove or hereinafter may be a 5-membered monocyclic non-aromatic (fully saturated or partially saturated) or aromatic heterocycle containing at least 2 heteroatom, in particular 2 or 3 heteroatoms, each independently selected from O, S, $S(=O)_p$ or N. Examples of such unsubstituted monocyclic 5-membered heterocycles comprise, but are not limited to, non-aromatic (fully saturated or partially saturated) or aromatic 5-membered monocyclic heterocycles such as for example 1,3-dioxolanyl, imidazolidinyl, thiazolidinyl, dihydrooxazolyl, isothiazolidinyl, isoxazolidinyl, oxadiazolidinyl, triazolidinyl, thiadiazolidinyl, pyrazolidinyl, imidazolinyl, pyrazolinyl, imidazolyl, oxazolyl, isoxazolyl, thiazolyl, isothiazolyl, pyrazolyl, triazolyl, thiadiazolyl, oxadiazolyl, tetrazolyl and the like. Optional substituents of the above heterocycles are hydroxyl; oxo; carboxyl; halo; $C_{1-6}$alkyl optionally substituted with carboxyl, $C_{1-4}$alkyloxy-carbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)-aminocarbonyl; $C_{1-6}$alkylcarbonyl; amino; mono- or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —$S(=O)_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

A 6-membered aromatic monocyclic heterocycle as defined hereinabove or hereinafter contains at least one heteroatom, in particular 1, 2 or 3 heteroatoms, each independently selected from O, S, $S(=O)_p$ or N. Examples of such unsubstituted monocyclic 6-membered aromatic heterocycles comprise, but are not limited to, pyridyl, pyrimidinyl, pyrazinyl, pyridazinyl, triazinyl, pyranyl and the like. Optional substituents of the above heterocycles are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; amino; mono- or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —$S(=O)_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

A 5-membered heterocycle containing at least 2 heteroatoms fused with phenyl, cyclohexyl or a 5- or 6-membered heterocycle as defined hereinabove or hereinafter may be a non-aromatic (fully saturated or partially saturated) or aromatic 5-membered heterocycle containing at least 2 heteroatoms, in particular 2 or 3 heteroatoms, each independently selected from O, S, $S(=O)_p$ or N, in particular O, S or N, more in particular O or N, fused with phenyl, cyclohexyl or a 5- or 6-membered non-aromatic (fully saturated or partially saturated) or aromatic heterocycle containing at least one heteroatom, in particular 1, 2 or 3 heteroatoms, each independently selected from O, S, $S(=O)_p$ or N. Examples of such unsubstituted bicyclic heterocycles comprise, but are not limited to, non-aromatic (fully saturated or partially saturated) or aromatic 8- or 9-membered bicyclic heterocycles such as for example 1,3-benzodioxolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyridinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl and the like. Optional substituents of the above heterocycles are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-6}$alkyl)aminocarbonyl; $C_{1-6}$alkylcarbonyl; amino; mono- or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

The radical Het as defined hereinabove may be an optionally substituted monocyclic non-aromatic or aromatic heterocycle containing at least one heteroatom selected from O, S, S(=O)$_p$ or N; or a optionally substituted bi- or tricyclic non-aromatic or aromatic heterocycle containing at least one heteroatom selected from O, S, S(=O)$_p$ or N. Examples of such unsubstituted monocyclic heterocycles comprise, but are not limited to, non-aromatic (fully saturated or partially saturated) or aromatic 4-, 5-, 6- or 7-membered monocyclic heterocycles such as for example azetidinyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, pyrrolinyl, imidazolinyl, pyrazolinyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl and the like. Examples of such unsubstituted bicyclic or tricyclic heterocycles comprise, but are not limited to, non-aromatic (fully saturated or partially saturated) or aromatic 8- to 17-membered bicyclic or tricyclic heterocycles such as for example decahydroquinolinyl, octahydroindolyl, 2,3-dihydrobenzofuranyl, 1,3-benzodioxolyl, 2,3-dihydro-1,4-benzodioxinyl, indolinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl; isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like. Optional substituents of the above heterocycles are hydroxyl; oxo; carboxyl; halo; $C_{1-6}$alkyl optionally substituted with $C_{1-4}$alkyloxy, amino or mono- or di-($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl.

Examples of a 6-membered aromatic heterocycle containing 1 or 2 N atoms in the definition of $R^3$ are pyridyl, pyrimidinyl, pyridazinyl, pyrazinyl.

When any variable occurs more than one time in any constituent (e.g. aryl, Het), each definition is independent.

The term Het or $R^1$ is meant to include all the possible isomeric forms of the heterocycles, for instance, pyrrolyl comprises 1H-pyrrolyl and 2H-pyrrolyl.

The carbocycles or heterocycles covered by the terms aryl, Het, $R^1$ or $R^3$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

Lines drawn from substituents into ring systems indicate that the bond may be attached to any of the suitable ring atoms.

When X is defined as for instance —$NR^x$—C(=O)—, this means that the nitrogen of $NR^x$ is linked to the $R^2$ substituent and the carbon atom of C(=O) is linked to the nitrogen of the ring

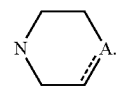

Thus the left part of the bivalent radical in the definition of X is linked to the $R^2$ substituent and the right part of the bivalent radical in the definition of X is linked to the ring moiety

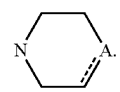

Some of the compounds of formula (I) may also exist in their tautomeric form. Such forms although not explicitly indicated in the above formula are intended to be included within the scope of the present invention.

Whenever used hereinbefore or hereinafter that substituents can be selected each independently out of a list of numerous definitions, such as for example for $R^4$ and $R^5$, all possible combinations are intended which are chemically possible.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted $C_{1-6}$alkylhalide, arylhalide, $C_{1-6}$alkyl-carbonylhalide, arylcarbonylhalide, or aryl$C_{1-6}$alkylhalide, e.g. methyliodide or benzyliodide. Other reactants with good leaving groups may also be used, such as for example $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

The term solvate comprises the hydrates and solvent addition forms which the compounds of formula (I) are able to form, as well as salts thereof. Examples of such forms are e.g. hydrates, alcoholates and the like.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, salts, and solvates may contain one or more centers of chirality and exist as stereochemically isomeric forms.

The term "stereochemically isomeric forms" as used hereinbefore or hereinafter defines all the possible stereoisomeric forms which the compounds of formula (I), and their N-oxides, salts, or solvates may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts or solvates, substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Whenever used hereinafter, the term "compounds of formula (I)" or any subgroup thereof, is meant to also include their N-oxide forms, their salts, their stereochemically isomeric forms and their solvates. Of special interest are those compounds of formula (I) which are stereochemically pure.

A first embodiment of the present invention are those compounds of formula (I) having the following formula

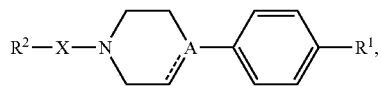

(I)

including any stereochemically isomeric form thereof, wherein

A represents CH or N;

the dotted line represents an optional bond in case A represents a carbon atom;

X represents —NR$^x$—C(=O)—; —Z—C(=O)—; —Z—NR$^x$—C(=O)—; —S(=O)p-; —C(=S)—; —NR$^x$—C(=S)—; —Z—C(=S)—; —Z—NR$^x$—C(=S)—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl;

R$^x$ represents hydrogen or $C_{1-4}$alkyl;

R$^1$ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5- or 6-membered heterocycle; wherein each of said heterocycles may optionally be substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

R$^2$ represents R$^3$;

R$^3$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxy-carbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; R$^5$R$^4$N—C(=O)—; R$^5$R$^4$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

R$^4$ represents hydrogen; $C_{1-4}$alkyl optionally substituted with hydroxyl or $C_{1-4}$alkyloxy; R$^7$R$^6$N—$C_{1-4}$alkyl; $C_{1-4}$alkyloxy; Het; aryl; R$^7$R$^6$N—C(=O)—$C_{1-4}$alkyl;

R$^5$ represents hydrogen or $C_{1-4}$alkyl;

R$^6$ represents hydrogen; $C_{1-4}$alkyl; $C_{1-4}$alkylcarbonyl;

R$^7$ represents hydrogen or $C_{1-4}$alkyl; or

R$^6$ and R$^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

p represents 1 or 2;

provided that the following compounds
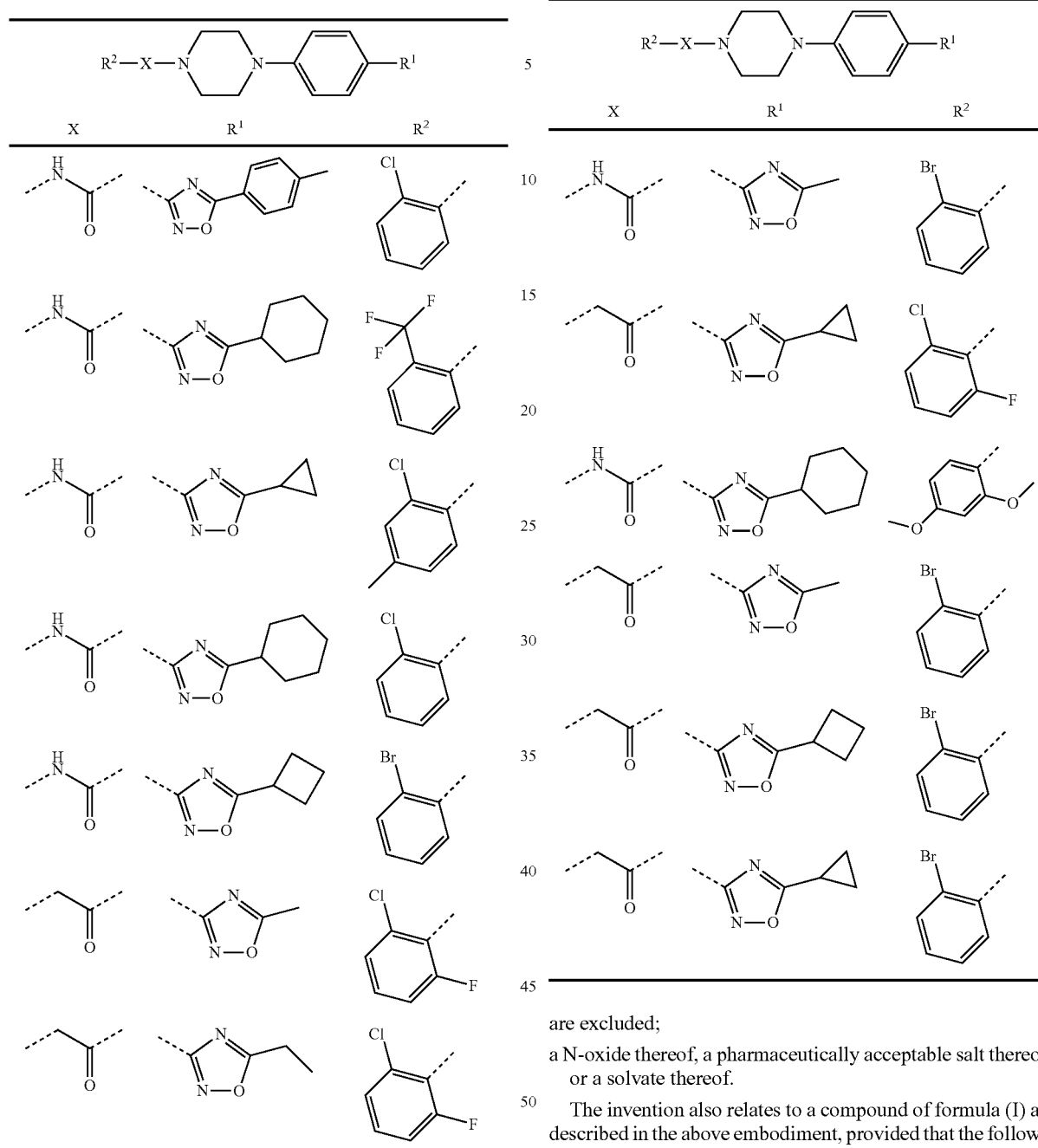
are excluded;
a N-oxide thereof, a pharmaceutically acceptable salt thereof or a solvate thereof.
The invention also relates to a compound of formula (I) as described in the above embodiment, provided that the following compounds
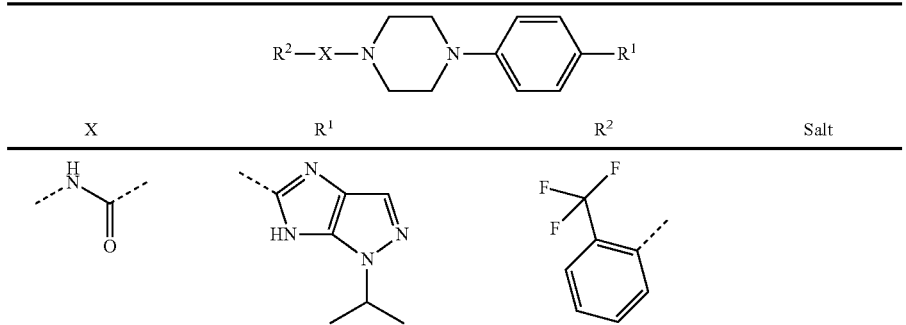

-continued
| X | R¹ | R² | Salt |
|---|---|---|---|
| 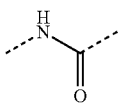 | 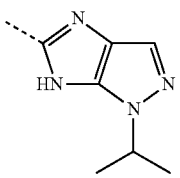 | 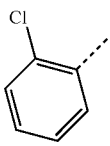 | |
| 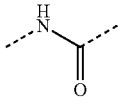 | 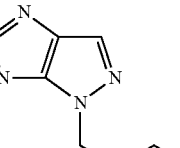 | 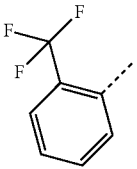 | |
| 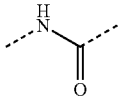 | 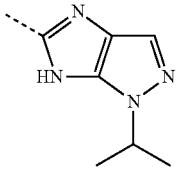 | 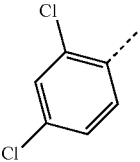 | |
| 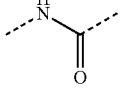 | 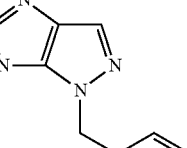 | 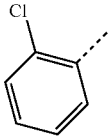 | |
| 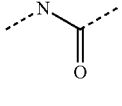 | 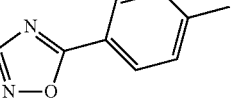 | 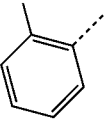 | |
| 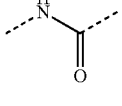 | 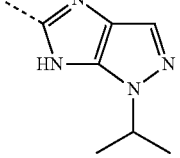 | 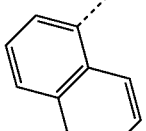 | |
| 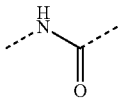 | 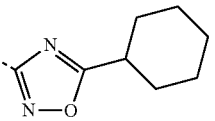 | 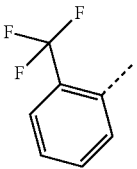 | |

-continued

| X | R¹ | R² | Salt |
|---|----|----|------|
| -NH-C(=O)- | 5-cyclopropyl-1,2,4-oxadiazol-3-yl | 2-chloro-4-methylphenyl | |
| -NH-C(=O)- | 5-(4-methylbenzyl)-1,5-dihydroimidazo[4,5-c]pyrazol-2-yl | 2,4-dichlorophenyl | |
| -NH-C(=O)- | 5-cyclohexyl-1,2,4-oxadiazol-3-yl | 2-chlorophenyl | |
| -NH-C(=O)- | 5-(4-methylbenzyl)-1,5-dihydroimidazo[4,5-c]pyrazol-2-yl | 1-naphthyl | |
| -NH-C(=O)- | 5-isopropyl-1,5-dihydroimidazo[4,5-c]pyrazol-2-yl | 4-(dimethylamino)phenyl | |
| -NH-C(=O)- | 5-(4-methylbenzyl)-1,5-dihydroimidazo[4,5-c]pyrazol-2-yl | 4-(dimethylamino)phenyl | |
| -NH-C(=O)- | 5-cyclobutyl-1,2,4-oxadiazol-3-yl | 2-bromophenyl | |

-continued
| X | R¹ | R² | Salt |
|---|----|----|------|
| 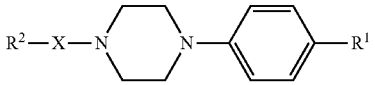 | 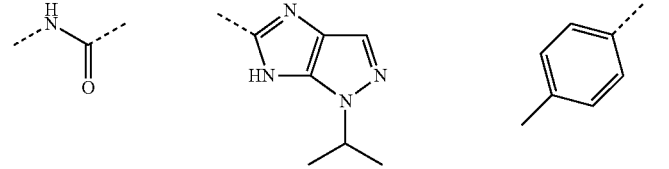 | 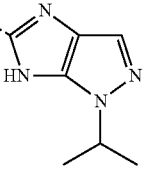 | |
| 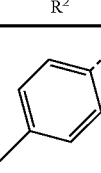 | 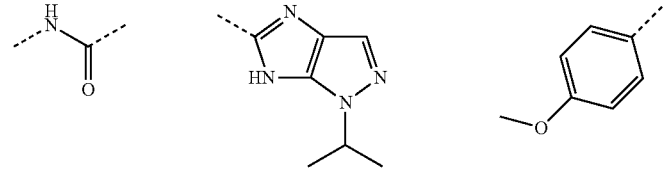 | 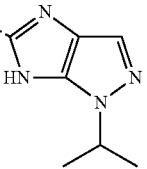 | |
| 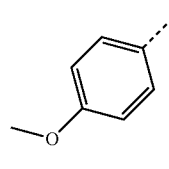 | 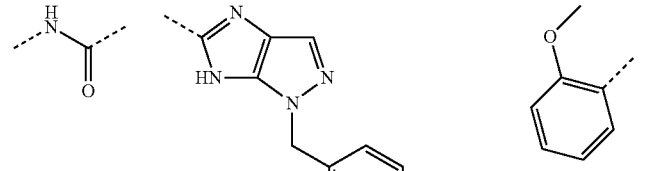 | 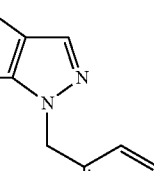 | |
| 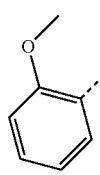 | 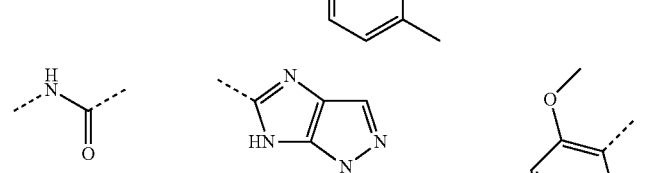 | 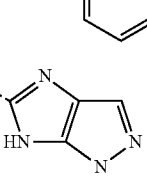 | |
| 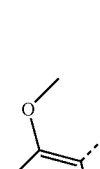 | 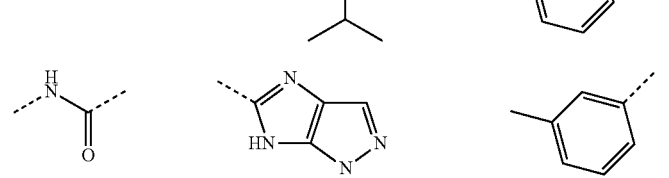 | 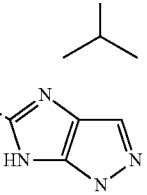 | |
| 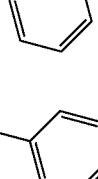 | 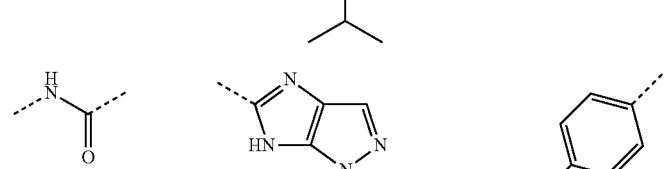 | 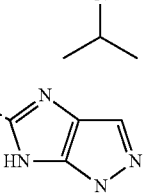 | |
| 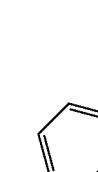 | 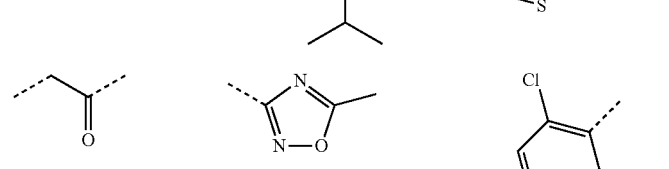 | 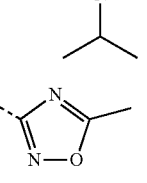 | |
| 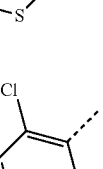 | 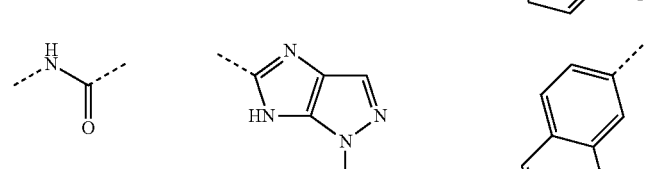 | 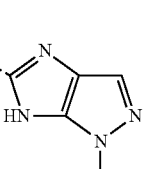 | |

-continued

| X | R¹ | R² | Salt |
|---|----|----|------|

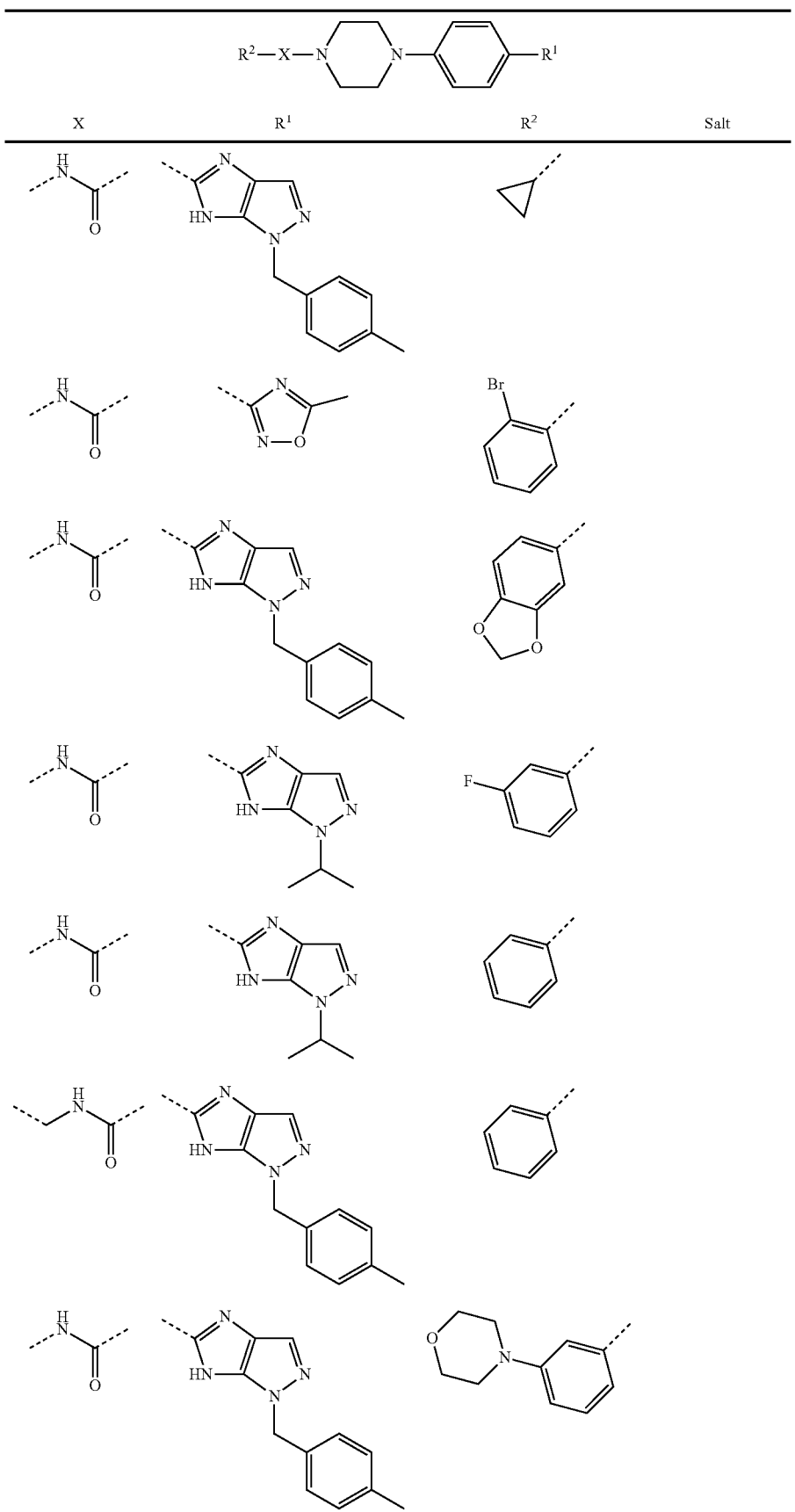

-continued

| X | R¹ | R² | Salt |
|---|----|----|------|

(table of structural entries; structures shown as chemical drawings)

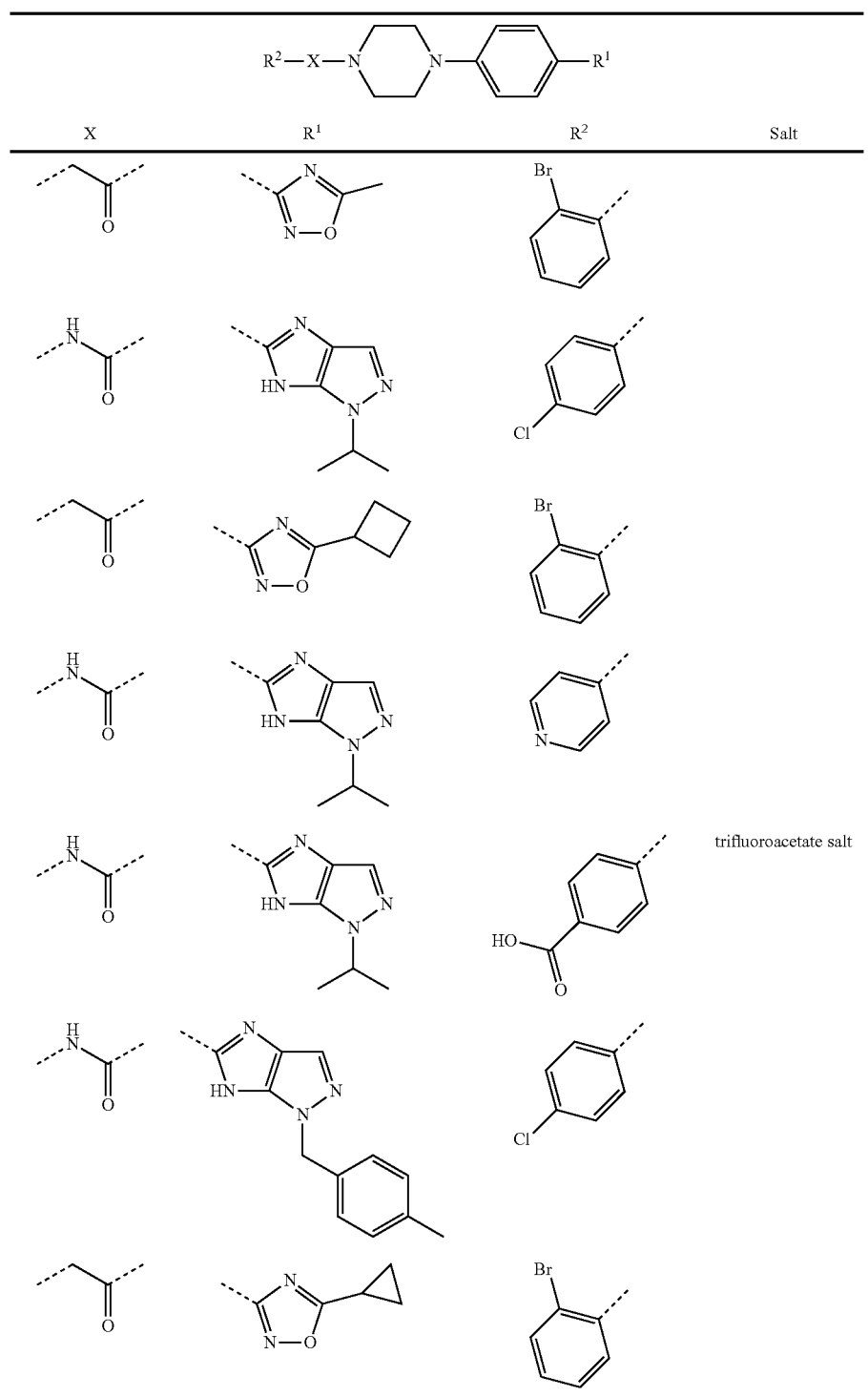

are excluded.

A second embodiment of the present invention are those compounds of formula (I) or, whenever possible, any subgroup thereof as mentioned hereinbefore as embodiment wherein X represents —NR$^x$—C(=O)—; —Z—C(=O)—; —Z—NR$^x$—C(=O)—; —S(=O)p-; —NR$^x$—C(=S)— or —O—C(=O)—; in particular X represents —NR$^x$—C(=O)—; —Z—C(=O)—; —Z—NR$^x$—C(=O)—; more in particular X represents —NR$^x$—C(=O)— or —Z—C(=O)—.

A third embodiment of the present invention are those compounds of formula (I) or, whenever possible, any subgroup thereof as mentioned hereinbefore as embodiment wherein A represents N.

A fourth embodiment of the present invention are those compounds of formula (I) or, whenever possible, any subgroup thereof as mentioned hereinbefore as embodiment wherein A represents CH, in particular wherein A represents CH and the dotted line does not represent a bond.

A fifth embodiment of the present invention are those compounds of formula (I) or, whenever possible, any subgroup thereof as mentioned hereinbefore as embodiment wherein $R^1$ represents a 5-membered monocyclic heterocycle containing at least 2 heteroatoms, in particular pyrazolyl, triazolyl or oxadiazolyl; a 6-membered monocyclic aromatic heterocycle, in particular pyrimidinyl; or a 5-membered aromatic heterocycle containing at least 2 heteroatoms fused with a 5-membered heterocycle, in particular imidazopyrazolyl or imidazothiazolyl; wherein each of said heterocycles may optionally be substituted, preferably with one or two substituents. Particular substituents of said heterocycles include oxo, $C_{1-6}$alkyl optionally substituted with aryl-C(=O)— or $C_{1-4}$alkyloxycarbonyl; hydroxy$C_{1-6}$alkyl optionally substituted with aryl or aryl-C(=O)—; amino; mono- or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; $C_{3-6}$cycloalkyl; $C_{3-6}$cycloalkyl$C_{1-4}$alkyl; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—; more in particular $C_{1-6}$alkyl optionally substituted with aryl-C(=O)— or $C_{1-4}$alkyloxycarbonyl; hydroxy$C_{1-6}$alkyl optionally substituted with aryl; mono- or di($C_{1-6}$alkyl)amino; $R^5R^4N$—$C_{1-6}$alkyl; $C_{3-6}$cycloalkyl-$NR^x$—; Het-$NR^x$—; aryl$C_{1-4}$alkyl-$NR^x$—; $C_{3-6}$cycloalkyl; $C_{3-6}$cycloalkyl$C_{1-4}$alkyl; aryl; aryl$C_{1-4}$alkyl; aryl-C(=O)—$C_{1-4}$alkyl or Het.

A sixth embodiment of the present invention are those compounds of formula (I) or, whenever possible, any subgroup thereof as mentioned hereinbefore as embodiment wherein the compound of formula (I) is a compound of formula (I')

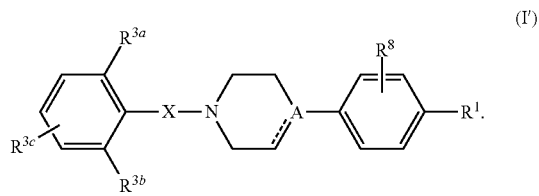

(I')

wherein $R^{3a}$ and $R^{3a}$ each independently represent hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $C_{1-4}$alkylcarbonylamino; —S(=O)$_p$—$C_{1-4}$alkyl; and wherein $R^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; $R^5R^4N$—C(=O)—; $R^5R^4N$—$C_{1-6}$alkyl; $C_{3-6}$cycloalkyl; aryl; aryloxy; aryl$C_{1-4}$alkyl; aryl-C(=O)—; Het; Het$C_{1-4}$alkyl; Het-C(=O)—; Het-O—.

A seventh embodiment of the present invention are those compounds of formula (I) or, whenever possible, any subgroup thereof as mentioned hereinbefore as embodiment wherein the compound of formula (I) is a compound of formula (I")

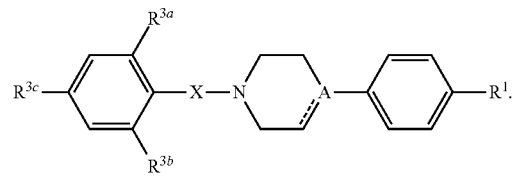

(I")

wherein $R^{3a}$ and $R^{3a}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein $R^{3c}$ represents hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyl-oxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonyl-amino; —S(=O)$_p$—$C_{1-4}$alkyl; $R^5R^4N$—C(=O)—; $R^5R^4N$—$C_{1-6}$alkyl; $C_{3-6}$cycloalkyl; aryl; aryloxy; aryl$C_{1-4}$alkyl; aryl-C(=O)—; Het; Het$C_{1-4}$alkyl; Het-C(=O)—; Het-O—.

An eighth embodiment of the present invention are those compounds of formula (I) or, whenever possible, any subgroup thereof as mentioned hereinbefore as embodiment wherein the compound of formula (I) is a compound of formula (I') or (I") and wherein $R^{3a}$ and $R^{3b}$ each independently represent halo, polyhalo$C_{1-6}$alkyl, $C_{1-6}$alkyl or $C_{1-6}$alkyloxy, in particular both $R^{3a}$ and $R^{3b}$ represent halo, more in particular both $R^{3a}$ and $R^{3b}$ represent chloro.

A ninth embodiment of the present invention are those compounds of formula (I) or, whenever possible, any subgroup thereof as mentioned hereinbefore as embodiment wherein the compound of formula (I) is a compound of formula (I') or (I") and wherein $R^{3c}$ represents hydrogen, hydroxyl, carboxyl; halo; amino; mono- or di-($C_{1-4}$alkyl)amino; $C_{1-6}$alkyl; $C_{1-6}$alkyloxy; $C_{1-6}$alkyloxycarbonyl; $C_{1-6}$alkylthio; $C_{1-4}$alkylcarbonylamino; $R^5R^4N$—C(=O)—; $R^5R^4N$—$C_{1-6}$alkyl; Het-C(=O)— or Het$C_{1-4}$alkyl; or $R^{3c}$ represents hydrogen.

A tenth embodiment of the present invention are those compounds of formula (I) or, whenever possible, any subgroup thereof as mentioned hereinbefore as embodiment wherein p represents 2.

An eleventh embodiment of the present invention are those compounds of formula (I) or, whenever possible, any subgroup thereof as mentioned hereinbefore as embodiment wherein Z represents $C_{1-6}$alkanediyl, in particular $CH_2$ or $CH_2$—$CH_2$.

A twelfth embodiment of the present invention are those compounds of formula (I) or, whenever possible, any subgroup thereof as mentioned hereinbefore as embodiment wherein $R^x$ represents hydrogen.

A thirteenth embodiment of the present invention are those compounds of formula (I) or, whenever possible, any subgroup thereof as mentioned hereinbefore as embodiment wherein $R^8$ represents hydrogen.

A fourteenth embodiment of the present invention are those compounds of formula (I) or, whenever possible, any subgroup thereof as mentioned hereinbefore as embodiment wherein R⁸ represents halo, $C_{1-4}$alkyl or $C_{1-4}$alkyl substituted with hydroxyl; in particular R⁸ represents halo or $C_{1-4}$alkyl.

A fifteenth embodiment of the present invention are those compounds of formula (I) or, whenever possible, any subgroup thereof as mentioned hereinbefore as embodiment wherein R³ represents $C_{3-6}$cycloalkyl, phenyl, naphtalenyl, 1,3-benzodioxolyl or a 6-membered aromatic heterocycle containing 1 or 2 N atoms, wherein said $C_{3-6}$cycloalkyl, phenyl, naphtalenyl, 1,3-benzodioxolyl or 6-membered aromatic heterocycle may optionally be substituted with at least one substituent, in particular one or two substituents, preferably each substituent independently selected from hydroxyl; carboxyl; halo; $C_{1-6}$alkyl optionally substituted with hydroxy; polyhalo$C_{1-6}$alkyl; $C_{1-6}$alkyloxy; $C_{1-6}$alkylthio; $C_{1-6}$alkyloxycarbonyl; amino; mono- or di($C_{1-4}$alkyl)amino; $C_{1-4}$alkylcarbonylamino; Het; Het$C_{1-4}$alkyl.

A sixteenth embodiment of the present invention are those compounds of formula (I) or any subgroup thereof as mentioned hereinbefore as embodiment wherein one or more, preferably all, of the following restrictions apply:
a) X represents —NR$^x$—C(=O)—; or —Z—C(=O)—;
b) the compound of formula (I) is a compound of formula (I″), in particular a compound of formula (I″) wherein R$^{3a}$ and R$^{3b}$ represent halo; more in particular chloro; and wherein R$^{3c}$ represents hydrogen;
c) A represents N;
d) A represents CH;
e) the dotted line does not represent a bond;
f) Z represents $C_{1-6}$alkanediyl;
g) R¹ represents a 5-membered monocyclic aromatic heterocycle containing at least 2 heteroatoms, in particular pyrazolyl or triazolyl; a 6-membered monocyclic aromatic heterocycle; or a 5-membered aromatic heterocycle containing at least 2 heteroatoms fused with a 5-membered heterocycle; each of said heterocycles optionally being substituted, in particular substituted with oxo, $C_{1-6}$alkyl optionally substituted with aryl-C(=O)—; hydroxy$C_{1-6}$alkyl optionally substituted with aryl; $C_{3-6}$cycloalkyl-NR$^x$—; Het-NR$^x$—; aryl$C_{1-4}$alkyl-NR$^x$—; aryl; aryl$C_{1-4}$alkyl.
h) R$^x$ represents hydrogen.

A seventeenth embodiment of the present invention are those compounds of formula (I) or any subgroup thereof as mentioned hereinbefore as embodiment wherein one or more, preferably all, of the following restrictions apply:
a) A represents CH or N;
b) the dotted line does not represents a bond in case A represents a carbon atom;
c) X represents —NR$^x$—C(=O)—; —Z—C(=O)—; —Z—NR$^x$—C(=O)—;
d) Z represents a bivalent radical selected from $C_{1-6}$alkanediyl;
e) R$^x$ represents hydrogen;
f) R¹ represents a 5-membered monocyclic heterocycle containing at least 2 heteroatoms; a 6-membered aromatic monocyclic heterocycle; or a 5-membered heterocycle containing at least 2 heteroatoms fused with a 5-membered heterocycle; wherein each of said heterocycles such as for example pyrazolyl, triazolyl, oxadiazolyl, pyrimidinyl, imidazopyrazolyl or imidazothienyl, may optionally be substituted with at least one substituent, in particular one or two substituents, each substituent independently being selected from oxo; $C_{1-6}$alkyl optionally substituted with $C_{1-4}$alkyloxycarbonyl; hydroxy$C_{1-6}$alkyl optionally substituted with aryl; mono- or di($C_{1-6}$alkyl)amino; R⁵R⁴N—$C_{1-6}$alkyl; Het-NR$^x$—; aryl$C_{1-4}$alkyl-NR$^x$—; $C_{3-6}$cycloalkyl; $C_{3-6}$cycloalkyl$C_{1-4}$alkyl; aryl; aryl$C_{1-4}$alkyl; aryl-C(=O)—$C_{1-4}$alkyl; Het;

g) R³ represents $C_{3-6}$cycloalkyl, phenyl, naphtalenyl, 1,3-benzodioxolyl, or a 6-membered aromatic heterocycle containing 1 or 2 N atoms, wherein said $C_{3-6}$cycloalkyl, phenyl, naphtalenyl, 1,3-benzodioxolyl or 6-membered aromatic heterocycle may optionally be substituted with at least one substituent, in particular one or two substituents, each substituent independently selected from hydroxyl; carboxyl; halo; $C_{1-6}$alkyl optionally substituted with hydroxy; polyhalo$C_{1-6}$alkyl; $C_{1-6}$alkyloxy; $C_{1-6}$alkylthio; $C_{1-6}$alkyloxycarbonyl; mono- or di($C_{1-4}$alkyl)amino; $C_{1-4}$alkyl-carbonylamino; Het; Het$C_{1-4}$alkyl;
h) R⁴ represents hydrogen or $C_{1-4}$alkyl;
i) R⁵ represents hydrogen or $C_{1-4}$alkyl;
j) R⁸ represents hydrogen;
k) aryl represents phenyl or phenyl substituted with at least one substituent, in particular one substituent, said substituent being selected from halo; $C_{1-6}$alkyl; $C_{1-6}$alkyloxy;
l) Het represents a monocyclic non-aromatic or aromatic heterocycle containing at least one heteroatom selected from O, S, S(=O)$_p$ or N; said monocyclic heterocycle optionally being substituted with $C_{1-6}$alkyloxycarbonyl.

Preferred compounds of formula (I) are selected from

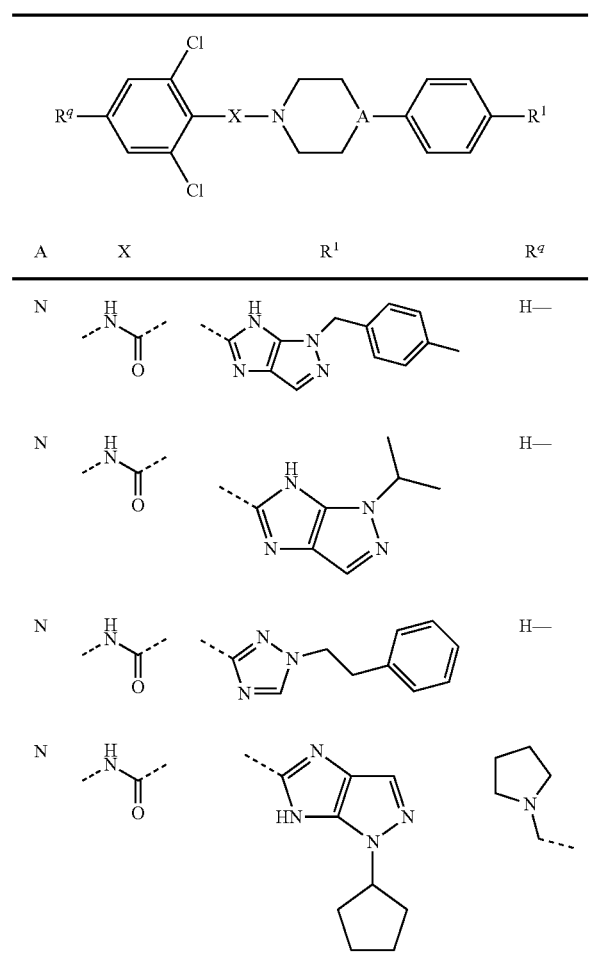

-continued

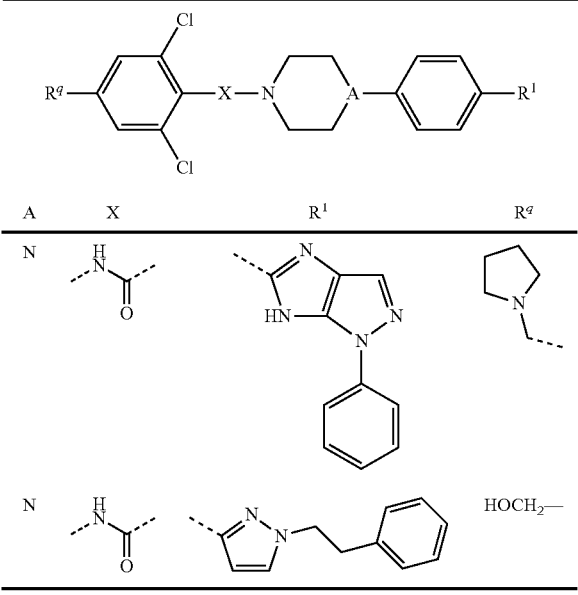

a N-oxide thereof, a pharmaceutically acceptable salt thereof or a solvate thereof.

In general, compounds of formula (I) wherein X represents $X_1$—NH—C(=O)— with $X_1$ representing a direct bond or Z, said compounds being represented by formula (I-a), can be prepared by reacting an intermediate of formula (II) with an intermediate of formula (III) in the presence of a suitable solvent, such as for example N,N-dimethylformamide or dichloromethane or acetonitrile, optionally in the presence of a suitable base, such as for example N,N-diethyl-ethanamine. Intermediates of formula (II) are commercially available or can be prepared by reacting $R^2$—$X_1$—$NH_2$ with phosgene in the presence of a suitable solvent, such as for example toluene.

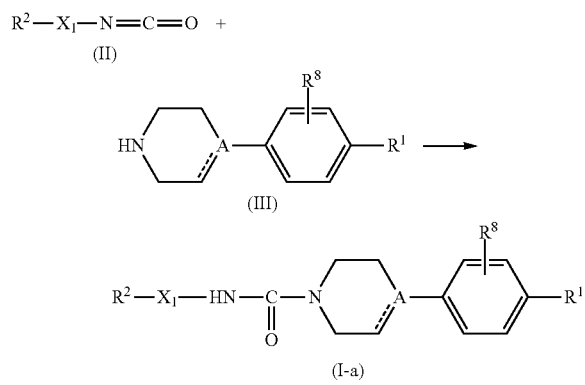

The above reaction can also be performed as a fast synthesis reaction thereby using appropriate reagents well-known for fast synthesis, such as for example for the purification of the reaction mixture 1-ethenyl-4-(isocyanatomethyl)-benzene polymer with ethenylbenzene and tris-2-aminoethylamine linked to polystyrene can be used.

Compounds of formula (I-a) wherein $X_1$ represents a direct bond, said compounds being represented by formula (I-a-1), can be prepared by reacting an intermediate of formula (II') with $Cl_3COC(=O)$—Cl or $C(=O)Cl_2$, optionally in the presence of HCl in diethylether, and in the presence of a suitable solvent, such as for example toluene or acetonitrile, followed by reaction with an intermediate of formula (III) in the presence of a suitable solvent, such as for example acetonitrile, N,N-dimethylformamide or dichloromethane, optionally in the presence of a suitable base, such as for example N,N-diethyl-ethanamine or N,N-diisopropyl-ethanamine

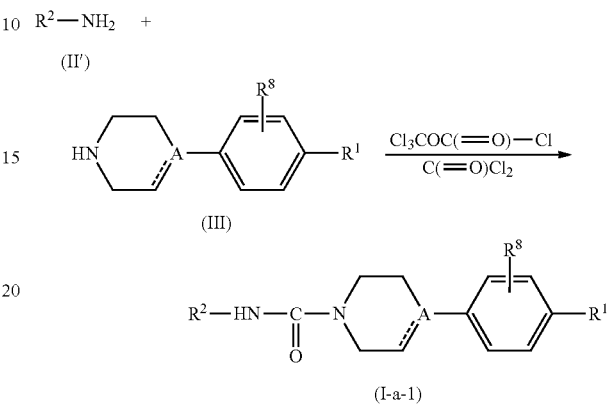

Compounds of formula (I) wherein X represents —$X_1$—C(=O)— with $X_1$ representing a direct bond or Z, said compounds being represented by formula (I-b), can be prepared by reacting an intermediate of formula (IV) with an intermediate of formula (III) in the presence of a suitable dehydrating (coupling) agent, such as for example N'-(ethyl-carbonimidoyl)-N,N-dimethyl-1,3-propanediamine monohydrochloride (EDCI), dicyclohexylcarbodiimide (DCC), carbonyl diimidazole (CDI), 1-[bis(di-methyl-amino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, tetrahydrofuran or dichloromethane, and optionally in the presence of a suitable base, such as for example N,N-diisopropyl-ethanamine or N,N-diethyl-ethanamine. This reaction of an intermediate of formula (IV) with an intermediate of formula (III) can also be performed in the presence of a suitable activating agent, such as for example Cl—C(=O)—C(=O)—Cl, a suitable base, such as for example N,N-diethyl-ethanamine, and a suitable solvent, such as for example N,N-dimethylformamide.

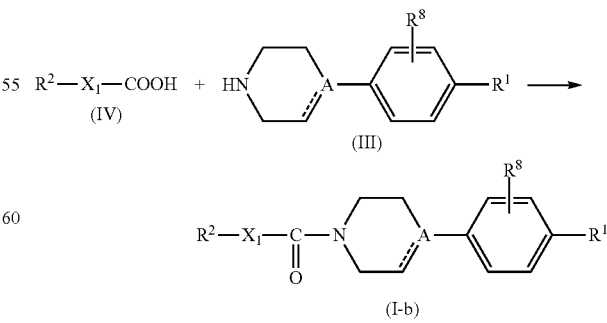

Compounds of formula (I-b) wherein $X_1$ represents a direct bond, said compounds being represented by formula (I-b-1), can be prepared by reacting an intermediate of formula (IV')
wherein $W_1$ represents a suitable leaving group, such as for
example halo, e.g. chloro and the like, with an intermediate of
formula (III) in the presence of a suitable base, such as for
example N-methyl morpholine, and a suitable solvent, such
as for example N,N-dimethylformamide.

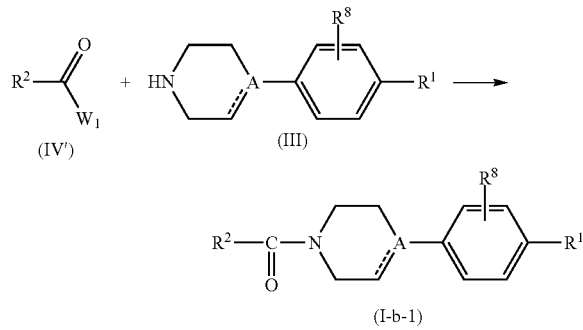

Compounds of formula (I) wherein X represents
$X_1$—NH—C(=S)— with $X_1$ representing a direct bond or Z,
said compounds being represented by formula (I-c), can be
prepared by reacting an intermediate of formula (XV) with an
intermediate of formula (III) in the presence of a suitable
solvent, such as for example tetrahydrofuran or dichloromethane, optionally in the presence of a suitable base, such
as for example N,N-diethyl-ethanamine.

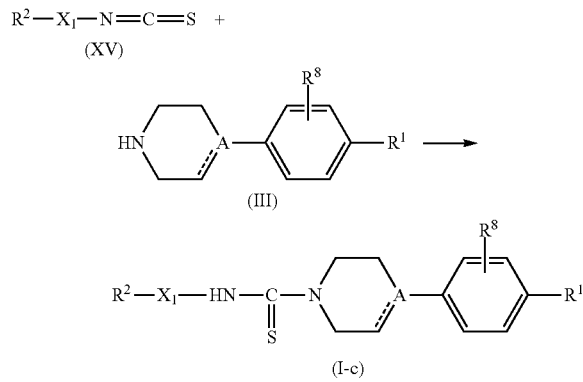

Compounds of formula (I) wherein X represents —S
$(=O)_p$—, said compounds being represented by formula
(I-d), can be prepared by reacting an intermediate of formula
(XIV) wherein $W_3$ represents a suitable leaving group, such
as for example halo, e.g. chloro and the like, with an intermediate of formula (III) in the presence of a suitable base, such
as for example N,N-diisopropyl-ethanamine or N,N-diethylethanamine, and a suitable solvent, such as for example
dichloromethane.

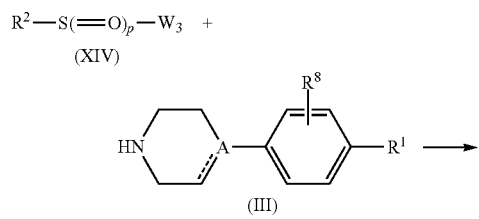

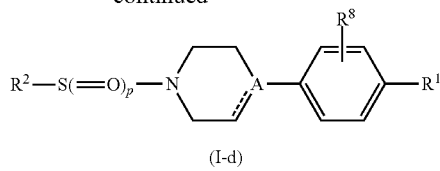

Compounds of formula (I) wherein X represents
—C(=O)—$C_{2-6}$alkenediyl-, said compounds being represented by formula (I-e), can be prepared by reacting an intermediate of formula (XV) with an intermediate of formula (III)
in the presence of a suitable solvent, such as for example an
alcohol, e.g. ethanol.

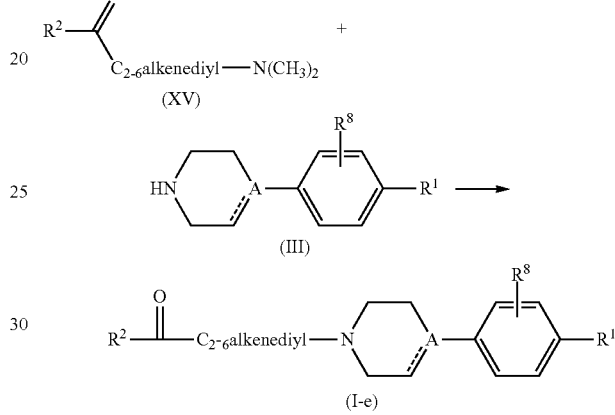

Compounds of formula (I) wherein $R^2$ represents $R^3$, said
$R^3$ being substituted with $R^5R^4N$—$C_{1-6}$alkyl, said $R^2$ being
represented by —$R^{3'}$-$C_{1-6}$alkyl-$NR^4R^5$ and said compounds
being represented by formula (I-f), can be prepared by reacting an intermediate of formula (XVI) wherein $W_4$ represents
a suitable leaving group, such as for example $CH_3$—$S(=O)_2$
—O—, with $NHR^4R^5$ in the presence of a suitable solvent,
such as for example acetonitrile. Intermediates of formula
(XVI) can be prepared by reacting the corresponding OH
derivatives with $CH_3$—$S(=O)_2$—Cl in the presence of a
suitable base, such as for example pyridine, and a suitable
solvent, such as for example dichloromethane.

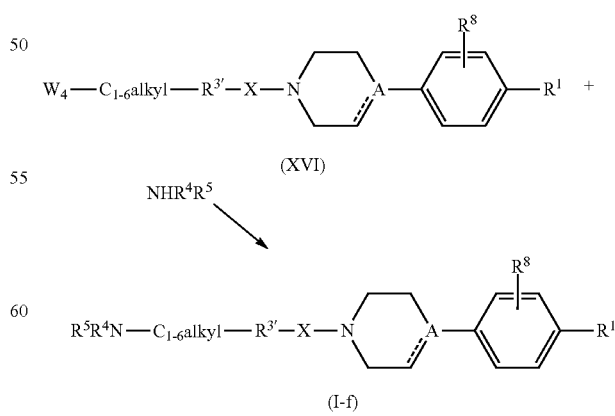

Compounds of formula (I) wherein the $R^1$ substituent is
substituted with amino can be prepared from the corresponding compound wherein the amino function is protected by a suitable protecting group, such as for example a tertiair butyloxycarbonyl group, in the presence of a suitable acid, such as for example trifluoroacetic acid, and a suitable solvent, such as for example dichloromethane. Said protected compounds can be prepared according to the synthesis protocol described hereinabove.

Compounds of formula (I) wherein X contains Z, said Z being substituted with amino, said X being represented by $Z^1(NH_2)$—$X_2$, wherein $X_2$ represents the remainder of the linker X, and said compounds being represented by formula (I-g), can be prepared by deprotecting an intermediate of formula (XVIII) wherein P represents a suitable leaving group, such as for example tert butoxycarbonyl, with a suitable acid, such as for example trifluoroacetic acid, in the presence of a suitable solvent, such as for example dichloromethane.

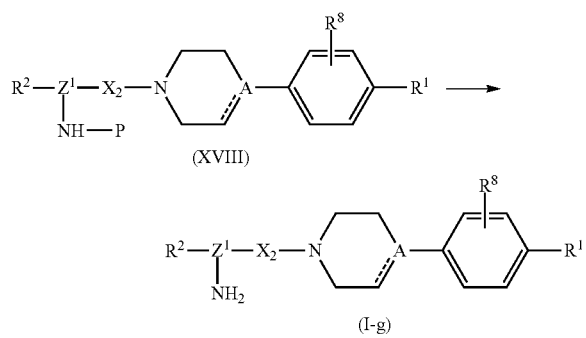

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$ or $R^2$ is unsubstituted, can be converted into a compound wherein $R^1$ or $R^2$ contain a $C_{1-4}$alkyl-S(=O)$_p$— substituent, by reaction with $C_{1-4}$alkyl-S(=O)$_p$—$W_5$ wherein $W_5$ represents a suitable leaving group, such as for example halo, e.g. chloro and the like, in the presence of a suitable base, such as for example N,N-diethyl-ethanamine, and in the presence of a suitable solvent, such as for example acetonitrile.

Compounds of formula (I) wherein $R^1$ or $R^2$ contains a $C_{1-6}$alkyloxycarbonyl substituent, can be converted into a compound of formula (I) wherein $R^1$ or $R^2$ contain a carboxyl substituent, by reaction with a suitable base, such as for example sodium hydroxide, in the presence of a suitable solvent, such as for example dioxane.

Compounds of formula (I) wherein $R^1$ or $R^2$ contain a $C_{1-6}$alkyloxycarbonyl substituent, can also be converted into a compound of formula (I) wherein $R^1$ or $R^2$ contain a $CH_2$—OH substituent, by reaction with a suitable reducing agent, such as for example LiBH, in the presence of a suitable solvent, such as for example tetrahydrofuran or dioxane.

Compounds of formula (I) wherein $R^1$ or $R^2$ contain a $C_{1-6}$alkyloxycarbonyl substituent, can also be converted into a compound of formula (I) wherein $R^1$ or $R^2$ are unsubstituted by reaction with a suitable acid, such as for example hydrochloric acid and the like.

Compounds of formula (I) wherein $R^1$ or $R^2$ contain a $C_{1-5}$alkyl-carbonyl substituent, can be converted into a compound of formula (I) wherein $R^1$ or $R^2$ contain a $C_{1-5}$alkyl-CH(OH)— substituent, by reaction with a suitable reducing agent, such as for example $NaBH_4$, in the presence of a suitable solvent, such as for example an alcohol, e.g. methanol.

Compounds of formula (I) wherein $R^1$ or $R^2$ contain a $C_{1-6}$alkyloxy substituent, can be converted into a compound of formula (I) wherein $R^1$ or $R^2$ contain a OH substituent, by reaction with a suitable reducing agent, such as for example $BBr_3$, in the presence of a suitable solvent, such as for example dichloromethane or dichloroethane.

Compounds of formula (I) wherein $R^1$ or $R^2$ contain a carboxyl substituent, can be converted into a compound of formula (I) wherein $R^1$ or $R^2$ contain a Het-C(=O)-substituent wherein Het represents an optionally substituted monocyclic saturated heterocycle containing at least one N atom, said heterocycle being linked via the N atom to the C(=O) group, by reaction with said heterocycle in the presence a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)-methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction can also be performed as a fast synthesis reaction thereby using appropriate reagents well-known for fast synthesis, such as for example dicyclohexylcarbodiimide (DCC) or carbonyl diimidazole (CDI), linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene.

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography or SCF (Super Critical Fluid) chromatography, in particular using a chiral stationary phase.

Some of the intermediates and starting materials are known compounds and may be commercially available or may be prepared according to art-known procedures.

Intermediates of formula (III) can be prepared by deprotecting an intermediate of formula (V) wherein P represents a suitable protective group, such as for example benzyl or $C_{1-4}$alkyloxycarbonyl, e.g. $CH_3CH_2$—O—C(=O)— or $(CH_3)_3C$—O—C(=O)—.

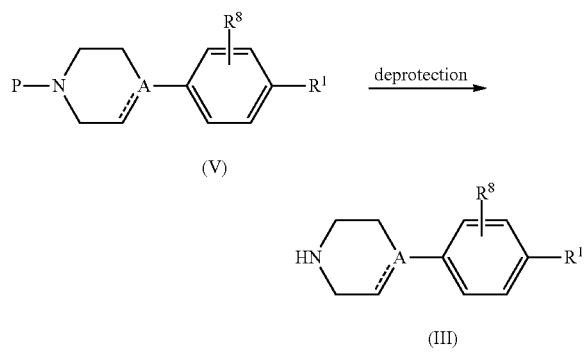

In the above reaction, when P represents for instance benzyl, appropriate deprotection conditions are deprotection in the presence of $H_2$, a suitable catalyst, such as for example palladium on charcoal or $Pd(OH)_2$, a suitable solvent, such as for example tetrahydrofuran or an alcohol, e.g. methanol. When P represents for instance $(CH_3)_3C$—O—C(=O)—, appropriate deprotection conditions are deprotection in the presence of a suitable acid, such as for example HCl or trifluoroacetic acid, in the presence of a suitable solvent, such as for example acetonitrile, dichloromethane or an alcohol, e.g. propanol. When P represents for instance $CH_3CH_2$—O—C(=O)—, appropriate deprotection conditions are deprotection in the presence of a suitable acid, such as for example HBr, in the presence of $Na_2SO_3$, or deprotection in the presence of a suitable base, such as for example KOH, in the presence of a suitable solvent, such as for example water, ethylene glycol or an alcohol, e.g. propanol.

Intermediates of formula (V) wherein $R^1$ represents optionally substituted pyrazolyl, said intermediates being represented by formula (V-a) wherein $R^{1a}$ represents the optional substituent, can be prepared by reacting an intermediate of formula (VI) with an intermediate of formula (VII) in the presence of a suitable solvent, such as for example an alcohol, e.g. ethanol, and optionally in the presence of sodium.

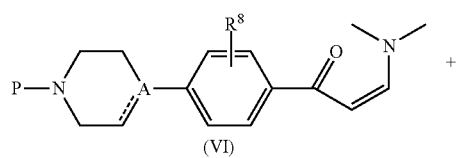

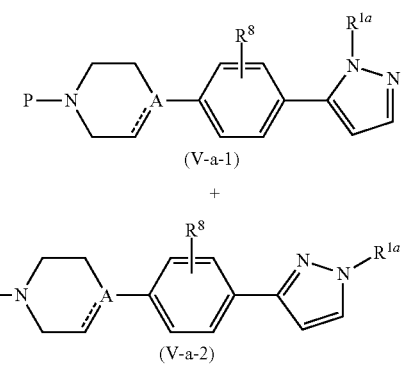

Intermediates of formula (V) wherein $R^1$ represents optionally substituted triazolyl, said intermediates being represented by formula (V-b) wherein $R^{3a}$ represents the optional substituent, can be prepared by reacting an intermediate of formula (VIII) with an intermediate of formula (VII) in the presence of a suitable solvent, such as for example an alcohol, e.g. ethanol, and in the presence of a suitable base, such as for example sodium, or in the presence of a suitable acid, such as for example acetic acid.

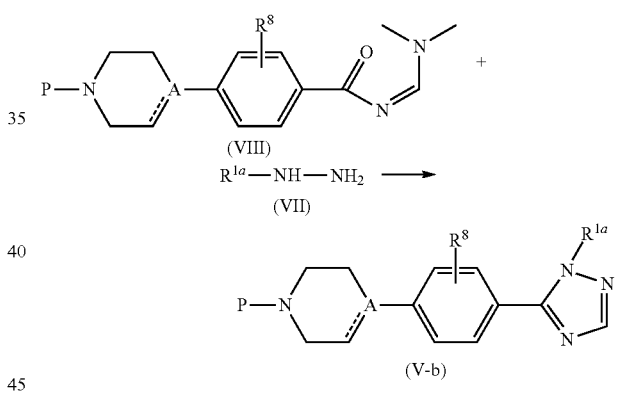

Intermediates of formula (V) wherein $R^1$ represents optionally substituted pyrimidinyl, said intermediates being represented by formula (V-c) wherein $R^{3a}$ represents the optional substituent, can be prepared by reacting an intermediate of formula (VI) with an intermediate of formula (IX) in the presence of a suitable solvent, such as for example an alcohol, e.g. ethanol, and optionally in the presence of sodium.

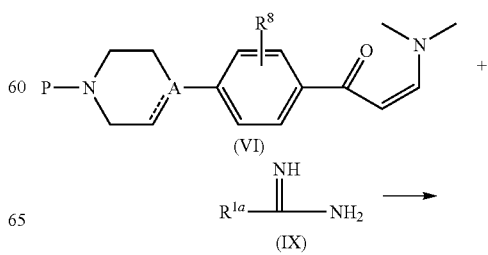

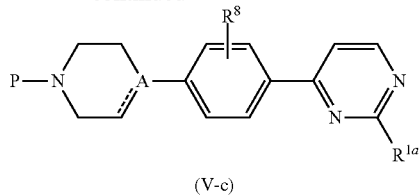

(V-c)

Intermediates of formula (V) wherein $R^1$ represents optionally substituted imidazopyrazolyl, said intermediates being represented by formula (V-d) wherein $R^{3a}$ represents the optional substituent, can be prepared by reacting an intermediate of formula (X) with an intermediate of formula (XI) in the presence of a suitable solvent, such as for example N,N-dimethylformamide, a suitable base, such as for example DIPEA, and a suitable dehydrating (coupling) agent, such as for example N'-(ethyl-carbonimidoyl)-N,N-dimethyl-1,3-propanediamine monohydrochloride (EDCI), dicyclohexylcarbodiimide (DCC), carbonyl diimidazole (CDI), 1-[bis(di-methyl-amino)methylene]-1H-benzotriazolium-hexafluorophosphate(1-)3-oxide (HBTU), 1-[bis(dimethyl-amino)methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, followed by reaction with POCl₃ in the presence of a suitable solvent, such as for example dioxane. This reaction of an intermediate of formula (X) with an intermediate of formula (XI) can also be performed in the presence of a suitable activating agent, such as for example Cl—C(=O)—C(=O)—Cl, a suitable base, such as for example N,N-diethylethanamine, and a suitable solvent, such as for example N,N-dimethylformamide. Alternatively, intermediates of formula (V-d) can also be directly prepared from an intermediate of formula (X) and an intermediate of formula (XI) in the presence of POCl₃.

Intermediates of formula (V) wherein $R^1$ represents optionally substituted oxadiazole, said intermediates being represented by formula (V-e-1) wherein $R^{1a}$ represents the optional substituent, can be prepared by reacting an intermediate of formula (X) with an intermediate of formula (XXI) in the presence of a suitable solvent, such as for example N,N-dimethylformamide, a suitable base, such as for example DIPEA, and a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(dimethyl-amino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, followed by reaction of the resulting intermediate of formula (XXII) with Burgess' reagent (CAS 29684-56-8) in the presence of a suitable solvent, such as for example tetrahydrofuran.

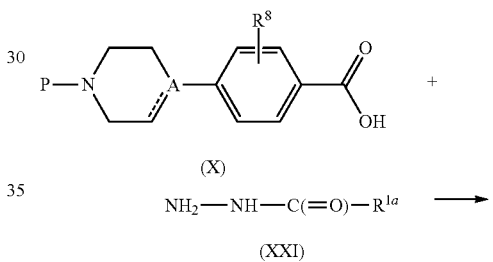

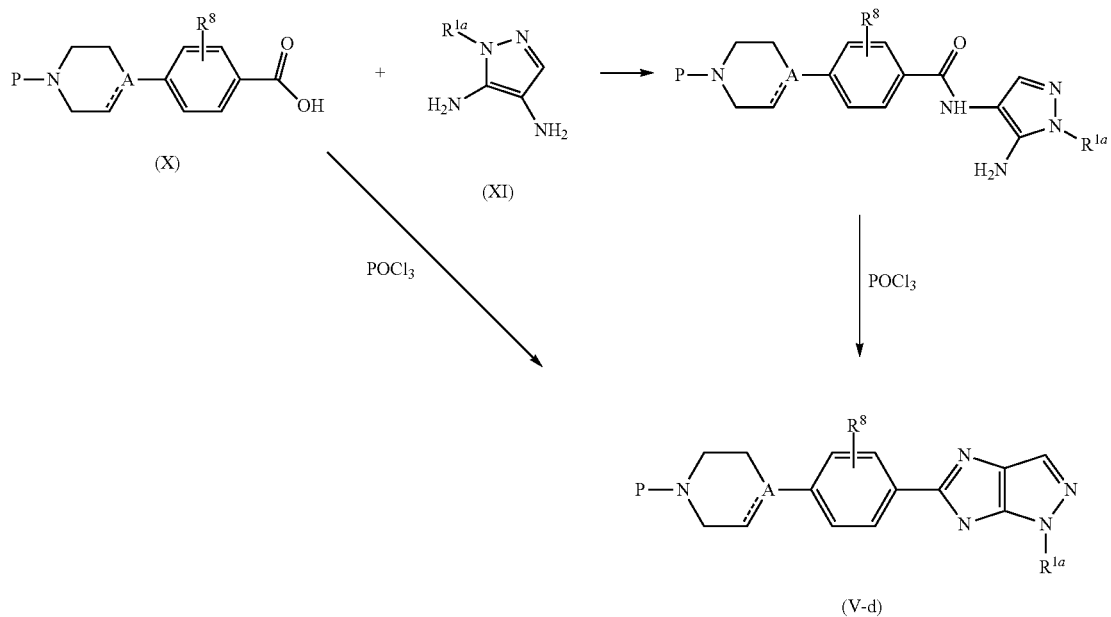

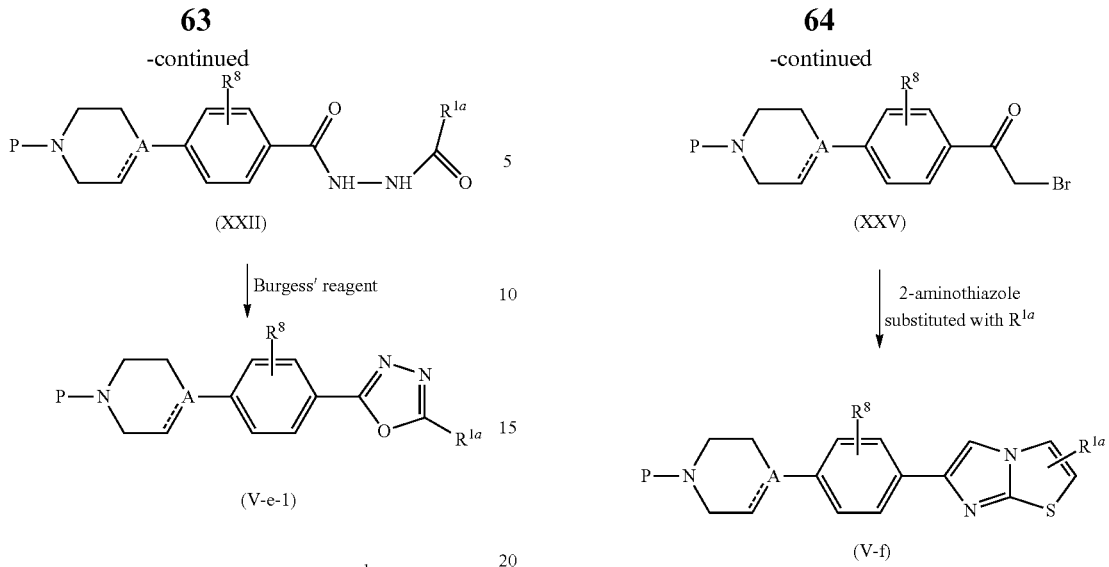

(XXII)

Burgess' reagent (V-e-1)

Intermediates of formula (V) wherein $R^1$ represents optionally substituted oxadiazole, said intermediates being represented by formula (V-e-2) wherein $R^{3a}$ represents the optional substituent, can be prepared by reacting an intermediate of formula (XXIII) with an intermediate of formula (XXIV) in the presence of a suitable base, such as for example sodium hydride, and a suitable solvent, such as for example tetrahydrofuran.

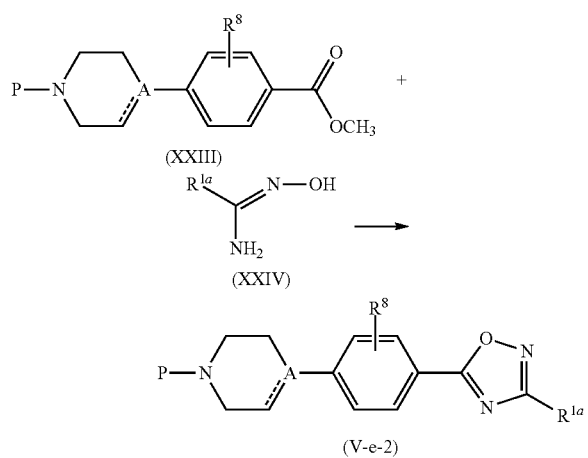

(XXIII)

(XXIV)

(V-e-2)

Intermediates of formula (V) wherein $R^1$ represents optionally substituted imidazothiazole, said intermediates being represented by formula (V-f) wherein $R^{3a}$ represents the optional substituent, can be prepared by reacting an intermediate of formula (XII) (see below) with $Br_2$ in the presence of HBr/acetic acid, followed by reacting the resulting intermediate of formula (XXV) with 2-amino-thiazole in the presence of a suitable solvent, such as for example an alcohol, e.g. ethanol.

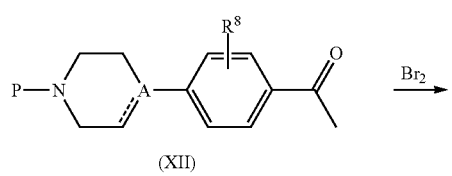

(XII)

(XXV)

2-aminothiazole substituted with $R^{1a}$ (V-f)

When $R^1$ in an intermediate of formula (V) represents an unsubstituted heterocycle or triazolone an appropriate substituent $R^{1a}$ can be introduced by reaction with $W_1-R^{1a}$, wherein $W_1$ represents a suitable leaving group, such as for example halo, e.g. chloro or bromo, in the presence of a suitable base, such as for example NaH, KOH, $Na_2CO_3$ or $Cs_2CO_3$, and a suitable solvent, such as for example N,N-dimethylformamide or N,N-dimethylacetamide.

Intermediates of formula (X) wherein P is for instance benzyl can be prepared by hydrolysis of the corresponding ester in the presence of a suitable acid, such as for example HCl, or a suitable base, such as for example sodium hydroxide, in the presence of a suitable solvent, such as for example dioxane. Or intermediates of formula (X) wherein P is $(CH_3)_3$C—O—C(=O)— can be prepared by hydrolysis of the corresponding ester in the presence of a suitable base, such as for example sodium hydroxide, and a suitable solvent, such as for example tetrahydrofuran, dioxane or an alcohol, e.g. methanol. The corresponding esters can be prepared by reacting the protected piperidine/piperazine with ethyl benzoate substituted in position 4 with a suitable leaving group, such as for example halo, e.g. fluoro and the like, in a suitable solvent, such as for example N,N-dimethylacetamide.

Intermediates of formula (VI) can be prepared by reacting an intermediate of formula (XII) with $CH_3O$—$CH(OCH_3)$—$N(CH_3)_2$.

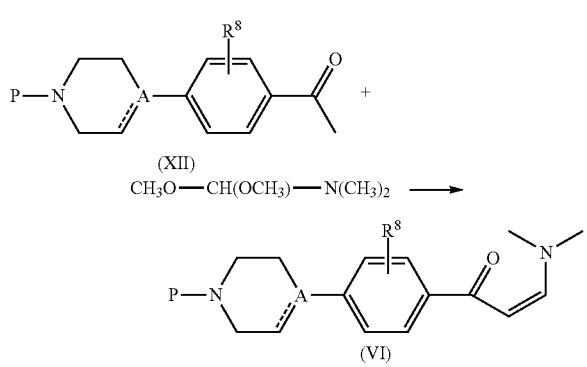

(XII)

$CH_3O$—$CH(OCH_3)$—$N(CH_3)_2$ (VI)

Intermediates of formula (VIII) can be prepared by reacting an intermediate of formula (XIII) with $CH_3O$—CH$(OCH_3)$—$N(CH_3)_2$.

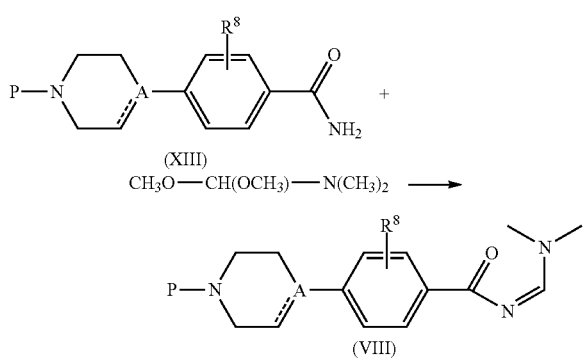

Intermediates of formula (XII) wherein P represents tertiair butyloxycarbonyl, can be prepared by reacting 1-[4-(1-piperazinyl)phenyl]ethanone with C,C'-bis(1,1-dimethylethyl)dicarbonic acid ester in the presence of a suitable solvent, such as for example dichloromethane. Intermediates of formula (XII) wherein P represents benzyl can be prepare by reacting 1-[4-(1-piperazinyl)phenyl]ethanone with benzylbromide in the presence of a suitable base, such as for example $Na_2CO_3$, and a suitable solvent, such as for example tetrahydrofuran.

Intermediates of formula (XIII) can be prepared by reacting an intermediate of formula (X) with $NH_3$ in the presence of a suitable solvent, such as for example N,N-dimethylformamide, and in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole.

Intermediates of formula (II) wherein $X_1$ represents a direct bond and $R^2$ contains a Het-$C_{1-4}$alkyl substituent, wherein Het represents a monocyclic, saturated N containing heterocycle represented by formula (XXXII), said intermediate of formula (IV) being represented by formula (II-a), can be prepared by reacting an intermediate of formula (XXI) with an intermediate of formula (XXVI) in the represence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethylamino)-methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. The resulting intermediate of formula (XXVII) can then be reduced in a next step in the presence of a suitable reducing agent, such as for example borane, in the presence of a suitable solvent, such as for example tetrahydrofuran, to an intermediate of formula (XXVIII), which can then be converted into an intermediate of formula (II-a) with phosgene in the presence of HCl in diethylether and a suitable solvent, such as for example toluene or acetonitrile. Intermediates of formula (XXVII) can also be converted into an intermediate of formula (II-b) with phosgene in the presence of HCl in diethylether and a suitable solvent, such as for example toluene or acetonitrile or dichloromethane.

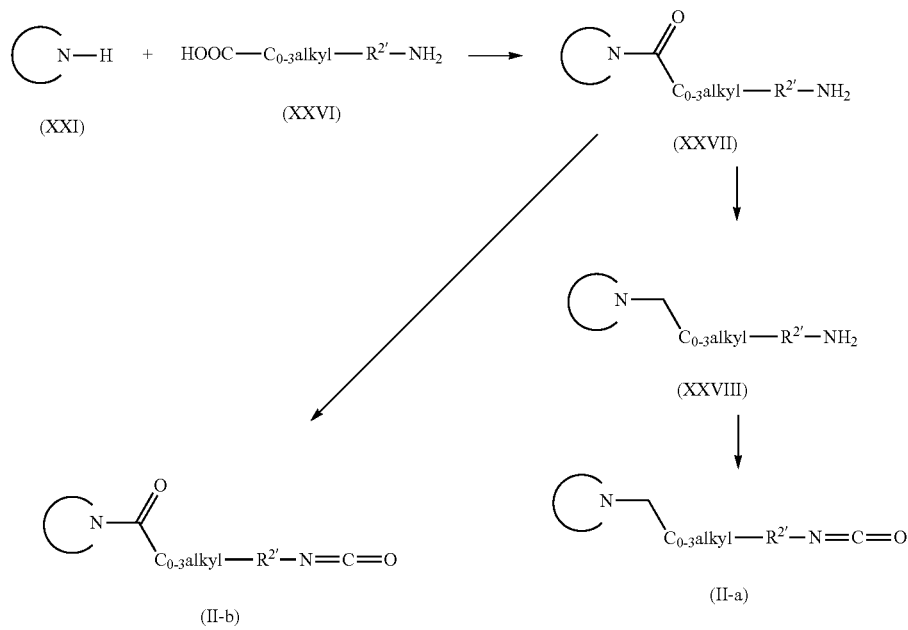

Intermediates of formula (II') wherein $R^2$ contains a Het-$C_{1-4}$alkyl substituent, said intermediate being represented by formula (II'-a), can be prepared by reacting an intermediate of formula (XIX) with an intermediate of formula (XX) wherein $W_6$ represents a suitable leaving group, such as for example halo, e.g. chloro and the like, in the presence of a suitable solvent, such as for example acetonitrile, resulting in an intermediate of formula (II'-a) with can be converted into an intermediate of formula (II-a) as described hereinabove for intermediate (XXVIII).

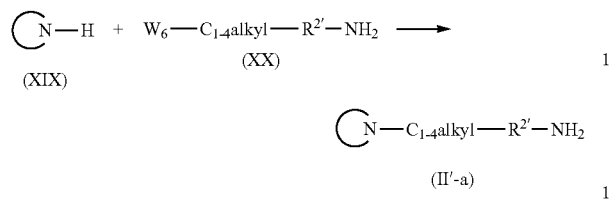

Intermediates of formula (IV) can be prepared by hydrolysis of an intermediate of formula (XXIX)) in the presence of LiOH, an acid, such as for example HCl, and a suitable solvent, such as for example an alcohol, e.g. methanol. Intermediates of formula (XXIX)) wherein $R^2$ contains Het-$C_{1-4}$ alkyl as substituent, said intermediates being represented by formula (XXIX-a) can be prepared by reacting an intermediate of formula (XXX) wherein $W_7$ represents a suitable leaving group, such as for example halo, e.g. bromo and the like, with an intermediate of formula (XXI). Intermediates of formula (XXX-a) as depicted below, can be prepared by reacting an intermediate of formula (XXXI) with N-bromosuccinimide in the presence of 2,2'-(1,2-diazenediyl)-bis[2-methyl-propanenitrile] and a suitable solvent, such as for example $CCl_4$.

Intermediates of formula (XXXI) wherein $X_1$ represents $CH_2$, said intermediates being represented by formula (XXXI-a), can be prepared by reacting an intermediate of formula (XXXII) with sodium metal, in the presence of a suitable alcohol of formula $C_{1-4}$alkyl-OH, followed by adding a suitable acid, such as for example sulfuric acid. Intermediates of formula (XXXII) can be prepared by reacting an intermediate of formula (II'-b) with 1,1-dimethylethyl-nitrous acid ester, $CuCl_2$, 1,1-dichloroethene in a suitable solvent, such as for example acetonitrile.

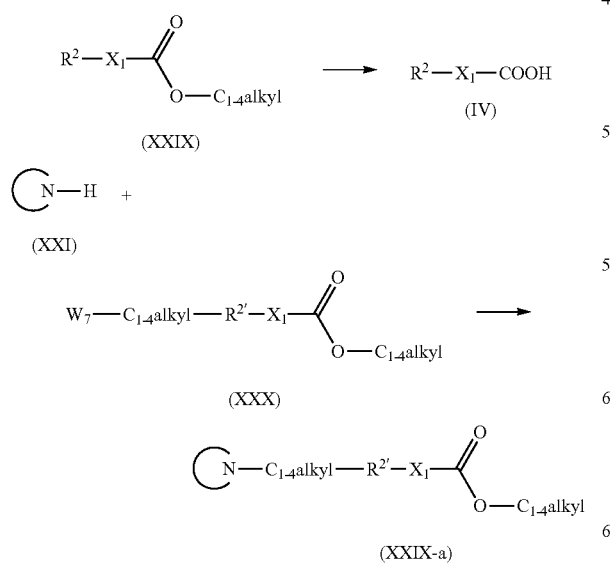

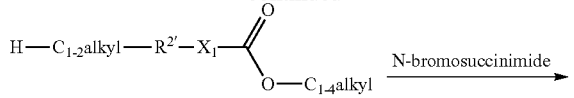

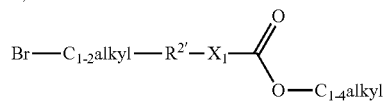

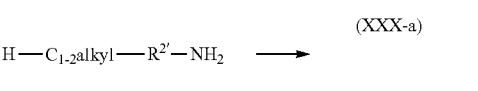

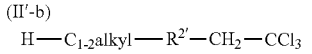

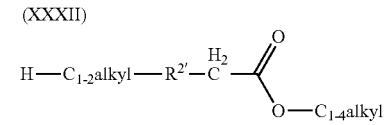

Intermediates of formula (XXVIII-a) can be prepared by reacting an intermediate of formula (IV) wherein $X_1$ is substituted with a protected (P, such as for example tertiair butyloxycarbonyl) amino group, said intermediate being represented by formula (IV-a), with an intermediate of formula (III) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)-methylene]-5-chloro-1H-benzotriazolium-hexafluorophosphate(1-) 3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine

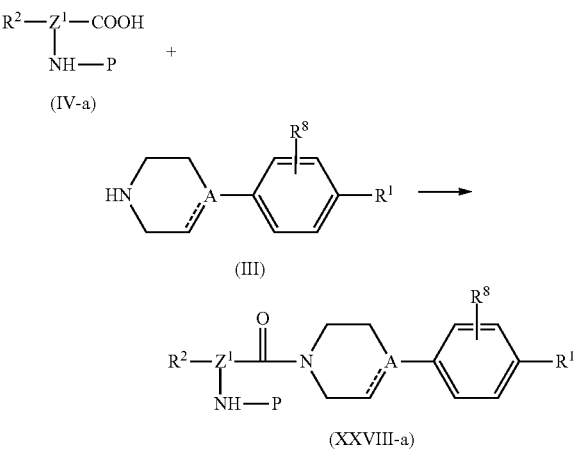

Intermediates of formula (IV) wherein $X_1$ represents CHOH, said intermediates being represented by formula (IVb) can be prepared by reducing an intermediate of formula (XVII) in the presence of ZnBr$_2$, Si(CH$_3$)$_3$—CN and an acid, such as for example HCl, in the presence of a suitable solvent, such as for example dichloromethane. Intermediates of formula (XVII) can be prepared by reacting an intermediate of formula (XXXIII) wherein W$_8$ represents a suitable leaving group, such as for example halo, e.g. bromo and the like, with N,N-dimethylformamide in the presence of BuLi and a suitable solvent, such as for example tetrahydrofuran.

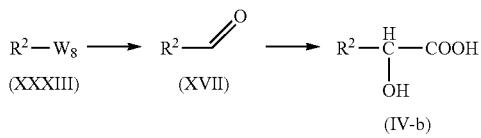

Pharmacological Part

As already indicated above, the present invention relates to the use of a DGAT inhibitor, in particular a DGAT1 inhibitor, to elevate levels of one or more satiety hormones, in particular GLP-1 levels. The present invention also relates to the use of a DGAT inhibitor, in particular a DGAT1 inhibitor, for the manufacture of a medicament for the prevention or the treatment, in particular for the treatment, of a disease which can benefit from an elevated level of one or more satiety hormones, in particular a disease which can benefit from an elevated GLP-1 level. In particular, GLP-1 levels are elevated in plasma or in portal blood, more in particular in plasma. By elevated GLP-1 levels, e.g. elevated GLP-1 plasma level or an elevated GLP-1 level in portal blood, it is meant that the GLP-1 level of a subject having taken a DGAT1 inhibitor is elevated or increased compared to the subject under the same conditions but not having taken the DGAT1 inhibitor. In particular GLP-1 levels are elevated in fasting conditions or postprandial, more in particular postprandial.

Therapeutic uses for a compound which elevates GLP-1 level include, but are not limited to, improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, hemorrhage, cerebrovascular accident, ADD, and neuropsychiatric syndromes; converting liver stem/progenitor cells into functional pancreatic cells; preventing beta-cell deterioration and stimulation of beta-cell proliferation; treating pancreatitis; treating obesity; suppressing appetite and inducing satiety; treating irritable bowel syndrome or inflammatory bowel disease such as Crohn's disease and ulcerative colitis; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction, e.g., with abnormal left ventricular ejection fraction; inhibiting antro-duodenal motility, e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS); modulating triglyceride levels and treating dyslipidemia; treating organ tissue injury (e.g. brain tissue injury) caused by reperfusion of blood flow following ischemia; improving the function of ischemic and reperfused brain tissue; treating coronary heart disease risk factor (CHDRF) syndrome. Further diseases which can benefit from an elevated GLP-1 level, include, but are not limited to, ischemic myocardial stunning; ishemic/reperfusion injury; acute myocardial infarction; left ventricular dysfunction; vascular disease; neuropathy, including periphere sensoric neuropathy associated with type II diabetes; bone-related disorders, including osteoporosis, obesity, diabetes. Because of the effect on GLP-1, the DGAT inhibitors can also be used to provide cardioprotection.

References supporting the above indications include Experimental Neurology, Vol. 203(2), pp 293-301 (2007); U.S. Pat. No. 7,186,683; J. Pharm. Exp. Ther. vol. 312, No. 1, pp 303-308 (2005); Diabetes, vol. 54, pp 146-151 (2005); US2007/0021339, which are incorporated herein by reference.

In view of the DGAT inhibitory activity, in particular the DGAT1 inhibitory activity, the present compounds of formula (I), their N-oxide forms, their pharmaceutically acceptable salts or their solvates, can be used as a medicine. In particular, the present invention relates to a compound of formula (I), a N-oxide form thereof, a pharmaceutically acceptable salt thereof or a solvate thereof for use as a medicine, in particular for use as a medicine for the prevention or the treatment of a disease which can benefit from an elevated GLP-1 level. In particular, the present invention also relates to the use of a compound of formula (I) for the manufacture of a medicament for the prevention or the treatment of a disease which can benefit from an elevated GLP-1 level, such as the diseases and disorders mentioned above.

In view of the above-described utility for a DGAT inhibitor, in particular a DGAT1 inhibitor, there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a DGAT inhibitor, in particular a DGAT 1 inhibitor, to a warm-blooded mammal, including a human.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a compound of formula (I), a N-oxide form thereof, a pharmaceutically acceptable salt thereof or a solvate thereof, to a warm-blooded mammal, including a human.

In view of the DGAT inhibitory activity, in particular the DGAT1 inhibitory activity, the present invention also relates to a compound of formula (I), a N-oxide form thereof, a pharmaceutically acceptable salt thereof or a solvate thereof for use as a medicine, in particular for use as a medicine for the prevention or the treatment of a diseases which can benefit from inhibition of DGAT, in particular DGAT1. The invention also relates to the use of a compound of formula (I), a N-oxide form thereof, a pharmaceutically acceptable salt thereof or a solvate thereof, for the manufacture of a medicament for the prevention or the treatment of a disease or disorder which can benefit from inhibition of DGAT, in particular DGAT1. Diseases or disorders which can benefit from inhibition of DGAT, in particular DGAT1 include, but are not limited to metabolic disorders, such as obesity and obesity related disorders (including peripheral vascular disease, cardiac failure, myocardial ischaemia, cerebral ischaemia, cardiac myopathies), diabetes, in particular type II diabetes mellitus, and complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia and nonalcoholic fatty liver disease, fatty liver, increased mesenteric fat, non-alcoholic steatohepatitis, liverfibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; and other diseases and conditions that are sensitive or responsive to modulation, in particular inhibition, of DGAT function, in particular DGAT1 function.

Particular diseases or disorders which can benefit from inhibition of DGAT, in particular DGAT1, are selected from obesity, hypercholesterolemia, hyperlipidemia, dyslipidemia, mixed dyslipidemia, hypertriglyceridemia, fatty liver, nonalcoholic fatty liver disease, liverfibrosis, non-alcoholic steatohepatitis and diabetes, in particular type II diabetes.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from inhibition of DGAT, in particular a method of treating a warm-blooded mammal, including a human, suffering from a disease which can benefit from inhibition of DGAT. Said methods comprise the administration of an effective amount of a compound of formula (I), a N-oxide form thereof, a pharmaceutically acceptable salt thereof or a solvate thereof, to a warm-blooded mammal, including a human.

The present invention also provides compositions for preventing or treating a disease which can benefit from an elevated GLP-1 level or which can benefit from inhibition of DGAT, in particular DGAT1, in particular for treating a disease which can benefit from elevated GLP-1 levels or which can benefit from inhibition of DGAT, in particular DGAT1. Said compositions comprise a therapeutically effective amount of a compound of formula (I), a N-oxide form thereof, a pharmaceutically acceptable salt thereof or a solvate thereof, and a pharmaceutically acceptable carrier.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

In view of the above described effects of DGAT inhibitors and/or the effect on GLP-1 levels by DGAT inhibitors, the present invention also relates to a) a combination of a DGAT inhibitor, in particular a DGAT1 inhibitor, more in particular a compound of formula (I), a N-oxide form thereof, a pharmaceutically acceptable salt thereof or a solvate thereof, and a dipeptidyl peptidase-4 inhibitor (DPP-4 inhibitor).

DPP-4 is a membrane-spanning cell surface aminopeptidase widely expressed in many tissues, such as liver, lung, kidney, intestinal brush-border membranes, lymphocytes, endothelial cells. DPP-4 cleaves peptides with a proline or alanine residue in the second aminoterminal position. Many gastro-intestinal hormones are substrates for DPP-4, among them GLP-1. A DPP-4 inhibitor thus inhibits cleavage of GLP-1 and hence provides for an increase in the level of GLP-1. Therefore, a combination as indicated above can be used to combine the activity of the DGAT inhibitor and the DPP4 inhibitor in order to elevate GLP-1 levels. By administering a DGAT inhibitor, in particular a DGAT1 inhibitor, more in particular a compound of formula (I), a N-oxide thereof, a pharmaceutically acceptable salt thereof or a solvate thereof, with a DPP4 inhibitor, different mechanisms may be targeted in order to achieve elevated levels of GLP-1. In this way, the use of such a combination may reduce the dosage of the DGAT inhibitor and the DPP4 inhibitor required for a desired elevation in GLP-1 level as compared to when the DGAT inhibitor or the DPP4 inhibitor is administered as a monotherapy. Therefore, these combinations may reduce or eliminate side effects of monotherapy while not interfering with the GLP-1 level increasing activity.

Also, the combination of a DGAT inhibitor, in particular a DGAT1 inhibitor, more in particular a compound of formula (I), a N-oxide form thereof, a pharmaceutically acceptable salt thereof or a solvate thereof, and a DPP4 inhibitor can be used as a medicine. The present invention also relates to a product comprising (a) a DGAT inhibitor, in particular a DGAT 1 inhibitor, more in particular a compound of formula (I), a N-oxide form thereof, a pharmaceutically acceptable salt thereof or a solvate thereof, and (b) a DPP4 inhibitor, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers. Said DPP4 inhibitor which may be combined with a DGAT inhibitor according to the present invention, in particular a DGAT1 inhibitor, may be a known DPP4 inhibitor such as for example sitagliptin, vildagliptin, and saxagliptin.

b) a combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue. Said GLP-1 analogue can be considered as an agonist at the GLP-1 receptor.

Also, the combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue can be used as a medicine. The present invention also relates to a product containing (a) a DGAT inhibitor, in particular a DGAT 1 inhibitor, more in particular a compound of formula (I), a N-oxide form thereof, a pharmaceutically acceptable salt thereof or a solvate thereof, and (b) a GLP-1 analogue, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers.

Said GLP-1 analogue which may be combined with a DGAT inhibitor according to the present invention may be a known GLP-1 analogue such as for example exenatide, exenatide LAR or liraglutide.

c) a combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum can be used as a medicine. The present invention also relates to a product containing (a) a DGAT inhibitor, in particular a DGAT 1 inhibitor, more in particular a compound of formula (I), a N-oxide form thereof, a pharmaceutically acceptable salt thereof or a solvate thereof, and (b) an anti-diabeticum, as a combined preparation for simultaneous, separate or sequential use in the treatment of a disease which can benefit from an elevated level of GLP-1 or DGAT inhibition, such as for example diabetes, in particular type II diabetes. The different drugs of such a combination or product may be combined in a single preparation together with pharmaceutically acceptable carriers or they may each be present in a separate preparation together with pharmaceutically acceptable carriers. Said anti-diabeticum which may be combined with a DGAT inhibitor according to the present invention may be a known anti-diabeticum such as for example metformin, glibenclamide, rosiglitazon, pioglitazon, repaglinide, glimepiride, acarbose, glicazide, glipizide, nateglinide, tolbutamide, a protein tyrosine phosphatase 1 inhibitor, or a 11-beta-hydroxysteroid dehydrogenase inhibitor.

d) a combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor. Phosphodiesterase (PDE) inhibitors, in particular PDE10A or PDE11A inhibitors, are known to be insulin secretagogues, and to enhance the signalling of GLP-1 by inhibition of the hydrolysis of cAMP.

Also, the combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a phosphodiesterase (PDE) inhibitor, in particular a PDE10A or PDE11A inhibitor, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said phosphodiesterase (PDE) inhibitor, in particular a PDE10A or PDE11A inhibitor, which may be combined with a DGAT inhibitor according to the present invention may be a known PDE inhibitor such as for example papaverine, PQ-10, dipyridamole, ibudilast or tadalafil.

e) a combination of a DGAT inhibitor, in particular a DGAT1 inhibitor, more in particular a compound of formula (I), a N-oxide form thereof, a pharmaceutically acceptable salt thereof or a solvate thereof, and an appetite suppressant.

Also, the combination of a DGAT inhibitor, in particular a DGAT1 inhibitor, more in particular a compound of formula (I), a N-oxide form thereof, a pharmaceutically acceptable salt thereof or a solvate thereof, and an appetite suppressant can be used as a medicine. The present invention also relates to a product containing (a) a DGAT inhibitor, in particular a DGAT 1 inhibitor, more in particular a compound of formula (I), a N-oxide form thereof, a pharmaceutically acceptable salt thereof or a solvate thereof, and (b) an appetite suppressant, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said appetite suppressants, which may be combined with a DGAT inhibitor according to the present invention may be a known appetite suppressant such as for example sibutramine and phentermine.

f) a combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action such as for example a CB 1 antagonist or inverse agonists.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-obesity drug with a CNS (central nervous system) mode of action, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-obesity drugs with a CNS (central nervous system) mode of action, which may be combined with a DGAT inhibitor according to the present invention may be a known a anti-obesity drug such as for example Rimonabant, orlistat, SLV-319, or MK-0364.

g) a combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug such as for example 3-hydroxy-3-methyl-glutaryl coenzyme A (HMG-CoA) reductase inhibitors, squalene synthase inhibitors, FXR (farnesoid X receptor) and LXR (liver X receptor) ligands, cholestyramine, fibrates, nicotinic acid and aspirin.

Also, the combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug can be used as a medicine. The present invention also relates to a product containing (a) a DGAT inhibitor, in particular a DGAT 1 inhibitor, more in particular a compound of formula (I), a N-oxide form thereof, a pharmaceutically acceptable salt thereof or a solvate thereof, and (b) an hypolipidemic drug, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said hypolipidemic drug which may be combined with a DGAT inhibitor according to the present invention may be a known hypolipidemic drug such as for example lovastatin, pravastatin, simvastatin, pravastatin, cerivastatin, mevastatin, velostatin, fluvastatin, dalvastatin, atorvastatin, rosuvastatin and rivastatin.

h) a combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate.

Also, the combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an agonist of peroxisome proliferator-activator receptor such as for example fenofibrate, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers.

i) a combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent.

Also, the combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent, can be used as a medicine. The present invention also relates to a product containing (a) a DGAT inhibitor, in particular a DGAT 1 inhibitor, more in particular a compound of formula (I), a N-oxide form thereof, a pharmaceutically acceptable salt thereof or a solvate thereof, and (b) an antihypertensive agent, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-hypertensive agent which may be combined with a DGAT inhibitor according to the present invention may be a known anti-hypertensive agent, e g loop diuretics such as ethacrynic acid, furosemide and torsemide, angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The following examples are intended to illustrate the present invention.

EXPERIMENTAL PART

Hereinafter, the term 'THF' means tetrahydrofuran, 'Et$_2$O' means diethyl ether, 'CH$_3$OH' means methanol, 'Pd(OH)$_2$' means palladium hydroxide, 'POCl$_3$' means phosphoric trichloride, 'EtOAc' means ethyl acetate, 'Na$_2$CO$_3$' means carbonic acid disodium salt, 'NaHCO$_3$' means carbonic acid monosodium salt, 'CH$_2$Cl$_2$' or 'DCM' means dichloromethane, 'CH$_3$CN' means acetonitrile, 'EtOH' means ethanol, 'DIPE' means diisopropyl ether, 'HBTU' means 1-[bis (di-methylamino)methylene]-1H-benzotriazoliumhexafluorophosphate(1-)3-oxide, 'DMF' means N,N-dimethylformamide, 'DMA' means N,N-dimethylacetamide, 'DIPEA' means N-ethyl-N-(1-methylethyl)-2-propanamine, 'HOBt' means 1-hydroxy-1H-benzotriazole, 'Na$_2$SO$_3$' means sulphurous acid, disodium salt, 'KOH' means potassium hydroxide, 'iPrOH' means 2-propanol, 'EDCI' means N'-(ethylcarbonimidoyl)-N,N-dimethyl-1,3-propanediamine monohydrochloride, 'HCTU" means 1-[bis (dimethyl-amino)methylene]-5-chloro-1H-benzotriazoliumhexafluorophosphate(1-) 3-oxide.

Isolute HM-N™ filter is a product of Argonaut, Foster City, Calif. 94404, USA, and is a short column comprising a modified form of diatomaceous earth that can remove water from a sample in combinatorial chemistry applications.

Extrelut™ is a product of Merck KgaA, Darmstadt, Germany, and is a short column comprising diatomaceous earth.

A number of compounds were purified by reversed phase high-performance liquid chromatography using one of the methods below (indicated in the compound procedure with method A, method B and method C). When necessary, these methods can be slightly adjusted by a person skilled in the art to obtain a more optimal result for the separation.

HPLC Method A

The product was purified by reversed-phase high-performance liquid chromatography (Shandon Hyperprep® C18 BDS (Base Deactivated Silica) 8 μm, 250 g, I.D. 5 cm). Two mobile phases were used (phase A: a 0.25% NH$_4$HCO$_3$ solution in water; phase B: CH$_3$CN). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% B in 20 minutes with a flow rate of 80 ml/min and hold for 4 minutes.

HPLC Method B

The product was purified by reversed-phase high-performance liquid chromatography (Shandon Hyperprep® C18 BDS (Base Deactivated Silica) 8 μm, 250 g, I.D. 5 cm). Two mobile phases were used (phase A: 90% of a 0.5% NH$_4$OAc solution in water+10% CH$_3$CN; phase B: CH$_3$CN). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% B in 20 minutes with a flow rate of 80 ml/min and hold for 4 minutes.

HPLC Method C

The product was purified by reversed phase high-performance liquid chromatography (Shandon Hyperprep® C18 BDS (Base Deactivated Silica) 8 μm, 250 g, I.D. 5 cm). Three mobile phases were used (phase A: 90% of a 0.5% NH$_4$OAc solution in water+10% CH$_3$CN; phase B: CH$_3$OH; phase C: CH$_3$CN). First, 75% A and 25% B with a flow rate of 40 ml/min was hold for 0.5 minutes. Then a gradient was applied to 50% B and 50% C in 41 minutes with a flow rate of 80 ml/min. Then a gradient was applied to 100% C in 20 minutes with a flow rate of 80 ml/min and hold for 4 minutes.

A. Preparation of the Intermediates

Example A1 a) Preparation of Intermediate 1

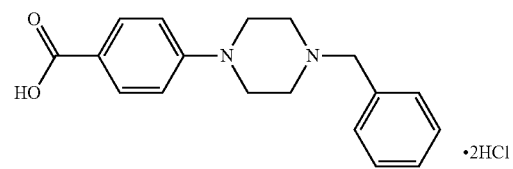

4-[4-(Phenylmethyl)-1-piperazinyl]benzoic acid, ethyl ester (58 g) was suspended in an aqueous HCl solution (430 ml, 2 N) and the reaction mixture was stirred for 17 hours at 100° C. Water was removed by evaporation, co-evaporated twice with dioxane, and the residue was suspended in Et₂O and filtered, yielding 55.4 g (84%) of intermediate 1 as blue solid (0.2HCl).

b) Preparation of Intermediate 2

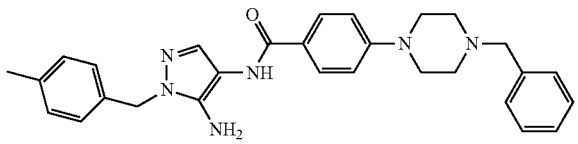 [SMILES: Cc1ccc(Cn2ncc(NC(=O)c3ccc(N4CCN(Cc5ccccc5)CC4)cc3)c2N)cc1]

1-[(4-Methylphenyl)methyl]-1H-pyrazole-4,5-diamine, sulfate (2:1) (1.48 g, 0.005887 mol), intermediate 1 (2.5 g, 0.00677 mol), HOBt (1.08 g, 0.007064 mol) and HBTU (2.68 g, 0.007064 mmol) were dissolved in DMF (22 ml). DIPEA (3 ml, 0.01766 mol) was added dropwise and the reaction mixture was stirred for 3 hours. To the reaction mixture was added an aqueous Na₂CO₃ solution (170 ml, half saturated) and EtOAc (35 ml). The formed precipitate was filtered off, washed with H₂O and EtOAc, and dried, yielding 1.93 g (68%) of intermediate 2 as pink powder.

c) Preparation of Intermediate 3

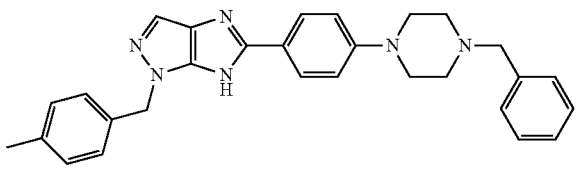 [SMILES: Cc1ccc(Cn2ncc3nc(-c4ccc(N5CCN(Cc6ccccc6)CC5)cc4)[nH]c32)cc1]

Intermediate 2 (1.9 g) was dissolved in dioxane (28 ml), and POCl₃ (28 ml) was added to the solution. The reaction mixture was heated for 90 minutes at 40° C., 90 minutes at 60° C. and for 2 hours at 80° C. Afterwards POCl₃ was distilled off and the residue was dissolved in dioxane (2 ml) and treated with an ice cold aqueous Na₂CO₃ solution (half saturated). The organic material was extracted with EtOAc (3×), dried (Na₂SO₄), filtered and the solvent was evaporated. The residue was purified by flash chromatography (Si 60, EtOAc/hexane gradient from 1:1 to 1:0) to yield 1.3 g (73%) of intermediate 3 as a yellow powder.

d) Preparation of Intermediate 4

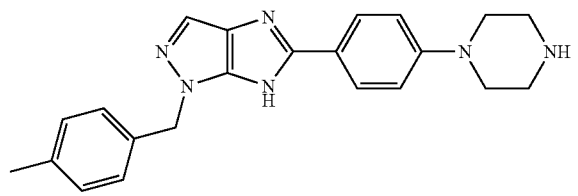 [SMILES: Cc1ccc(Cn2ncc3nc(-c4ccc(N5CCNCC5)cc4)[nH]c32)cc1]

Intermediate 3 (0.5 g) dissolved in CH₃OH (15 ml)/THF (2 ml) was hydrogenated for 17 hours in the presence of Pd(OH)₂ (0.1 g). The reaction mixture was filtered over Celite, washed with THF/CH₃OH (1/1) and evaporated to yield 0.396 g of intermediate 4 as a yellow powder.

Example A2 a) Preparation of Intermediate 5

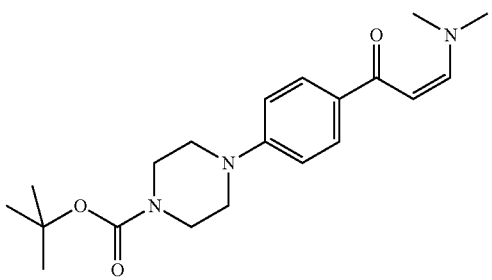 [SMILES: CN(C)/C=C\C(=O)c1ccc(N2CCN(C(=O)OC(C)(C)C)CC2)cc1]

A mixture of 4-(4-acetylphenyl)-1-piperazinecarboxylic acid, 1,1-dimethylethyl ester (12.16 g, 0.04 mol) and 1,1-dimethoxy-N,N-dimethylmethanamine (100 ml) was stirred and refluxed for 48 hours at 120° C. (oil bath). Subsequently, the mixture was cooled. The precipitate was filtered off, washed with DIPE and dried, yielding 8.7 g of intermediate 5.

b) Preparation of Intermediates 6 and 7

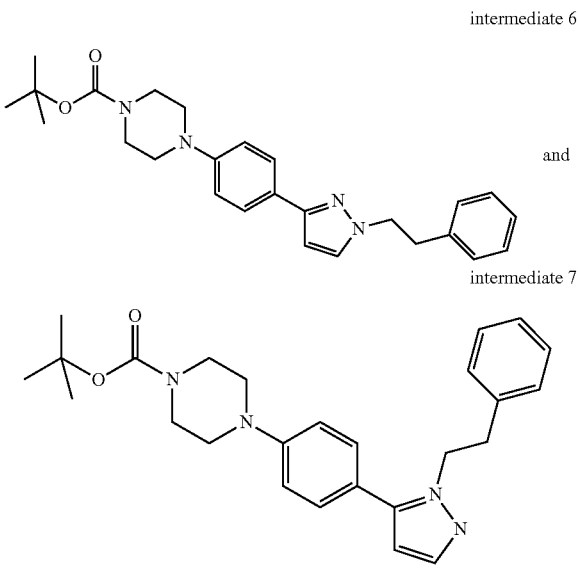

A mixture of sodium (0.096 g, 0.004 mol) and EtOH (10 ml, p.a.) was stirred at room temperature till a solution was obtained. (2-Phenylethyl)-hydrazine sulfate (0.468 g, 0.002 mol) was added and the mixture was stirred for 20 minutes. Intermediate 5 (0.539 g, 0.0015 mol) was added and the mixture was stirred for 144 hours at 85° C. The solvent was evaporated. The residue was stirred in H₂O (2 ml) and the product was extracted with CH₂Cl₂. The mixture was dried over an Isolute filter and the organic layer was evaporated. The residue was purified by HPLC Method A. Two different product fractions were collected and the solvent of each fraction was evaporated, yielding intermediate 6 and intermediate 7, residues were used as such in a next reaction.

c) Preparation of Intermediate 8

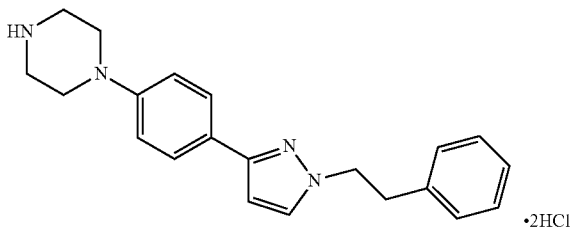 [SMILES: c1ccc(CCn2ccc(-c3ccc(N4CCNCC4)cc3)n2)cc1]

A mixture of intermediate 6 (0.091 g, 0.00021 mol), HCl/2-propanol (1.5 ml) and CH$_3$CN (3 ml) was stirred for 3 hours at room temperature. The solvent was evaporated (by a N$_2$ stream at 40° C.). The crude residue was dried, yielding 0.085 g of intermediate 8 (0.2HCl).

Example A3 a) Preparation of Intermediate 9

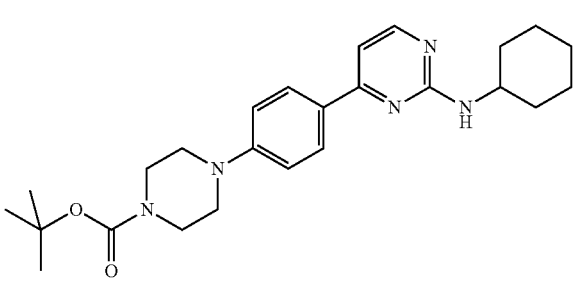 [SMILES: CC(C)(C)OC(=O)N1CCN(c2ccc(-c3ccnc(NC4CCCCC4)n3)cc2)CC1]

A mixture of sodium (0.036 g, 0.0015 mol) in EtOH (5 ml) was stirred at room temperature until the mixture became a solution. Subsequently N-cyclohexylguanidine sulfate (2:1) (0.285 g, 0.00075 mol) was added to the solution and the mixture was stirred for 15 minutes at room temperature. Intermediate 5 (0.539 g, 0.0015 mol) was added and the mixture was stirred for 188 hours at 85° C. The solvent was evaporated and the residue was stirred in H$_2$O (2 ml). The product was extracted with CH$_2$Cl$_2$. The mixture was filtered over an Isolute filter and the solvent was evaporated. The residue was purified by reversed phase HPLC. The pure fractions were collected and worked-up, yielding 0.33 g of intermediate 9, used as such in the next reaction.

b) Preparation of Intermediate 10

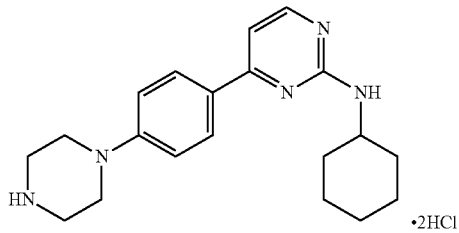 [SMILES: c1cc(-c2ccc(N3CCNCC3)cc2)nc(NC2CCCCC2)n1]

A mixture of intermediate 9 (0.330 g, 0.00075 mol), HCl/2-propanol (3 ml) and CH$_3$CN (6 ml) was stirred for 3 hours at room temperature. The solvent was evaporated under N$_2$ at 40° C. and the residue was dried, yielding 0.307 of intermediate 10 (0.2HCl).

Example A4 a) Preparation of Intermediate 11

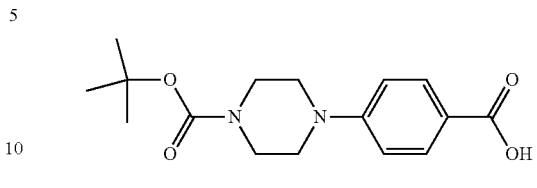

A mixture of 4-[4-(methoxycarbonyl)phenyl]-1-piperazinecarboxylic acid, 1,1-dimethylethyl ester (6.4 g, 0.0200 mol) in THF (200 ml) and CH$_3$OH (50 ml) was stirred at room temperature. 1N aqueous NaOH solution (200 ml, 0.200 mol) was added. The mixture was stirred for 4 hours at 50° C. 1N HCl (200 ml) was added and the product was precipitated. The product was filtered off, washed with water and dried, yielding 4.8 g of intermediate 11.

b) Preparation of Intermediate 12

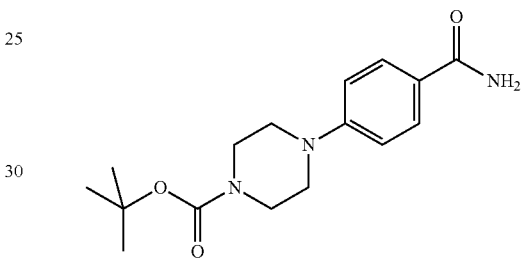

A mixture of intermediate 11 (6.7 g, 0.0220 mol), N'-(ethylcarbonimidoyl)-N,N-dimethyl-1,3-propanediamine, monohydrochloride (4.79 g, 0.0250 mol), 1-hydroxy-1H-benzotriazole (3.38 g, 0.0250 mol) and DMF was stirred at room temperature for 30 minutes. NH$_3$ was passed through the solution for 5 minutes (cooling with ice) and the mixture was stirred at room temperature for 18 hours. NH$_3$ was passed again for 5 minutes through the solution and the mixture was stirred for 2 hours at room temperature. H$_2$O (50 ml) was added and the product was precipitated. The product was filtered off, washed with water and dried, yielding 5.77 g (85%) of intermediate 12.

c) Preparation of Intermediate 13

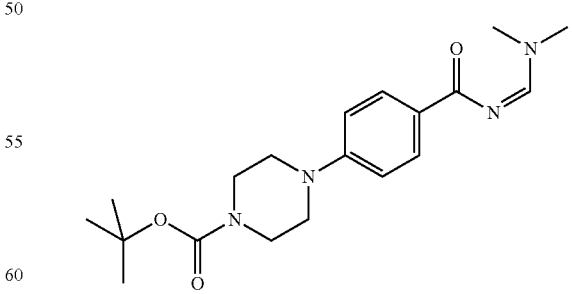

A mixture of intermediate 12 (1.5 g, 0.005 mol) and 1,1-dimethoxy-N,N-dimethylmethanamine (20 ml) was stirred for 5 hours at 120° C. The mixture was cooled. The product was precipitated, filtered off, washed (DIPE) and dried, yielding 1.170 g (65%) of intermediate 13.

d) Preparation of Intermediate 14

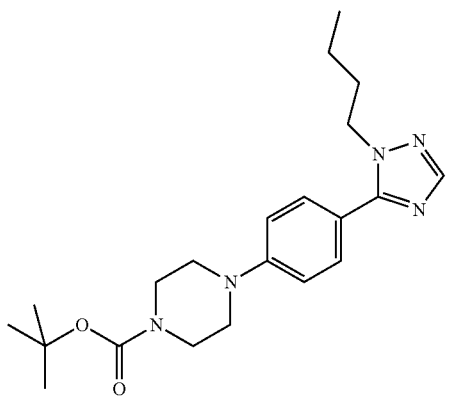 [SMILES: CCCCn1ncnc1-c1ccc(N2CCN(C(=O)OC(C)(C)C)CC2)cc1]

A mixture of intermediate 13 (0.180 g, 0.0005 mol), butylhydrazine, ethanedioate (1:1) (0.107 g, 0.0006 mol) and HOAc (4 ml) was stirred for 2 hours at 50° C. The solvent was evaporated (N₂ stream at 50° C.), yielding 0.192 g of intermediate 14 used as such in the next reaction step.

e) Preparation of Intermediate 15

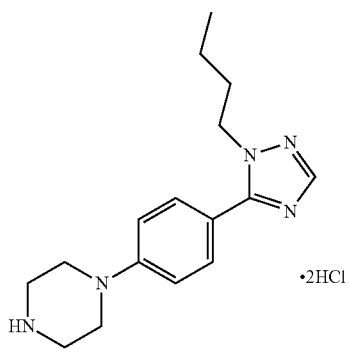 [SMILES: CCCCn1ncnc1-c1ccc(N2CCNCC2)cc1]

A mixture of intermediate 14 (0.192 g, 0.0005 mol), HCl/2-propanol (1.5 ml) and CH₃CN (3 ml) was stirred for 3 hours at room temperature. The solvent was evaporated (N₂ stream at 50° C.), yielding 0.179 g of intermediate 15 (0.2HCl) used as such in the next reaction (Example B2c).

Example A5 a) Preparation of Intermediate 16

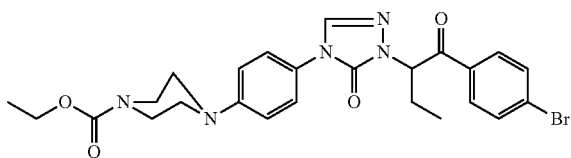 [SMILES: CCOC(=O)N1CCN(c2ccc(-n3cnn(C(CC)C(=O)c4ccc(Br)cc4)c3=O)cc2)CC1]

A mixture of 4-[4-(1,5-dihydro-5-oxo-4H-1,2,4-triazol-4-yl)phenyl]-1-piperazinecarboxylic acid, ethyl ester (0.032 mol), 2-bromo-1-(4-bromophenyl)-1-butanone (0.04 mol) and Na₂CO₃ (0.08 mol) in DMF (150 ml) was stirred and heated at 40° C. overnight. The mixture was filtered off and the filtrate was evaporated. The oily residue was stirred up in CH₂Cl₂/H₂O and separated. The organic layer was dried, filtered off and evaporated till a small volume. The oily residue was purified by column chromatography over silica gel (eluent: CH₂Cl₂/hexane/EtOAc 1/1/1). The pure fractions were collected and evaporated. The residue was purified again by column chromatography over silica gel (eluent: CH₂Cl₂/EtOAc/hexane 1/1/1). The pure fractions were collected and evaporated. The oily residue (12 g) was crystallized from Et₂O, yielding 9 g (52%) of intermediate 16.

b) Preparation of Intermediate 17

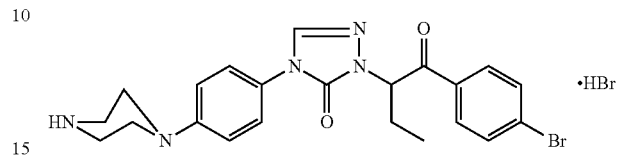

A mixture of Na₂SO₃ (1 g) in a 48% HBr solution (250 ml) was stirred for 10 minutes. Intermediate 16 (0.062 mol) was added. The mixture was stirred and refluxed for 5 hours. The mixture was stirred at room temperature overnight. The solvent was evaporated, yielding 21 g (72%) of intermediate 17 (.HBr).

Example A6 a) Preparation of Intermediate 18

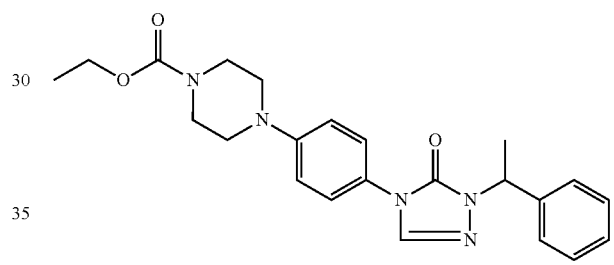

A mixture of 4-[4-(1,5-dihydro-5-oxo-4H-1,2,4-triazol-4-yl)phenyl]-1-piperazinecarboxylic acid, ethyl ester (0.0063 mol), (1-chloroethyl)benzene (0.0063 mol) and KOH (0.0063 mol) in DMF (30 ml) was stirred and heated overnight at 70° C., then the reaction mixture was cooled and poured out into ice/H₂O. The resulting precipitate was filtered off and washed with water. The solids were recrystallised from EtOAc/hexane and the pure product was collected, yielding 1 g (38%) of intermediate 18.

b) Preparation of Intermediate 19

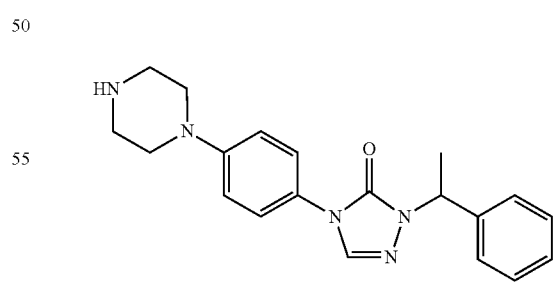

A mixture of intermediate 18 (6.08 g, 0.0150 mol) and NaHSO₃ (0.78 g, 0.0075 mol) in HBr (5 ml; 48%) was stirred and refluxed for 48 hours. Then the solvent was evaporated. The residue was washed with an alkaline aqueous solution. The aqueous layer was extracted with CH₂Cl₂ and the separated organic layer was dried, filtered and the solvent was evaporated. The crude residue was purified by column chromatography (eluent: first EtOAc and then CH₃OH (yielding intermediate 19)). The product fractions were collected and the solvent was evaporated. Yield: 1.5 g of intermediate 19 (29%; m.p.: 178-180° C.).

Example A7 a) Preparation of Intermediate 20

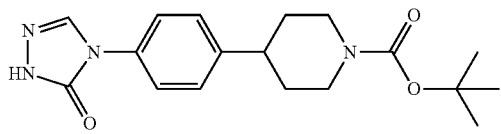 [SMILES: CC(C)(C)OC(=O)N1CCC(c2ccc(-n3cn[nH]c3=O)cc2)CC1]

Reaction under N₂ atmosphere. A solution of 4-(4-aminophenyl)-1-piperidine-carboxylic acid, 1,1-dimethylethyl ester (0.39 mol) in 1-methyl-2-pyrrolidinone (210 ml) was stirred and heated to 140° C. [(Dimethylamino)methylene]hydrazine-carboxylic acid, ethyl ester (0.465 mol) was added in four portions, each portion added after 20 minutes. The reaction mixture was stirred for 3 hours at 140° C. The mixture was allowed to cool to room temperature. H₂O (800 ml) was added and the resulting precipitate was filtered off and dried (vacuum, 50° C., 24 hours, under a gentle stream of N₂), yielding 134 g (100%) of intermediate 20.

b) Preparation of Intermediate 21

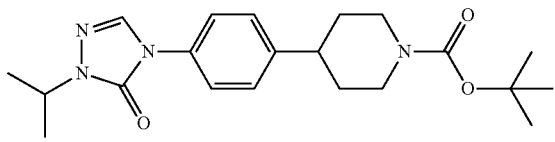 [SMILES: CC(C)n1ncn(-c2ccc(C3CCN(C(=O)OC(C)(C)C)CC3)cc2)c1=O]

A mixture of intermediate 20 (0.27 mol), 2-bromopropane (0.78 mol) and Cs₂CO₃ (0.39 mol) in DMA (580 ml) was stirred for 5 hours at 50° C., then overnight at room temperature. The mixture was poured out into water (1500 ml). CH₂Cl₂ (1 L) was added. The layers were separated. The organic layer was washed with water (5×1.0 L), dried (MgSO₄), filtered and the solvent was evaporated. The residue was stirred in 2-propanol and the resulting precipitate was filtered off and dried (vacuum, 50° C.), yielding 72.8 g of intermediate 21.

c) Preparation of Intermediate 22

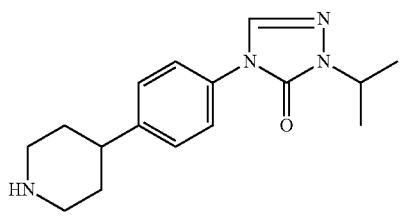 [SMILES: CC(C)n1ncn(-c2ccc(C3CCNCC3)cc2)c1=O]

A mixture of intermediate 21 (199 g, 0.51 mol) in CH₂Cl₂ (800 ml, c.p. (chemical pure)) was stirred at room temperature. HCl (1.18 mol, c.p.) was added and the reaction mixture was heated slowly to 40° C. The reaction mixture was stirred overnight at 40° C. HCl (50 ml, c.p.) was added and the mixture was stirred for 4 hours at 40° C., then allowed to cool to room temperature. The layers were separated. The water layer was alkalized (until pH=10). The resulting precipitate was filtered off, dissolved in CH₂Cl₂ and the organic solution was dried (MgSO₄), filtered and the solvent was evaporated. The residue was stirred in EtOAc, filtered off and dried (vacuum, 50° C.), yielding 103 g (70%) of intermediate 22.

Example A8 a) Preparation of Intermediate 23

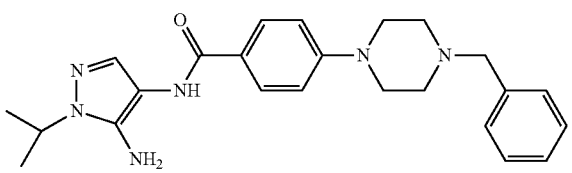 [SMILES: CC(C)n1ncc(NC(=O)c2ccc(N3CCN(Cc4ccccc4)CC3)cc2)c1N]

1-(1-Methylethyl)-1H-pyrazole-4,5-diamine, sulfate (2:1) (46 g, 0.1928 mol), intermediate 1 (89 g, 0.241 mol), 6-chloro-1-hydroxy-1H-benzotriazole (3.3 g, 0.01928 mol) and HCTU (95.7 g, 0.2314 mol) were dissolved in DMF (530 ml). To the reaction mixture was added DIPEA (165 ml, 0.964 mol) within 5 minutes and the mixture was stirred for 17 hours at room temperature. To the reaction mixture was added an aqueous Na₂CO₃ (half saturated) solution and the organic material was extracted with EtOAc, dried (Na₂SO₄), filtered and the solvent was evaporated. The crude was suspended in Et₂O and filtered, yielding 60.4 g (75%) of intermediate 23 as pink powder.

b) Preparation of Intermediate 24

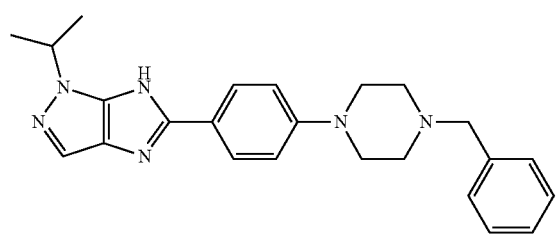 [SMILES: CC(C)n1ncc2nc(-c3ccc(N4CCN(Cc5ccccc5)CC4)cc3)[nH]c21]

Intermediate 23 (30 g) was dissolved in dioxane (250 ml). POCl₃ (250 ml) was added to the solution. The reaction mixture was heated for 1 hour at 40° C. and subsequently dioxane (100 ml) was added and heating was continued for 2 hours at 80° C. Afterwards POCl₃ was distilled off and the residue was dissolved in dioxane (100 ml) and treated with an ice cold aqueous Na₂CO₃ (half saturated) solution. The organic material was extracted with EtOAc (3×), dried (Na₂SO₄), filtered and the solvent was evaporated. The residue was purified by flash chromatography (Si 60, EtOAc). The most clean fractions were suspended in Et₂O and filtered, yielding 16.88 g (59%) of intermediate 24 as a brown powder.

c) Preparation of Intermediate 25

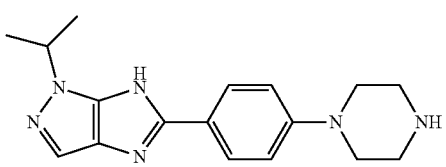 [SMILES: CC(C)n1ncc2nc(-c3ccc(N4CCNCC4)cc3)[nH]c21]

Intermediate 24 (16.8 g) was dissolved in CH₃OH (330 ml). The solution was hydrogenated for 6 hours in the presence of Pd(OH)₂ (8.4 g). After filtration over Celite, the solvent was evaporated, yielding 13.28 g of intermediate 25 as a yellow powder.

Example A9 a) Preparation of Intermediate 26

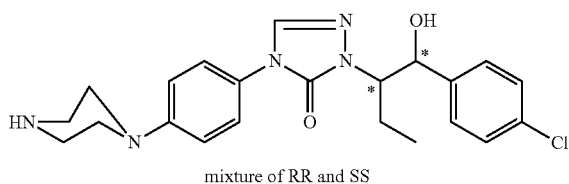 [SMILES: CCC(C(O)c1ccc(Cl)cc1)n1ncn(-c2ccc(N3CCNCC3)cc2)c1=O]
mixture of RR and SS (+-)-2-[1-(4-chlorobenzoyl)propyl]-2,4-dihydro-4-[4-(1-piperazinyl)phenyl]-3H-1,2,4-triazol-3-one dihydrochloride.monohydrate (0.0087 mol) in CH₃OH (100 ml) and CH₃OH/NH₄OH (10 ml) was cooled till −20° C. and the mixture was warmed-up slowly to room temperature. The mixture was poured into H₂O and the solid was filtered off. The precipitate was crystallized from 2-propanol. The product was dried in vacuo for 24 hours at 100° C. Yield: 2.9 g of intermediate 26 (78%).

Example A10 a) Preparation of Intermediate 27

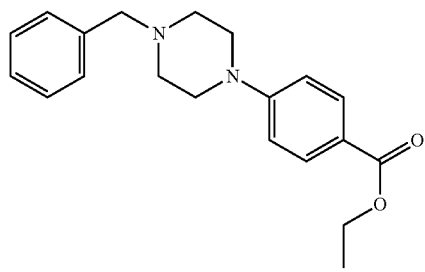 [SMILES: CCOC(=O)c1ccc(N2CCN(Cc3ccccc3)CC2)cc1]

A solution of ethyl 4-fluorobenzoic acid ester (17.51 g; 0.104 mol) and 1-benzyl-piperazine (36.83 g; 0.209 mol) in DMA (100 ml) was stirred and refluxed for 15 hours. The reaction mixture was allowed to reach room temperature and poured into ±750 ml stirring H₂O. The solid part was filtered off, washed with plenty of water, dried for 15 hours at 50° C. in vacuo, recrystallized with 150 ml iPrOH, filtered off, washed with iPrOH and dried for 48 hours at 50° C. in vacuo, yielding 27.11 g of intermediate 27 (80%).

b) Preparation of Intermediate 28

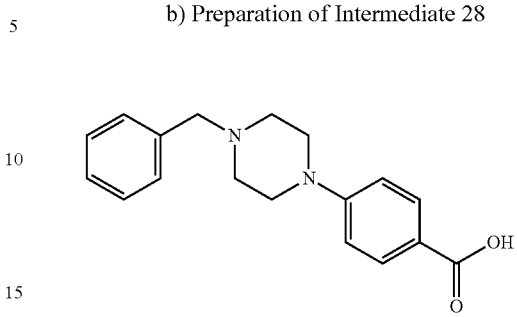

Intermediate 27 (14.001 g; 0.0432 mol) was added to sodium hydroxide (86 ml; 0.086 mol) while stirring. 1,4-Dioxane (175 ml) was added gently to the stirred reaction mixture. A turbid mixture was formed. The mixture was heated at 45° C. and the product was dissolved in 30 minutes. After heating for 20 hours, the reaction mixture was cooled off in icewater and HCl 1M (86 ml) was added. The product was filtered off, washed with water and dried in vacuo at 50° C., yielding 12.16 g of intermediate 28 (95%).

c) Preparation of Intermediate 29

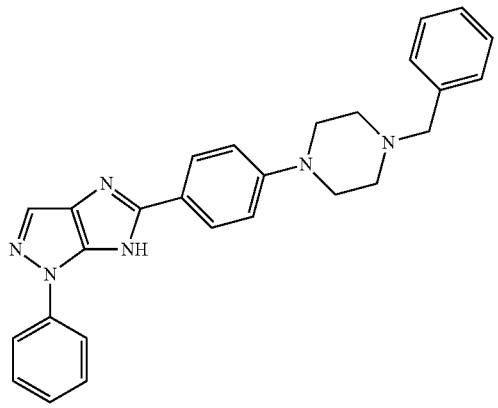 [SMILES: c1ccc(CN2CCN(c3ccc(-c4nc5cnn(-c6ccccc6)c5[nH]4)cc3)CC2)cc1]

POCl₃ (5 ml; 53.642 mmol) was added to intermediate 28 (405.344 mg; 1.368 mmol) and 1-phenyl-1H-Pyrazole-4,5-diamine dihydrochloride (338 mg; 1.368 mmol). The fine suspension was stirred overnight at 100° C. The reaction mixture was poured unto ice and stirred for an hour. While cooling on an ice bath, some DCM was added and made alkaline with 50% NaOH. The resulting salt was filtered off and the DCM layer was separated. The aqueous layer was mixed with the salt and extracted twice with DCM. The combined DCM layers were dried (MgSO₄), filtered and evaporated. The residue was purified by reversed phase high-performance liquid chromatography (Shandon Hyperprep® C18 BDS (Base Deactivated Silica) 8 μm, 250 g, I.D. 5 cm). A gradient with 2 mobile phases was applied. Phase A: 90% of a 0.5% NH₄OAc solution in water+10% CH₃CN; phase B: CH₃CN). The desired fractions were collected and the eluent was evaporated. The residue was neutralized with NaHCO₃, extracted with DCM and dried (MgSO$_4$), filtered and the solvent was evaporated, yielding 254 mg of intermediate 29 (43%).

d) Preparation of Intermediate 30

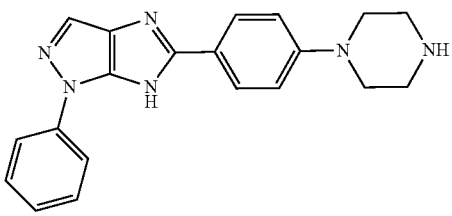 [SMILES: c1ccc(-n2ncc3nc(-c4ccc(N5CCNCC5)cc4)[nH]c32)cc1]

Intermediate 29 (1.279 g; 2.943 mmol) was hydrogenated with Pd/C 10% (0.5 g) in methanol (150 ml) under N$_2$ atmosphere. The reaction mixture was stirred at 25° C. under H$_2$ atmosphere until 1 eq. hydrogen was absorbed. The catalyst was filtered off over dicalite and the residue was evaporated, yielding 959 mg of intermediate 30 (95%).

Example A11

Preparation of Intermediate 31 and Intermediate 32

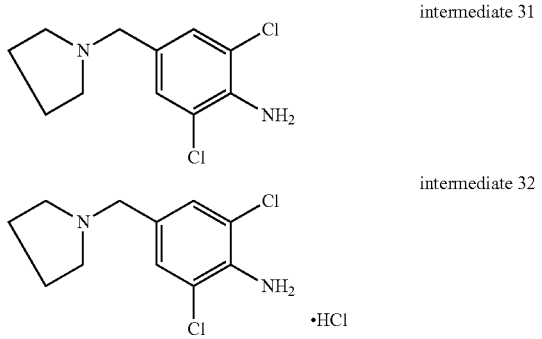

intermediate 31 intermediate 32

2,6-Dichloro-4-chloromethyl-phenylamine (11 g, 0.0445 mol) was added portionwise to a stirring solution of pyrrolidine (15.84 g, 0.223 mol) in CH$_3$CN (250 ml). The reaction mixture was placed in a water bath (exothermic reaction). The solvent was evaporated and the residue was dissolved in CH$_2$Cl$_2$ (150 ml) and a 50% saturated NaHCO$_3$ solution (100 ml). The mixture was stirred for 15 minutes. The organic layer was separated, dried (MgSO$_4$), filtered and the solvent was evaporated and co-evaporated with toluene. The oily residue (11.46 g) was stirred in DIPE (30 ml) for 15 minutes and then the DIPE was evaporated again. The residue was combined with 2.65 g of another batch and the total amount of crude product was purified by column chromatography over silicagel (eluent: CH$_2$Cl$_2$/MeOH 95/5). The pure fractions were combined and the solvent was evaporated and co-evaporated with toluene. The residue was stirred in DIPE (25 ml). The DIPE was decanted from the solid, yielding a DIPE layer (*) and a solid. The remaining DIPE on the solid was evaporated and the solid was dried (50° C., in vacuo), yielding 2.75 g of intermediate 31 (28.18%). The impure fractions from the column were combined and the solvent was evaporated and co-evaporated with toluene. The residue (7.45 g) was dis-solved in DIPE (20 ml) and 6N HCl in 2-propanol (5 ml) was added while the mixture was stirred vigorously. A yellowish oil was formed that became solid after continuous stirring. The solid was filtered off and washed with DIPE, yielding a filtrate (*) and a solid. The solid was dried (50° C., in vacuo). Yield: 5.19 g of intermediate 32 (41%; .HCl). The filtrate (*) and the DIPE layer (*) were combined and the solvent was evaporated. The residue (2.59 g) was dissolved in CH$_2$Cl$_2$ and NaHCO$_3$ in H$_2$O. The layers were separated and the organic layer was dried (MgSO$_4$), filtered and the solvent was partially evaporated. The concentrated solution was re-purified over silicagel (eluent: CH$_2$Cl$_2$/MeOH 95/5). The pure fractions were collected and the solvent was evaporated and co-evaporated with toluene. The residue was dried (50° C., 18 hours, in vacuo). Yield: 1.85 g of intermediate 31 (17%).

Example A12

Preparation of Intermediate 33

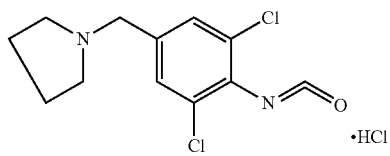 [SMILES: O=C=Nc1c(Cl)cc(CN2CCCC2)cc1Cl ; Cl]

HCl 1M in Et$_2$O (10.32 ml; 0.0206 mol) was added to a stirring solution of intermediate 31 (4.6 g; 0.0188 mol) in CH$_3$CN p.a. dried on molecular sieves (75 ml) and CH$_2$Cl$_2$ p.a (10 ml). Stirring was continued for 1 hour. A precipitate was formed. The reaction mixture was cooled on an ice-bath, and phosgene 20% in toluene (14 ml) was added. The reaction mixture was stirred further for 3 hours. Extra phosgene 20% in toluene (7 ml) was added, and the reaction mixture was stirred further at room temperature for 18 hours. The product was filtered off, washed with CH$_3$CN (3×) and dried at 50° C. [vacuum, 1 hour], yielding 5.45 g of intermediate 33 (94%).

Example A13 a) Preparation of Intermediate 34

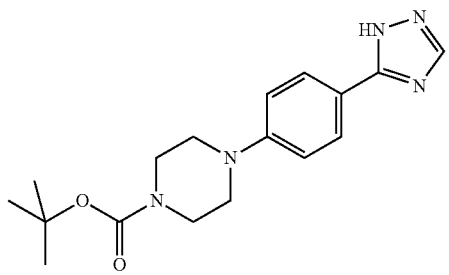 [SMILES: CC(C)(C)OC(=O)N1CCN(c2ccc(-c3ncn[nH]3)cc2)CC1]

Hydrazine monohydrate (1.75 g; 35 mmol) was added to 25 ml acetic acid (exothermic). This mixture was added dropwise to intermediate 13 and 50 ml of acetic acid at room temperature. The mixture was stirred for 40 hours. The solvent was evaporated. The residue was stirred in H$_2$O, treated with Na₂CO₃ and extracted with CH₂Cl₂. The organic layer was dried, filtered and evaporated, yielding 5.6 g of intermediate 34.

b) Preparation of Intermediate 35

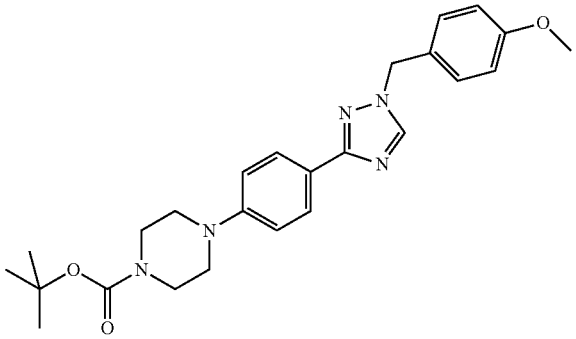 [SMILES: COc1ccc(Cn2cnc(-c3ccc(N4CCN(C(=O)OC(C)(C)C)CC4)cc3)n2)cc1]

A mixture of intermediate 34 (0.987 g; 3 mmol) and 15 ml of DMF was stirred at room temperature. NaH 60% (0.131 g; 3.3 mmol) was added and the mixture was stirred for 15 minutes at room temperature. 1-(Bromomethyl)-4-methoxybenzene (0.475 ml; 3.3 mmol) and 5 ml of DMF was added dropwise over 15 minutes. The mixture was stirred at room temperature for 18 hours. 0.026 g of NaH 60% and 0.095 ml of 1-(bromo-methyl)-4-methoxybenzene were added and the mixture was stirred for 3 hours. The solvent was evaporated and the residue was stirred in water and extracted with CH₂Cl₂. The organic layer was dried, filtered and evaporated. The residue was purified and the regioisomers were separated with HPLC method A. The desired fraction was collected and the solvent was evaporated, yielding 0.699 of intermediate 35.

c) Preparation of Intermediate 36

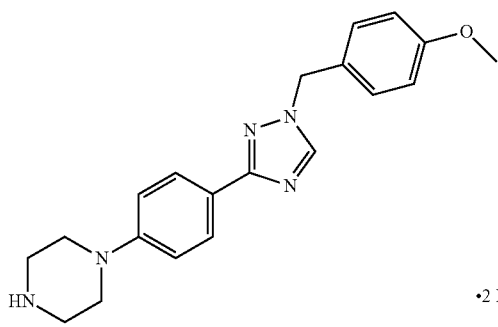

•2 HCl

A mixture of intermediate 35 (0.649 g; 1.4 mmol), 5 ml of HCl/iPrOH and 10 ml of CH₃CN was stirred at room temperature for 3 hours. A solid precipitated and the solvent was evaporated. The residue was dried, yielding 0.748 g of intermediate 36.

Example A14 a) Preparation of Intermediate 38

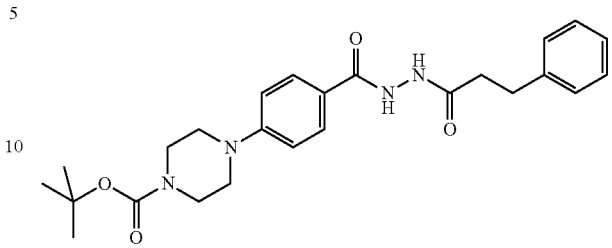

A mixture of intermediate 11 (0.918 g; 3 mmol), EDCI (0.843 g; 4.4 mmol), HOBt (0.594 g; 4.4 mmol) and 10 ml of DMF was stirred at room temperature for 15 minutes. Benzenepropanoic acid hydrazide (1.045 g; 6.4 mmol) was added. The mixture was stirred at room temperature for 18 hours. The solvent was evaporated. The residue was stirred in water and extracted with CH₂Cl₂. The organic layer was dried, filtered and evaporated. The mixture was purified with HPLC method C. The pure fraction were collected and the solvent was evaporated. The residue was dried, yielding 0.941 g of intermediate 38.

b) Preparation of Intermediate 39

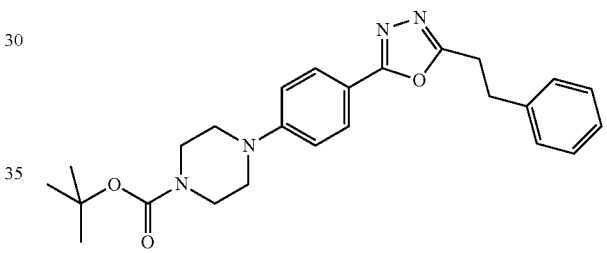

A mixture of intermediate 38 (0.863 g; 1.9 mmol) and 15 ml of THF was stirred at room temperature. 7-Oxa-4-thia-3,5-diazaoctane-2,4-diaminium, 3,3-diethyl-6-oxo-, inner salt 4,4-dioxide (0.715 g; 3 mmol) (Burgess' reagent) was added. The mixture was stirred at 60° C. for 3 hours. The solvent was evaporated. The residue was stirred in 2 ml of water and extracted with CH₂Cl₂. The mixture was filtered over Isolute filter and the organic layer was evaporated. The residue was filtered over silicagel using a mixture of CH₂Cl₂ and CH₃OH (97/3 by volume) as eluent. The pure fraction were collected and the solvent was evaporated. The residue was dried, yielding 0.690 g of intermediate 39.

c) Preparation of Intermediate 40

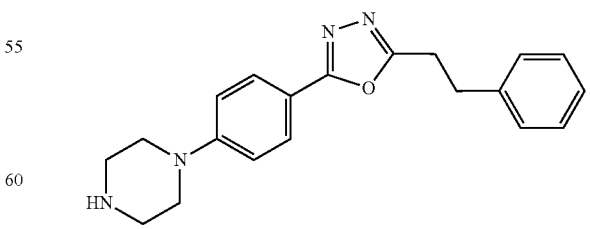

A mixture of intermediate 39 (0.690 g; 1.59 mmol) and 15 ml of CH₂Cl₂ was stirred at room temperature. 1.5 ml of CF₃COOH was added. The mixture was stirred for 3 hours. The solvent was evaporated at 50° C. by a nitrogen stream. The residue was stirred in CH₂Cl₂ and washed with water and NaHCO₃. The mixture was dried over Isolute filter and the organic layer was evaporated. The residue was dried, yielding 0.439 g of intermediate 40.

Example A15 a) Preparation of Intermediate 41

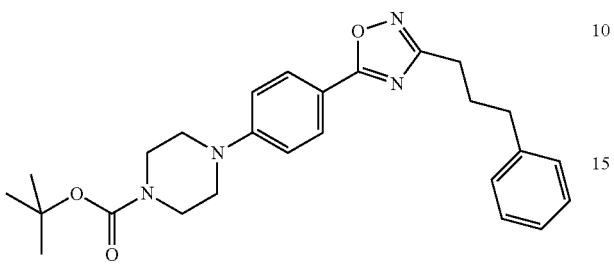

A mixture of N-hydroxybenzenebutanimidamide (0.713 g; 4 mmol), NaH 60% (0.200 g; 5 mmol) and 20 ml of THF was stirred at room temperature. 1,1-dimethylethyl 4-[4-(methoxycarbonyl)phenyl]-1-piperazinecarboxylic acid ester (0.640 g; 2 mmol) was added portionwise over 15 minutes. The mixture was stirred and refluxed for 18 hours. The solvent was evaporated. The residue was stirred in water and extracted with CH₂Cl₂. The organic layer was dried, filtered and evaporated. The residue was filtered over silicagel using a mixture of CH₂Cl₂ and CH₃OH (99/1 by volume) as eluent. The desired fractions were collected and the solvent was evaporated, yielding 0.206 of intermediate 41.

b) Preparation of Intermediate 42

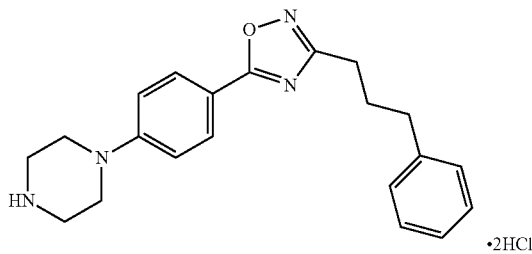 [SMILES: c1ccc(CCCc2noc(-c3ccc(N4CCNCC4)cc3)n2)cc1]

•2HCl

A mixture of intermediate 41 (0.206 g; 0.46 mmol), 4 ml of HCl/iPrOH and 8 ml of CH₃CN was stirred at room temperature for 5 hours. The product was precipitated, filtered off and dried, yielding 0.104 g of intermediate 42.

Example A16 a) Preparation of Intermediate 43

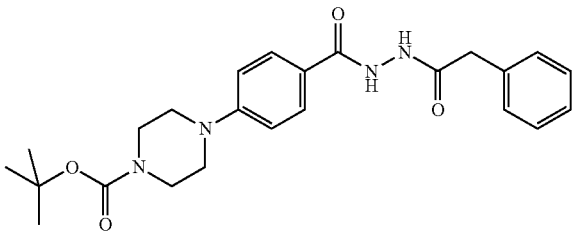 [SMILES: CC(C)(C)OC(=O)N1CCN(c2ccc(C(=O)NNC(=O)Cc3ccccc3)cc2)CC1]

A mixture of intermediate 11 (0.918 g; 3 mmol), EDCI (0.843 g; 4.4 mmol), HOBt (0.594 g; 4.4 mmol) and 10 ml of DMF was stirred at room temperature for 15 minutes. Phenylacetic acid hydrazide (1 g; 6.65 mmol) was added. The mixture was stirred at room temperature for 18 hours. The solvent was evaporated. The residue was stirred in water and extracted with CH₂Cl₂. The organic layer was dried, filtered and evaporated. The residue was purified by reversed-phase high-performance liquid chromatography (Shandon Hyperprep® C18 BDS (Base Deactivated Silica) 8 μm, 250 g, I.D. 5 cm). A gradient with the following mobile phases was applied. Phase A: a 0.25% NH₄HCO₃ solution in water; phase B (optional): CH₃OH; phase C: CH₃CN). The desired fractions were collected and the solvent was evaporated. The residue was dried, yielding 0.802 g of intermediate 43.

b) Preparation of Intermediate 44

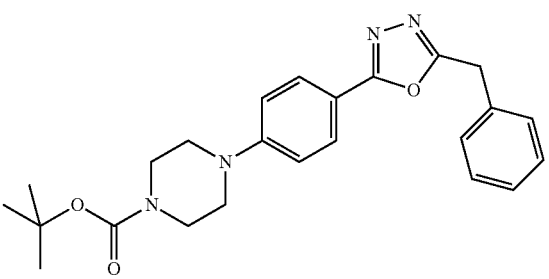 [SMILES: CC(C)(C)OC(=O)N1CCN(c2ccc(-c3nnc(Cc4ccccc4)o3)cc2)CC1]

A mixture of intermediate 43 (0.263 g; 0.6 mmol) and 10 ml of THF was stirred at room temperature. 7-Oxa-4-thia-3,5-diazaoctane-2,4-diaminium, 3,3-diethyl-6-oxo-, inner salt 4,4-dioxide (0.214 g; 0.9 mmol) (Burgess' reagent) was added at once. The mixture was stirred at 60° C. for 3 hours. The solvent was evaporated. The residue was stirred in 2 ml of water and extracted with CH₂Cl₂. The mixture was dried over Isolute filter and the organic layer was evaporated. The residue was filtered over silicagel using a mixture of CH₂Cl₂ and CH₃OH (96/4 by volume) as eluent. The pure fraction were collected and the solvent was evaporated. The residue was dried, yielding 0.214 g of intermediate 44.

c) Preparation of Intermediate 45

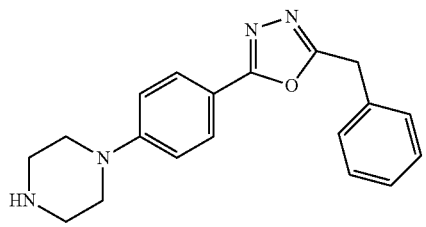 [SMILES: c1ccc(Cc2nnc(-c3ccc(N4CCNCC4)cc3)o2)cc1]

A mixture of intermediate 44 (0.172 g; 0.41 mmol) and 8 ml of CH₂Cl₂ was stirred at room temperature for 5 minutes. 0.8 ml of CF₃COOH was added. The mixture was stirred at room temperature for 18 hours. The solvent was evaporated at 50° C. by a nitrogen stream. The residue was stirred in water, treated with NaHCO₃ and extracted with CH₂Cl₂. The organic layer was evaporated and dried, yielding 0.127 g of intermediate 45.

Example A17 a) Preparation of Intermediate 46 and Intermediate 47

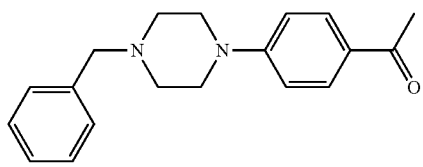
intermediate 46

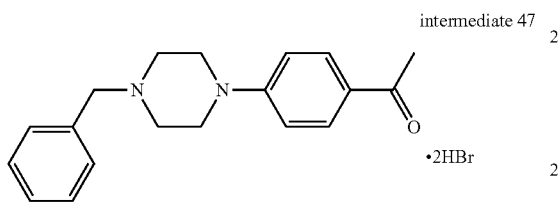
intermediate 47
·2HBr

A mixture of 1-[4-(1-piperazinyl)phenyl]ethanone (25 g; 0.122 mol), Na$_2$CO$_3$ (14.269 g; 0.135 mol) and 150 ml of THF was stirred at room temperature. Bromomethyl-benzene (16.102 ml; 0.135 mol) and 50 ml THF was added dropwise over 30 minutes at room temperature. The mixture was stirred at room temperature for 18 hours. The solvent was evaporated. The residue was stirred in water and extracted with CH$_2$Cl$_2$. The organic layer was dried, filtered and evaporated. The residue was stirred in DIPE. The product was filtered off and dried, yielding 31.5 g of intermediate 46.

10 g of intermediate 46 was dissolved in 50 ml acetonitrile. Salt was formed by adding HBr 48%. The salt was precipitated, filtered off and dried, yielding 5.5 g of intermediate 47.

b) Preparation of Intermediate 48

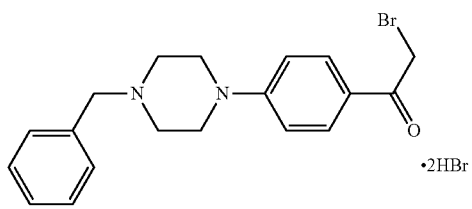 [SMILES: O=C(CBr)c1ccc(N2CCN(Cc3ccccc3)CC2)cc1]
·2HBr

A mixture of intermediate 47 (3.94 g; 0.00864 mol) and 75 ml of HBr/CH$_3$COOH was stirred at room temperature. Br$_2$ (0.487 ml; 0.0095 mol) was added and the mixture was stirred at room temperature for 18 hours. The mixture was poured in ice water. The product was filtered off, washed with DIPE and dried, yielding 3.69 g of intermediate 48 (80%).

c) Preparation of Intermediate 49

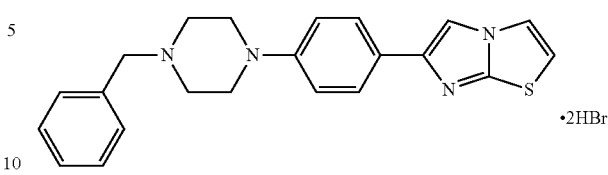
·2HBr

A mixture of intermediate 48 (1.069 g; 0.002 mol), 2-thiazolamine (0.2 g; 0.002 mol) and 25 ml of ethanol was stirred at 80° C. for 18 hours. The mixture was cooled. The product was filtered off, washed with ethanol and DIPE and dried, yielding 0.794 g of intermediate 49.

d) Preparation of Intermediate 50

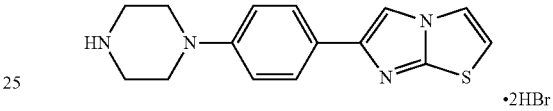
·2HBr

Intermediate 49 (0.661 g; 0.00123 mol) was stirred in water, treated with Na$_2$CO$_3$ and extracted with CH$_2$Cl$_2$. The organic layer was dried, filtered and evaporated. The residue and 30 ml of dichloroethane was stirred at room temperature. 1-Chloroethyl carbonochloridic acid ester (0.161 ml; 0.00148 mol) was added and the mixture was stirred at 85° C. for 2 hours. The solvent was evaporated. The residue was dissolved in methanol and stirred at 85° C. in a closed vessel for 7 days. The solvent was evaporated, yielding 0.357 g of intermediate 50.

Example A18 a) Preparation of Intermediate 51

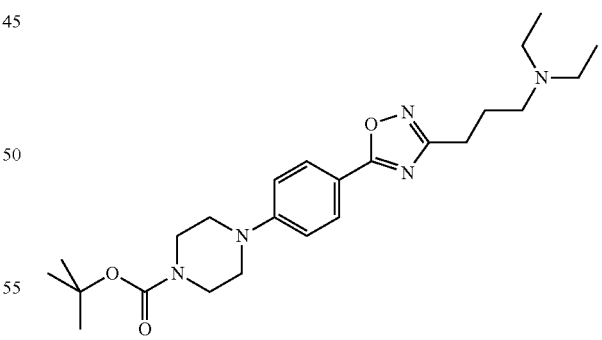

A mixture 4-(diethylamino)-N-hydroxybutanimidamide (0.693 g; 4 mmol), NaH 60% (0.160 g; 4 mmol) and 20 ml of THF was stirred at room temperature. 1,1-Dimethyl-ethyl 4-[4-(methoxycarbonyl)phenyl]-1-piperazinecarboxylic acid ester (0.640 g; 2 mmol) was added portionwise over 15 minutes. The mixture was stirred and refluxed for 144 hours. The solvent was evaporated. The residue was stirred in water and extracted with CH$_2$Cl$_2$. The organic layer was dried, filtered and evaporated. The residue was purified with HPLC method C. The pure fraction were collected and the solvent was evaporated. The residue was dried, yielding 0.161 g of intermediate 51.

b) Preparation of Intermediate 52

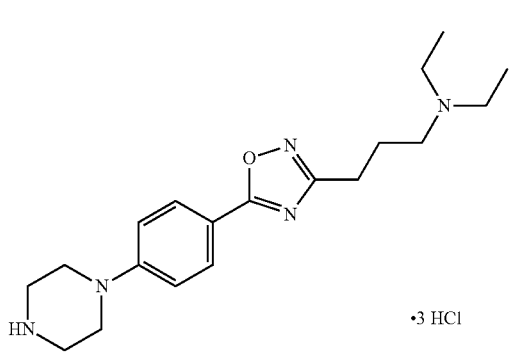 [SMILES: CCN(CC)CCCc1noc(-c2ccc(N3CCNCC3)cc2)n1]

A mixture of intermediate 51 (0.161 g; 0.36 mmol), 2.5 ml of HCl/iPrOH and 5 ml of CH$_3$CN was stirred at room temperature for 3 hours. The solvent was evaporated, yielding 0.163 of intermediate 52.

Example A19 a) Preparation of Intermediate 53

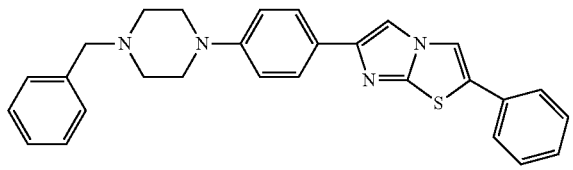 [SMILES: c1ccc(CN2CCN(c3ccc(-c4cn5cc(-c6ccccc6)sc5n4)cc3)CC2)cc1]

A mixture of intermediate 48 (2.17 g; 0.004 mol), 5-phenyl-2-thiazolamine (2.115 g; 0.012 mol) and 50 ml of ethanol was stirred at 75° C. for 18 hours. The product was precipitated, filtered off, washed with DIPE and dried, yielding 1.8 g of intermediate 53.

b) Preparation of Intermediate 54

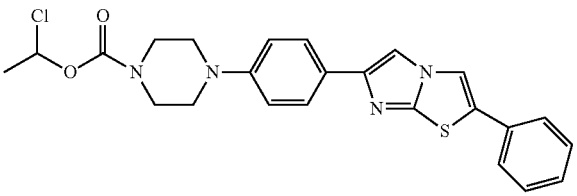 [SMILES: CC(Cl)OC(=O)N1CCN(c2ccc(-c3cn4cc(-c5ccccc5)sc4n3)cc2)CC1]

1-Chloroethyl carbonochloridic acid ester (1.734 ml; 0.0159 mol) was added to a stirred mixture of intermediate 53 (1.79 g; 0.00397 mol), 1.522 ml of DIPEA and 30 ml of 1,2-dichloroethane. The reaction mixture was stirred and refluxed for 2 hours. The solvent was evaporated and three times co-evaporated with xylene, yielding intermediate 54, a residue used as such in the next reaction.

c) Preparation of Intermediate 55

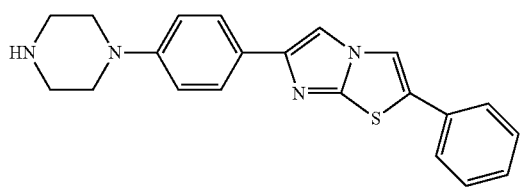 [SMILES: c1ccc(-c2cn3cc(-c4ccc(N5CCNCC5)cc4)nc3s2)cc1]

A mixture of intermediate 54 (1.821 g; 0.0039 mol) and 25 ml of methanol was refluxed for 18 hours. 2 ml of HBr 48% was added. The reaction mixture was stirred, refluxed for 83 hours and poured into 100 ml H$_2$O containing 2 g NaHCO$_3$. After stirring for 15 minutes, the product was filtered off, washed with H$_2$O three times and dried at 50° C. (vacuum), yielding 0.5 g of intermediate 55 (36%).

Example A20 a) Preparation of Intermediate 56

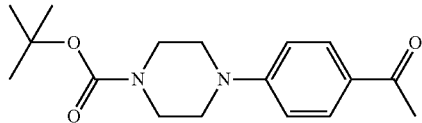

C,C'-bis(1,1-dimethylethyl)dicarbonic acid ester (60.1 g; 0.276 mol) was added in small portions to a stirred solution of 1-[4-(1-piperazinyl)phenyl]ethanone (50.0 g; 0.245 mol) in dry CH$_2$Cl$_2$ (400 ml) at room temperature. The obtained solution was stirred for 0.5 hour. The solvent was removed in vacuum. The residue was purified by chromatography (eluent: chloroform), yielding 40.7 g (55%) of intermediate 56.

b) Preparation of Intermediate 57

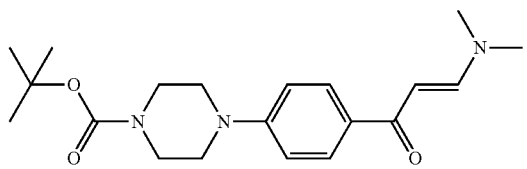 [SMILES: CN(C)/C=C/C(=O)c1ccc(N2CCN(C(=O)OC(C)(C)C)CC2)cc1]

Intermediate 56 (78.4 g; 0.258 mol) was dissolved in 1,1-dimethoxy-N,N-dimethyl-methanamine (300 ml; 2.24 mol) and obtained solution was refluxed for 20 hours. Then diisopropyl ether (150 ml) was added to the hot solution and obtained mixture was allowed to cool. The formed crystals were filtered off and washed with diisopropyl ether, yielding intermediate 57.

The filtrate was concentrated in vacuum to remove diisopropyl ether followed by reflux of the residue for 10 hours. Then diisopropyl ether (150 ml) was added, the mixture was allowed to cool and the formed crystals were filtered off to give an additional amount of intermediate 57. The total yield of intermediate 57 is 67.5 g (73%).

c) Preparation of Intermediate 58

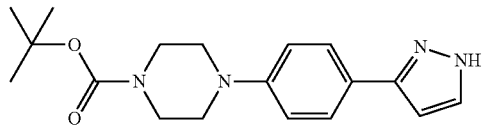 [SMILES: CC(C)(C)OC(=O)N1CCN(c2ccc(-c3cc[nH]n3)cc2)CC1]

Hydrazine monohydrate (7.5 ml; 115.0 mmol) was added to a solution of intermediate 57 (13.8 g; 38.4 mmol) in ethanol (100 ml) and resulting solution was refluxed for 5 hours. Then water (100 ml) was added to the hot solution, after that ethanol (about 50 ml) was removed by distillation. The mixture was allowed to cool to room temperature and formed crystals were filtered off, washed with water and dried on air, yielding 11.5 g (91%) of intermediate 58.

d) Preparation of Intermediate 59

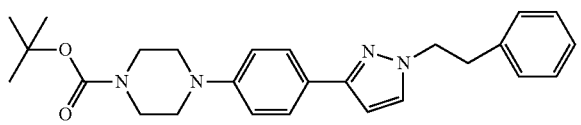 [SMILES: CC(C)(C)OC(=O)N1CCN(c2ccc(-c3ccn(CCc4ccccc4)n3)cc2)CC1]

Intermediate 58 (15.52 g; 0.0473 mol) was dissolved in dry DMF (100 ml), then NaH 60% (4.16 g; 0.1040 mol) was added and the reaction mixture was stirred at room temperature for 0.5 hours. Subsequently, 2-bromoethylbenzene (14.25 ml; 0.1040 mol) was added and the reaction mixture was stirred for 20 hours more at room temperature. The mixture was poured out into water (300 ml) and diluted with hexane (100 ml). The organic layer was washed with water three times and the organic layer was separated. The product was filtered off and re-crystallized from the mixture DCM-hexane, yielding 15.0 g (73%) of intermediate 59.

e) Preparation of Intermediate 60

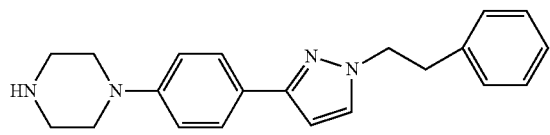 [SMILES: c1ccc(CCn2ccc(-c3ccc(N4CCNCC4)cc3)n2)cc1]

Intermediate 59 (23.55 g; 0.0545 mol) was dissolved in dry acetonitrile (500 ml), then HCl 6N (250 ml; 1.50 mol) was added and the reaction mixture was held overnight. After that the reaction mixture was evaporated to remove acetonitrile (about 400 ml), diluted with water (300 ml) and extracted with benzene. The aqueous layer was separated and basified with 1N KOH to pH=9-10. This led to the formation of oily product that gradually became crystalline. This product was filtered and washed with water. Then the precipitate was dissolved in DCM (200 ml) and insoluble admixtures were filtered off. The filtrate was concentrated in vacuum, yielding 17.0 g (94%) of intermediate 60.

Example A21 a) Preparation of Intermediate 61

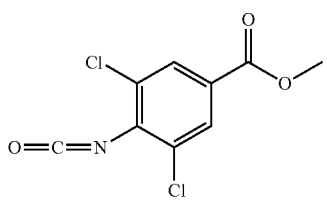

Norite (0.8 g) was added to a solution of methyl 4-amino-3,5-dichlorobenzoic acid ester (8.00 g; 36.3 mmol) and trichloromethyl carbonochloridic acid ester (8.0 ml; 66.2 mmol) in dry toluene (72 ml). The resulting mixture was heated at stirring in stainless steel bomb of a Parr apparatus at 110° C. for 20 hours. Then the reaction mixture was cooled and filtered through a pad of celite. The filtrate was bubbled with argon for 2 hours to remove phosgene and hydrogen chloride. Then the filtrate was concentrated in vacuum. The crude product was treated with cold hexane (15 ml), the precipitate was filtered off and the filtrate was evaporated to yield 2.82 g (31.5%) of intermediate 61. The precipitate was treated with hexane (40 ml) at stirring at 40° C. The small amount of dark sediment was removed by filtration and the filtrate was concentrated to yield 5.68 g (64%) of intermediate 61.

The total yield of intermediate 61 is 8.50 g (95%).

B. Preparation of the Compounds

Example B1

Preparation of compound 1

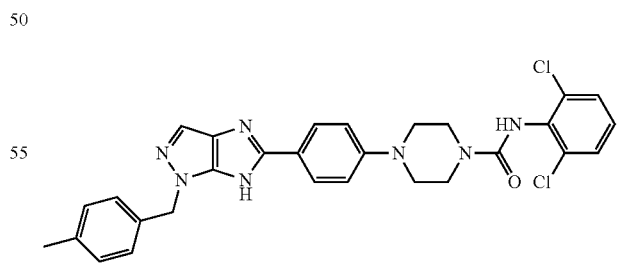

A mixture of intermediate 4 (0.060 g, 0.000161 mol) and 1,3-dichloro-2-isocyanatobenzene (0.033 g, 0.000177 mol) in dry THF (1 ml) was shaken overnight at room temperature. The solvent was evaporated and the residue was washed with Et₂O (2×), yielding 0.081 g (90%) of compound 1.

Example B2 a) Preparation of Compound 2

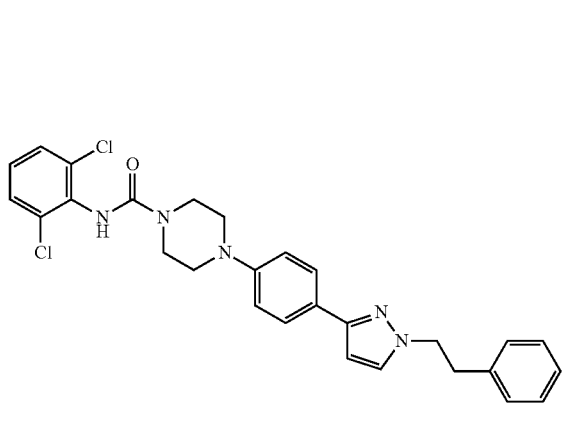 [SMILES: O=C(Nc1c(Cl)cccc1Cl)N1CCN(c2ccc(-c3ccn(CCc4ccccc4)n3)cc2)CC1]

A mixture of intermediate 8 (0.085 g, 0.00021 mol), Et₃N (0.091 g, 0.0009 mol) and CH₂Cl₂ (5 ml) was stirred for 15 minutes at room temperature. 1,3-Dichloro-2-isocyanatobenzene (0.056 g, 0.0003 mol) was added and the reaction mixture was stirred overnight at room temperature. The mixture was washed with H₂O (2 ml) and was dried over an Isolute filter. The organic layer was evaporated. The residue was purified by HPLC Method B. The pure fractions were collected and the solvent was evaporated. The residue was stirred in DIPE. The solvent was evaporated (stream of N₂ at 50° C.) and the solid was dried, yielding 0.046 g of compound 2.

b) Preparation of Compound 3

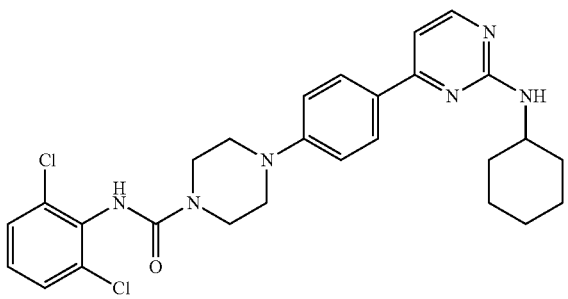 [SMILES: O=C(Nc1c(Cl)cccc1Cl)N1CCN(c2ccc(-c3ccnc(NC4CCCCC4)n3)cc2)CC1]

A mixture of intermediate 10 (0.307 g, 0.00075 mol), Et₃N (0.243 g, 0.0024 mol) and CH₂Cl₂ (q.s.) was stirred for 30 minutes at room temperature. Subsequently, 1,3-dichloro-2-isocyanatobenzene (0.147 g, 0.00078 mol) was added and the reaction mixture was stirred overnight at room temperature. The mixture was washed with H₂O (2 ml), dried over an Isolute filter and the solvent was evaporated. The residue was stirred in CH₃CN. The product was filtered off, washed with DIPE and dried, yielding 0.21 g of compound 3.

c) Preparation of Compound 4

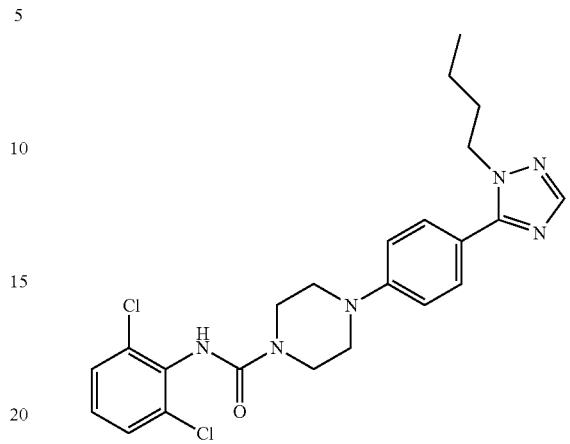

A mixture of intermediate 15 (0.179 g, 0.0005 mol), Et₃N (0.182 g, 0.0018 mol) and CH₂Cl₂ (10 ml) was stirred for 30 minutes at room temperature. 1,3-Dichloro-2-isocyanatobenzene (0.112 g, 0.0006 mol) was added and the reaction mixture was stirred for 3 hours at room temperature. The mixture was washed with H₂O (2 ml) and was dried over an Isolute filter. The organic layer was evaporated and the residue was purified by high-performance liquid chromatography. The pure fractions were collected and the solvent was evaporated. The residue was solidified by stirring in DIPE (2 ml). The solvent was evaporated and the solid residue was dried, yielding 0.071 g of compound 4.

Example B3

Preparation of Compound 5

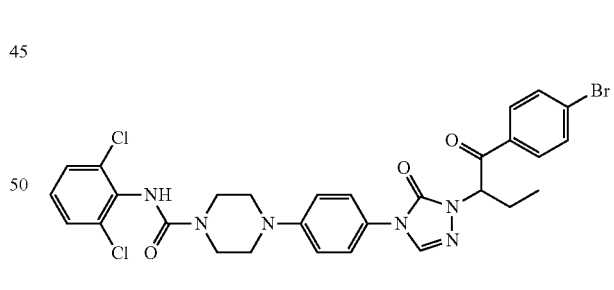

Intermediate 17 was converted into its hydrochloric acid salt by literature-known methods (0.25 g, 0.00049 mol; .HCl), and was then mixed with 1,3-dichloro-2-isocyanatobenzene (0.102 g, 0.00054 mol) and DIPEA (0.097 g, 0.00075 mol) in CH₂Cl₂ (25 ml) and stirred for 2 hours at room temperature. The solvent was evaporated and the residue was crystallized from DIPE. The precipitate was filtered off and dried. The crude product was stirred in H₂O and the aqueous layer was extracted with CH₂Cl₂. The separated organic layer was dried (Extrelut) and the solvent was evaporated, yielding 0.07 g of compound 5.

Example B4 a) Preparation of Compound 6

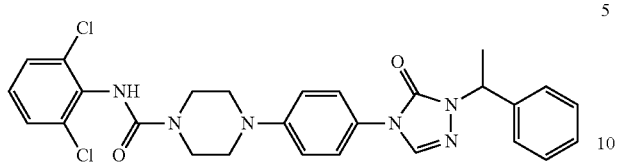

A mixture of intermediate 19 (0.00060 mol) and 1,3-dichloro-2-isocyanatobenzene (0.00066 mol) in CH$_2$Cl$_2$ (20 ml) was stirred at room temperature for 4 hours. The solvent was evaporated. The residue was triturated under DIPE. The precipitate was filtered off and dried, yielding 0.264 g of compound 6.

b) Preparation of Compound 7

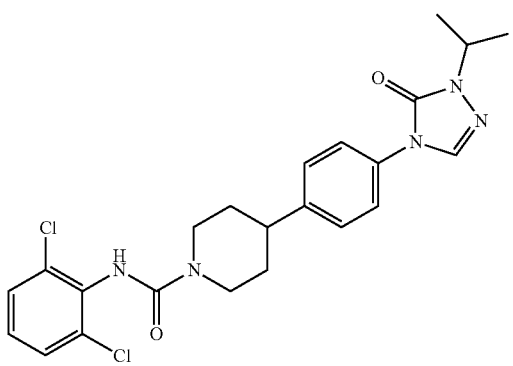 [SMILES: CC(C)n1ncn(-c2ccc(C3CCN(C(=O)Nc4c(Cl)cccc4Cl)CC3)cc2)c1=O]

1,3-Dichloro-2-isocyanatobenzene (0.000698 mol) was added to a slightly cloudy solution of intermediate 22 (0.000698 mol) in CH$_2$Cl$_2$ (10 ml, p.a.), stirred at room temperature. The reaction mixture was stirred overnight at room temperature. The mixture was purified by flash column chromatography over a Biotage 60 cartridge (eluent: CH$_2$Cl$_2$/(7N NH$_3$/CH$_3$OH) from 100/0 to 95/5 v/v). The product fractions were collected and the solvent was evaporated, yielding 0.171 g of compound 7.

Example B5

Preparation of Compound 8

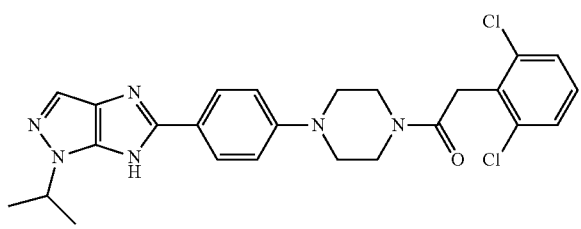 [SMILES: CC(C)n1ncc2nc(-c3ccc(N4CCN(C(=O)Cc5c(Cl)cccc5Cl)CC4)cc3)[nH]c21]

A mixture of intermediate 25 (0.060 g, 0.000193 mol), 2,6-dichlorobenzeneacetic acid (0.048 g, 0.000232 mol), EDCI (0.044 g, 0.000232 mol), HOBt .H$_2$O (0.036 g, 0.000232 mol) and DIPEA (0.000965 mol) in dry CH$_2$Cl$_2$ (1 ml) was shaken overnight at 50° C. CH$_2$Cl$_2$ was added to the mixture and the mixture was extracted with NaHCO$_3$ (half saturated) and H$_2$O. The separated organic layer was filtered over silica and dried (MgSO$_4$). The solvent was evaporated. The residue was purified by preparative HPLC (column 100× 21 mm, Nucleosil (Macherey-Nagel) Si50, 10 µm; gradient: CH$_2$Cl$_2$/CH$_3$OH: 0.0 min: 100/0; 1.2 min: 100/0; 5.0 min: 0/100; 9.0 min. 0/100; flow rate: 35 ml/min). The desired fractions were collected and worked-up, yielding 0.070 g (73%) of compound 8.

Example B6

Preparation of Compound 24

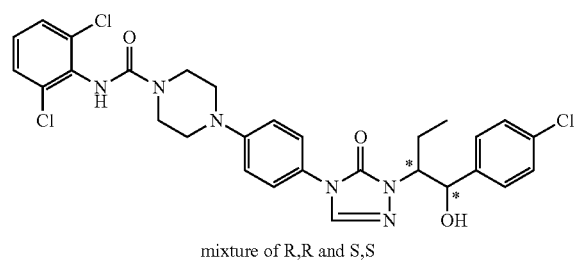 [SMILES: CCC(C(O)c1ccc(Cl)cc1)n1ncn(-c2ccc(N3CCN(C(=O)Nc4c(Cl)cccc4Cl)CC3)cc2)c1=O]

mixture of R,R and S,S

A mixture of intermediate 26 (0.250 g, 0.00058 mol), 1,3-dichloro-2-isocyanatobenzene (0.121 g, 0.00064 mol) and CH$_2$Cl$_2$ (25 ml) was stirred for 2 hours at room temperature. The solvent was evaporated and DIPE was added to the residue. The solid was filtered off and dried. The crude compound was purified by reversed-phase HPLC (HPLC method C). The desired fractions were collected and worked-up, yielding 0.204 g of compound 24.

Example B7

Preparation of Compound 29

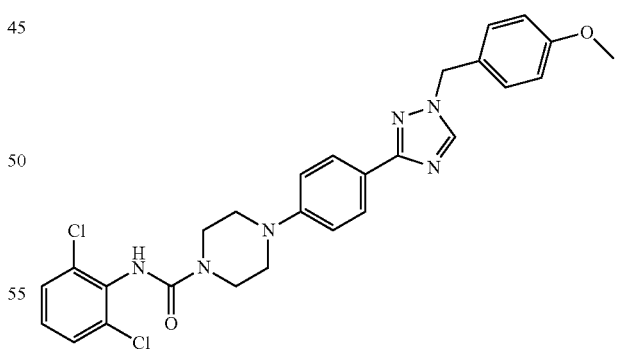

A mixture of intermediate 36 (0.295 g; 0.7 mmol), triethylamine (0.56 ml; 4 mmol) and CH$_2$Cl$_2$ (10 ml) was stirred at room temperature for 15 minutes. 1,3-Dichloro-2-isocyanatobenzene (0.188 g; 1 mmol) was added. The mixture was stirred for 18 hours. The mixture was washed with 2 ml water and dried over Isolute filter. The organic layer was evaporated. The residue was filtered over silica gel using a mixture of CH$_2$Cl$_2$ and CH$_3$OH (97/3 by volume) as eluent. The pure fractions were collected and the solvent was evaporated. The residue was dried, yielding 0.277 g of compound 29.

Example B8

Preparation of Compound 54

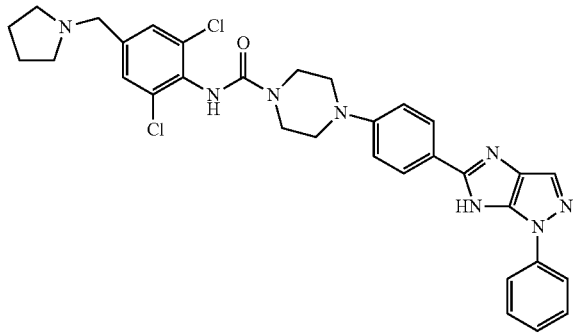 [SMILES: O=C(Nc1c(Cl)cc(CN2CCCC2)cc1Cl)N1CCN(c2ccc(-c3nc4cnn(-c5ccccc5)c4[nH]3)cc2)CC1]

To a suspension of intermediate 32 (527.048 mg; 1.872 mmol) in 10 ml of acetonitrile and 4 ml of DCM, C(=O)Cl$_2$ 20% in toluene (1.701 ml; 3.403 mmol) was added. The suspension was stirred overnight at room temperature. The reaction was filtered and washed with fresh dry CH$_3$CN. The isocyanate precipitate was added to a suspension of intermediate 30 (586 mg; 1.701 mmol) and DIPEA (0.845 ml; 5.104 mmol in DCM (20 ml). Meanwhile, the filtrate was concentrated at 30° C. to remove DCM and 1.7 ml of fresh C(=O)Cl$_2$ 20% in toluene was added and stirred for 3 hours at room temperature. A second batch of intermediate 32 (431 mg) was added to the mixture and stirred overnight. The suspension was filtered, the residue was washed with a little dry CH$_3$CN and added to the reaction mixture of intermediate 30. The reaction was evaporated. The residue was purified by reversed phase high-performance liquid chromatography (Shandon Hyperprep® C18 BDS (Base Deactivated Silica) 8 μm, 250 g, I.D. 5 cm). A gradient with the following mobile phases was applied. Phase A: 90% of a 0.5% NH$_4$OAc solution in water+ 10% CH$_3$CN; phase B (optional): CH$_3$OH; phase C: CH$_3$CN). The desired fractions were collected, partially evaporated at 30° C. and neutralized to pH 8-9 with a saturated NaHCO$_3$ solution. The formed precipitate was filtered off and dried, yielding 820 mg of compound 54 (78%).

Table 1a lists compounds of formula (I) according to the present invention prepared by analogy to one of the above Example Nr.

TABLE 1a-continued
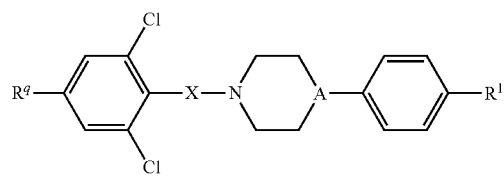
| Co. No. | Ex. No. | A | X | R¹ | R^q |
|---|---|---|---|---|---|
| 5 | B3 | N | -NH-C(=O)- | 4-(4-bromobenzoyl-propyl)-triazolone | H— |
| 6 | B4.a | N | -NH-C(=O)- | 1-(1-phenylethyl)-triazolone | H— |
| 7 | B4.b | CH | -NH-C(=O)- | 1-isopropyl-triazolone | H— |
| 8 | B5 | N | -CH₂-C(=O)- | 1-isopropyl-imidazo-pyrazole | H— |
| 9 | B1 | N | -NH-C(=O)- | 1-isopropyl-imidazo-pyrazole | H— |
| 10 | B2.a | N | -NH-C(=O)- | 1-benzyl-pyrazol-3-yl | H— |
| 11 | B2.a | N | -NH-C(=O)- | 2-(2,6-dichlorobenzyl)-pyrimidin-4-yl | H— |

TABLE 1a-continued
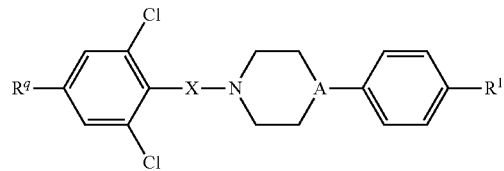
| Co. No. | Ex. No. | A | X | R¹ | Rq |
|---|---|---|---|---|---|
| 12 | B2.a | N | 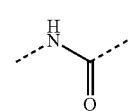 | 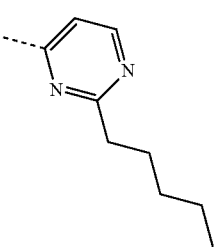 | H— |
| 13 | B2.a | N | 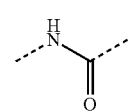 | 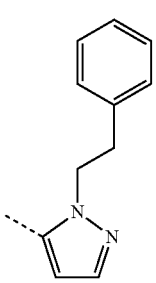 | H— |
| 14 | B2.a | N | 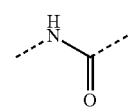 | 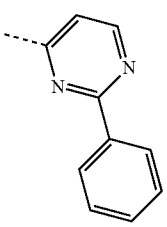 | H— |
| 15 | B2.a | N | 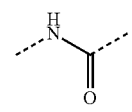 | 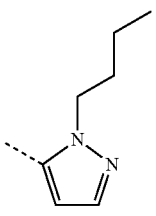 | H— |
| 16 | B2.a | N | 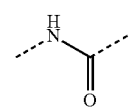 | 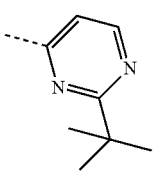 | H— |

TABLE 1a-continued

| Co. No. | Ex. No. | A | X | R¹ | Rq |
|---|---|---|---|---|---|
| 17 | B2.a | N | -NHC(=O)- | 4-(1-ethoxycarbonylpiperidin-4-ylamino)pyrimidin-2-yl | H— |
| 18 | B2.a | N | -NHC(=O)- | 1-(4-methoxyphenyl)-1H-pyrazol-5-yl | H— |
| 19 | B2.b | N | -NHC(=O)- | 4-(isopentylamino)pyrimidin-2-yl | H— |
| 20 | B2.b | N | -NHC(=O)- | 4-(benzylamino)pyrimidin-2-yl | H— |
| 21 | B2.b | N | -NHC(=O)- | 2-(piperidin-1-yl)pyrimidin-4-yl | H— |

TABLE 1a-continued
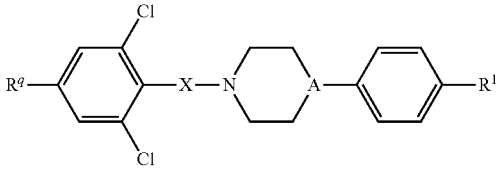
| Co. No. | Ex. No. | A | X | R¹ | Rq |
|---|---|---|---|---|---|
| 22 | B2.c | N | 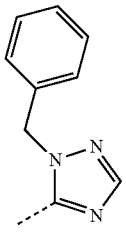 | 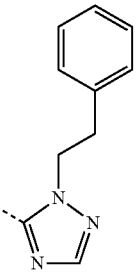 | H— |
| 23 | B2.c | N | 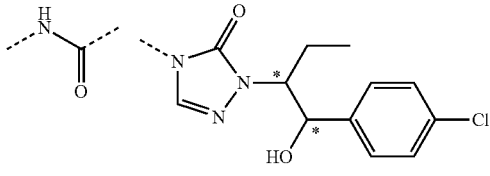 | 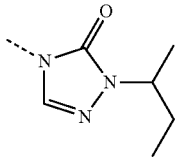 | H— |
| 24 | B6 | N | 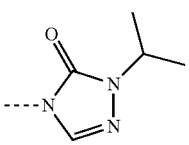 | 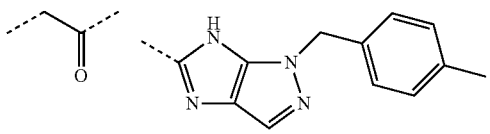  mixture of RR and SS | H— |
| 25 | B4.a | N | 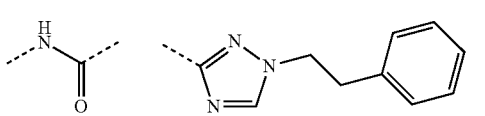 |  | H— |
| 26 | B4.a | N |  |  | H— |
| 27 | B5 | N |  |  | H— |
| 28 | B7 | N |  |  | H— |

TABLE 1a-continued
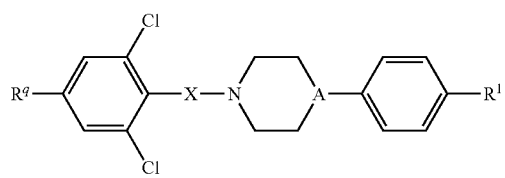
| Co. No. | Ex. No. | A | X | R[1] | R[q] |
|---|---|---|---|---|---|
| 29 | B7 | N | -NHC(O)- | 1-(4-methoxybenzyl)-1,2,4-triazol-3-yl | H— |
| 30 | B7 | N | -NHC(O)- | 1-(3-phenylpropyl)-1,2,4-triazol-3-yl | H— |
| 31 | B7 | N | -NHC(O)- | 5-(2-phenylethyl)-1,3,4-oxadiazol-2-yl | H— |
| 32 | B7 | N | -NHC(O)- | 1-butyl-1,2,4-triazol-3-yl | H— |
| 33 | B7 | N | -NHC(O)- | 3-(3-phenylpropyl)-1,2,4-oxadiazol-5-yl | H— |
| 34 | B7 | N | -NHC(O)- | 3-benzyl-1,2,4-oxadiazol-5-yl | H— |
| 35 | B7 | N | -NHC(O)- | 5-benzyl-1,3,4-oxadiazol-2-yl | H— |
| 36 | B7 | N | -NHC(O)- | 5-butyl-1,3,4-oxadiazol-2-yl | H— |

TABLE 1a-continued
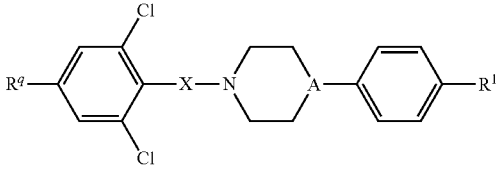
| Co. No. | Ex. No. | A | X | R¹ | Rq |
|---|---|---|---|---|---|
| 37 | B7 | N | -NHC(=O)- | 5-phenyl-1,2,4-oxadiazol-3-yl | H— |
| 38 | B7 | N | -NHC(=O)- | 5-tert-butyl-1,3,4-oxadiazol-2-yl | H— |
| 39 | B7 | N | -NHC(=O)- | 3-tert-butyl-1,2,4-oxadiazol-5-yl | H— |
| 40 | B7 | N | -NHC(=O)- | 1-tert-butyl-1,2,4-triazol-3-yl | H— |
| 41 | B2.a | N | -NHC(=O)- | 1-(3-phenylpropyl)-1H-pyrazol-3-yl | H— |
| 42 | B7 | N | -NHC(=O)- | 1H-1,2,4-triazol-5-yl | H— |
| 43 | B7 | N | -NHC(=O)- | imidazo[2,1-b]thiazol-6-yl | H— |
| 44 | B4.b | CH | -NHC(=O)- | 5-oxo-4-methyl-1-(3-phenylpropyl)-4,5-dihydro-1H-1,2,4-triazol-3-yl | H— |

TABLE 1a-continued

| Co. No. | Ex. No. | A | X | R¹ | Rq |
|---|---|---|---|---|---|
| 45 | B2.c | N | -NH-C(=O)- | 4-methoxybenzyl-1,2,4-triazol-5-yl | H— |
| 46 | B4.b | CH | -NH-C(=O)- | 2-(4-methoxybenzyl)-3-oxo-2,3-dihydro-1,2,4-triazol-4-yl | H— |
| 47 | B2.c | N | -NH-C(=O)- | 1-isopropyl-1,2,4-triazol-5-yl | H— |
| 48 | B4.b | CH | -NH-C(=O)- | 2-(2-phenylethyl)-3-oxo-2,3-dihydro-1,2,4-triazol-4-yl | H— |
| 49 | B7 | N | -NH-C(=O)- | 5-methyl-1,3,4-oxadiazol-2-yl | H— |
| 50 | B4.b | CH | -NH-C(=O)- | 2-benzyl-3-oxo-2,3-dihydro-1,2,4-triazol-4-yl | H— |
| 51 | B7 | N | -NH-C(=O)- | 3-(3-(diethylamino)propyl)-1,2,4-oxadiazol-5-yl | H— |
| 52 | B5 | N | -C(=O)- | 2-phenylimidazo[2,1-b]thiazol-6-yl | H— |

TABLE 1a-continued

| Co. No. | Ex. No. | A | X | R¹ | Rq |
|---|---|---|---|---|---|
| 53 | B8 | N | —NH—C(=O)— | 5-(1-cyclopentyl-1H-pyrazolo[3,4-d]imidazol-5-yl) | pyrrolidin-1-ylmethyl |
| 54 | B8 | N | —NH—C(=O)— | 5-(1-phenyl-1H-pyrazolo[3,4-d]imidazol-5-yl) | pyrrolidin-1-ylmethyl |
| 55 | B8 | N | —NH—C(=O)— | 5-(1-(1-phenylethyl)-1H-pyrazolo[3,4-d]imidazol-5-yl) | pyrrolidin-1-ylmethyl |
| 56 | B8 | N | —NH—C(=O)— | 5-(1-benzyl-1H-pyrazolo[3,4-d]imidazol-5-yl) | pyrrolidin-1-ylmethyl |
| 57 | B2.a | N | —NH—C(=O)— | 1-(2-phenylethyl)-1H-pyrazol-3-yl | HOCH₂— |
| 58 | B8 | N | —NH—C(=O)— | 5-(1-isopropyl-1H-imidazo[4,5-d]imidazol-5-yl) | pyrrolidin-1-ylmethyl |

TABLE 1a-continued
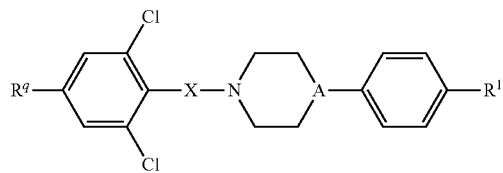
| Co. No. | Ex. No. | A | X | R¹ | Rq |
|---|---|---|---|---|---|
| 59 | B2.a | N | -NH-C(=O)- | pyrazol-3-yl, N1-(3-phenylpropyl) | HOCH₂— |
| 60 | B8 | N | -NH-C(=O)- | 1,2,4-triazol-3-yl, N1-(2-phenylethyl) | pyrrolidin-1-ylmethyl |
| 61 | B2.a | N | -NH-C(=O)- | pyrazol-3-yl, N1-(2-phenylethyl) | HO— |
| 62 | B2.a | N | -NH-C(=O)- | pyrazol-3-yl, N1-(3-phenylpropyl) | HO— |
| 63 | B7 | N | -NH-C(=O)- | pyrazol-3-yl, N1-(2-phenylethyl) | -O-C(=O)- |
| 64 | B8 | N | -NH-C(=O)- | imidazo[2,1-b]thiazol-6-yl | pyrrolidin-1-ylmethyl |
| 65 | B7 | N | -NH-C(=O)- | pyrazol-3-yl, N1-(3-phenylpropyl) | -O-C(=O)- |

TABLE 1b
| Co. No. | X | R¹ | R² | Salt |
|---|---|---|---|---|
| 66 | 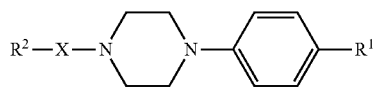 | 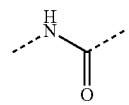 | 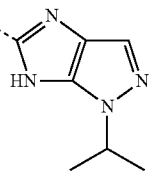 | |
| 67 | 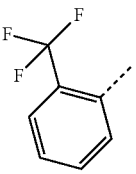 | 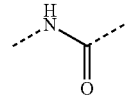 | 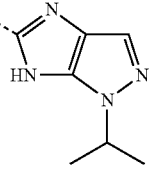 | |
| 68 | 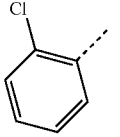 | 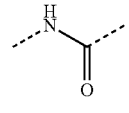 | 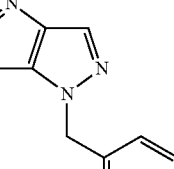 | |
| 69 | 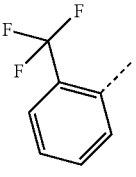 | 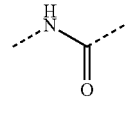 | 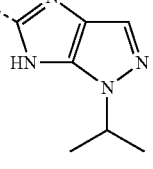 | |
| 70 | 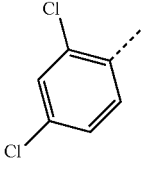 | 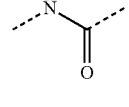 | 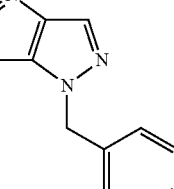 | |
| 71* | 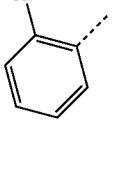 | 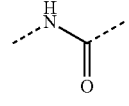 | 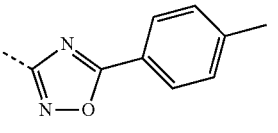 | |
| 72 | 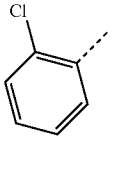 | 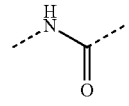 | 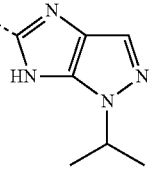 | |

TABLE 1b-continued

| Co. No. | X | R¹ | R² | Salt |
|---|---|---|---|---|
| 73* | NH-C(=O) | 5-cyclohexyl-1,2,4-oxadiazol-3-yl | 2-(trifluoromethyl)phenyl | |
| 74* | NH-C(=O) | 5-cyclopropyl-1,2,4-oxadiazol-3-yl | 2,4-dichlorophenyl | |
| 75 | NH-C(=O) | 1-(4-methylbenzyl)-1H-pyrazolo-imidazol-5-yl | 2,4-dichlorophenyl | |
| 76* | NH-C(=O) | 5-cyclohexyl-1,2,4-oxadiazol-3-yl | 2-chlorophenyl | |
| 77 | NH-C(=O) | 1-(4-methylbenzyl)-1H-pyrazolo-imidazol-5-yl | naphth-1-yl | |
| 78 | NH-C(=O) | 1-isopropyl-1H-pyrazolo-imidazol-5-yl | 4-(dimethylamino)phenyl | |
| 79 | NH-C(=O) | 1-(4-methylbenzyl)-1H-pyrazolo-imidazol-5-yl | 4-(dimethylamino)phenyl | |

TABLE 1b-continued

R²—X—N(piperazine)N—C₆H₄—R¹

| Co. No. | X | R¹ | R² | Salt |
|---|---|---|---|---|
| 80* | -NH-C(=O)- | 5-cyclobutyl-1,2,4-oxadiazol-3-yl | 2-bromophenyl | |
| 81 | -NH-C(=O)- | 1-isopropyl-1H-imidazo[4,5-c]pyrazol-5-yl | 4-methylphenyl | |
| 82 | -NH-C(=O)- | 1-isopropyl-1H-imidazo[4,5-c]pyrazol-5-yl | 4-methoxyphenyl | |
| 83 | -NH-C(=O)- | 1-(4-methylbenzyl)-1H-imidazo[4,5-c]pyrazol-5-yl | 2-methoxyphenyl | |
| 84 | -NH-C(=O)- | 1-isopropyl-1H-imidazo[4,5-c]pyrazol-5-yl | 2-methoxyphenyl | |
| 85 | -NH-C(=O)- | 1-isopropyl-1H-imidazo[4,5-c]pyrazol-5-yl | 3-methylphenyl | |
| 86 | -NH-C(=O)- | 1-isopropyl-1H-imidazo[4,5-c]pyrazol-5-yl | 4-(methylthio)phenyl | |
| 87* | -C(=O)- | 5-methyl-1,2,4-oxadiazol-3-yl | 2-chloro-6-fluorophenyl | |

TABLE 1b-continued

| Co. No. | X | R¹ | R² | Salt |
|---|---|---|---|---|
| 88 | -NH-C(=O)- | 1-isopropyl-1H-pyrazolo[3,4-d]imidazol-5-yl | naphthalen-2-yl | |
| 89 | -CH2-NH-C(=O)- | 1-isopropyl-1H-pyrazolo[3,4-d]imidazol-5-yl | phenyl | |
| 90 | -NH-C(=O)- | 1-isopropyl-1H-pyrazolo[3,4-d]imidazol-5-yl | 3-methoxyphenyl | |
| 91 | -NH-C(=O)- | 1-isopropyl-1H-pyrazolo[3,4-d]imidazol-5-yl | 3-(morpholin-4-yl)phenyl | |
| 92 | -NH-C(=O)- | 1-isopropyl-1H-pyrazolo[3,4-d]imidazol-5-yl | benzo[1,3]dioxol-5-yl | |
| 93* | -C(=O)- | 5-ethyl-1,2,4-oxadiazol-3-yl | 2-chloro-6-fluorophenyl | |
| 94 | -NH-C(=O)- | 1-(4-methylbenzyl)-1H-pyrazolo[3,4-d]imidazol-5-yl | 4-methoxyphenyl | |

TABLE 1b-continued

R²—X—N(piperazine)N—C₆H₄—R¹

| Co. No. | X | R¹ | R² | Salt |
|---|---|---|---|---|
| 95 | -NH-C(=O)- | 5-(4-methylbenzyl)-pyrazolo-imidazole | phenyl | |
| 96 | -NH-C(=O)- | 5-(4-methylbenzyl)-pyrazolo-imidazole | cyclopropyl | |
| 97 | -NH-C(=O)- | 5-(4-methylbenzyl)-pyrazolo-imidazole | 4-(acetylamino)phenyl | |
| 98* | -NH-C(=O)- | 5-methyl-1,2,4-oxadiazol-3-yl | 2-bromophenyl | |
| 99 | -NH-C(=O)- | 5-(4-methylbenzyl)-pyrazolo-imidazole | 1,3-benzodioxol-5-yl | |
| 100 | -NH-C(=O)- | 5-(1-isopropyl)-pyrazolo-imidazole | 3-fluorophenyl | |

TABLE 1b-continued

R²—X—N(piperazine)N—phenyl—R¹

| Co. No. | X | R¹ | R² | Salt |
|---|---|---|---|---|
| 101 | —NH—C(=O)— | 5-(1-isopropyl-1H-imidazo[4,5-c]pyrazol-5-yl) | phenyl | |
| 102 | —CH₂—NH—C(=O)— | 5-(1-(4-methylbenzyl)-1H-imidazo[4,5-c]pyrazol-5-yl) | phenyl | |
| 103 | —NH—C(=O)— | 5-(1-(4-methylbenzyl)-1H-imidazo[4,5-c]pyrazol-5-yl) | 3-morpholinophenyl | |
| 104 | —CH₂—C(=O)— | 5-(1-isopropyl-1H-imidazo[4,5-c]pyrazol-5-yl) | phenyl | |
| 105 | —NH—C(=O)— | 5-(1-(4-methylbenzyl)-1H-imidazo[4,5-c]pyrazol-5-yl) | 4-methylphenyl | |
| 106 | —NH—C(=O)— | 5-(1-isopropyl-1H-imidazo[4,5-c]pyrazol-5-yl) | 3-(dimethylamino)phenyl | |
| 107* | —CH₂—C(=O)— | 3-(5-cyclopropyl-1,2,4-oxadiazol-3-yl) | 2-chloro-6-fluorophenyl | |

TABLE 1b-continued

| Co. No. | X | R¹ | R² | Salt |
|---|---|---|---|---|
| 108 | carbonyl | 5-(4-methylbenzyl)-1H-imidazo[4,5-c]pyrazol-3-yl | phenyl | |
| 109* | NHC(=O) | 5-cyclohexyl-1,2,4-oxadiazol-3-yl | 2,4-dimethoxyphenyl | |
| 110 | CH₂NHC(=O) | 5-(4-methylbenzyl)-1H-imidazo[4,5-c]pyrazol-3-yl | phenyl | |
| 111* | carbonyl | 5-methyl-1,2,4-oxadiazol-3-yl | 2-bromophenyl | |
| 112 | NHC(=O) | 5-isopropyl-1H-imidazo[4,5-c]pyrazol-3-yl | 4-chlorophenyl | |
| 113* | carbonyl | 5-cyclobutyl-1,2,4-oxadiazol-3-yl | 2-bromophenyl | |
| 114 | NHC(=O) | 5-isopropyl-1H-imidazo[4,5-c]pyrazol-3-yl | 4-pyridyl | |

TABLE 1b-continued

| Co. No. | X | R¹ | R² | Salt |
|---|---|---|---|---|
| 115 | amide (NH-C(=O)) | imidazo-pyrazole with isopropyl | 4-hydroxybenzoyl phenyl | trifluoroacetate salt |
| 116 | amide (NH-C(=O)) | imidazo-pyrazole with 4-methylbenzyl | 4-chlorophenyl | |
| 117* | C(=O) | 5-cyclopropyl-1,2,4-oxadiazole | 2-bromophenyl | |

*library compounds from third party

C. Analytical Part

LCMS

For LCMS-characterization of the compounds of the present invention, the following methods were used.

General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS detector. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure C

The LCMS analyses for the compounds were done at the Surveyor MSQ™ (Thermo Finnigan, USA) comprising a photo diode array detector (PDA; 190-800 nm) and a column as specified in the respective methods below. Flow from the column was split to a MS spectrometer. The MS detector was configured with APCI (atmospheric pressure chemical ionization, + or − ions). Mass spectra were acquired by scanning from 45 to 1000 (of atomic mass unit) in 0.3 seconds. Typical APCI conditions use a corona discharge current of 10 µA and a cone voltage of 30 V. The APCI probe temperature was 640° C. Nitrogen was used as the nebulizer gas. Data acquisition was performed with an Xcalibur™ data system.

LCMS Procedure 1

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS Procedure 2

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Procedure 3

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 09 minutes, to 100% B in 0.3 minutes and hold for 0.2 minutes. An injection volume of 2 μl was used. Cone voltage was 10 V for positive ionization mode and 20 V for negative ionization mode.

LCMS Procedure 4

In addition to general procedure B: Reversed phase UPLC (Ultra Performance Liquid Chromatography) was carried out on a bridged ethylsiloxane/silica (BEH) C18 column (1.7 μm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Procedure 5

In addition to general procedure C: Reversed phase HPLC was carried out on a Waters XTerra MS C18 column (3.5 μm, 2.1×30 mm) with a flow rate of 1.0 ml/min. Two mobile phases (mobile phase A: 0.1% aqueous solution of formic acid; mobile phase B: acetonitrile) were used. First, 100% A was hold for 0.1 minutes. Then a gradient was applied to 5% A and 95% B in 3 minutes and hold for 0.8 minutes. The injection volume was 1 μl. The column was at room temperature.

Melting Points

For a number of compounds, melting points were determined with a DSC823e (Mettler-Toledo). Melting points were measured with a temperature gradient of 30° C./minute. Maximum temperature was 400° C.

Values are peak values and are obtained with experimental uncertainties that are commonly associated with this analytical method.

For a number of compounds, melting points were determined by using a Gallenkamp apparatus from Sanyo Gallenkamp. The melting points determined in this way are indicated with '*'.

TABLE 2a

LCMS and melting point analytical data ($R_t$: Retention time in minutes; [M + H]+ means the protonated mass of the compound, LCMS procedure refers to the method used for LCMS).

| Comp. Nr. | $R_t$ | [M + H]+ | LCMS Procedure | Melting point (° C.) |
|---|---|---|---|---|
| 1 | 1.28 | 560 | 4 | n.d. |
| 9 | 1.15 | 498 | 4 | n.d. |
| 8 | 1.26 | 497 | 4 | n.d. |
| 27 | 1.36 | 559 | 4 | n.d. |
| 2 | 6.23 | 520 | 1 | 163.4 |
| 6 | 5.81 | 537 | 1 | 207.9 |
| 10 | 6.10 | 506 | 1 | 191.4 |
| 24 | 5.96 | 615 | 1 | n.d. |
| 4 | 5.36 | 473 | 2 | 135.5 |
| 5 | 6.23 | 657 | 1 | n.d. |
| 25 | 0.89 | 489 | 3 | 165.7 |
| 3 | 5.96 | 525 | 2 | 203.2 |
| 22 | 5.33 | 507 | 2 | 209.4 |
| 19 | 5.89 | 513 | 2 | 179.3 |
| 23 | 5.46 | 521 | 2 | 181.0 |
| 26 | 5.15 | 475 | 1 | 194.1 |
| 20 | 5.57 | 533 | 2 | 220.3 |
| 7 | 4.98 | 474 | 2 | 215.0 |
| 11 | 5.99 | 586 | 2 | 249.8 |
| 12 | 5.96 | 498 | 2 | n.d. |
| 14 | 6.60 | 504 | 1 | 222.3 |
| 13 | 6.22 | 520 | 1 | 167.3 |
| 15 | 5.44 | 472 | 2 | 183.2 |
| 21 | 6.04 | 511 | 2 | 247.7 |
| 16 | 6.61 | 484 | 1 | 193.8 |
| 17 | 5.43 | 598 | 2 | n.d. |
| 18 | 5.27 | 522 | 2 | n.d. |
| 28 | 5.67 | 521 | 1 | 174.8 |
| 29 | 5.24 | 537 | 2 | 185.4 |
| 30 | 5.97 | 535 | 1 | 181.9 |
| 31 | 5.70 | 522 | 2 | 189.4 |
| 32 | 5.26 | 473 | 2 | 175.2 |
| 33 | 6.59 | 536 | 1 | 146.3 |
| 34 | 6.18 | 508 | 1 | 180.1 |
| 35 | 5.44 | 508 | 2 | 201.0 |
| 36 | 5.52 | 474 | 2 | 181.9 |
| 38 | 5.75 | 474 | 1 | 214.0 |
| 39 | 6.28 | 474 | 1 | 209.3 |
| 40 | 4.94 | 459 | 2 | 186.7 |
| 41 | 6.04 | 534 | 2 | 137.3 |
| 42 | 4.34 | 418 | 1 | n.d. |
| 43 | n.d. | n.d. | — | n.d. |
| 44 | 1.94 | 550 | 5 | 177-178* |
| 45 | 5.17 | 537 | 2 | 173.9 |
| 46 | 1.85 | 552 | 5 | 100-105* |
| 47 | 4.89 | 459 | 2 | 202.5 |
| 48 | 1.89 | 536 | 5 | 200-201* |
| 49 | 4.87 | 432 | 1 | 235.0 |
| 50 | 1.85 | 522 | 5 | 180-181* |
| 51 | 4.39 | 531 | 2 | n.d. |
| 52 | 6.83 | 547 | 1 | 290.5 |
| 53 | 5.26 | 507 | 2 | n.d. |
| 54 | 5.78 | 615 | 1 | 231.7 |
| 55 | 5.32 | 643 | 2 | 208.4 |
| 56 | 5.09 | 629 | 2 | 160.2 |
| 57 | 1.83 | 550 | 5 | 147-148* |
| 58 | 4.77 | 581 | 2 | n.d. |
| 59 | 1.91 | 564 | 5 | 189-191* |
| 60 | n.d. | n.d. | — | 172.8 |
| 61 | 1.85 | 536 | 5 | 165-167* |
| 62 | 1.95 | 550 | 5 | 207-209* |
| 63 | 2.01 | 578 | 5 | 194-195* |
| 64 | n.d. | n.d. | — | 235.3 |
| 65 | 2.07 | 592 | 5 | 148-149* |
| 66 | 1.19 | 498 | 4 | n.d. |
| 67 | 1.19 | 464 | 4 | n.d. |
| 68 | 1.31 | 560 | 4 | n.d. |
| 69 | 1.30 | 498 | 4 | n.d. |
| 70 | 1.32 | 526 | 4 | n.d. |
| 71 | 1.51 | 474 | 4 | n.d. |
| 72 | 1.20 | 480 | 4 | n.d. |
| 73 | 1.48 | 500 | 4 | n.d. |
| 74 | 1.37 | 438 | 4 | n.d. |
| 75 | 1.40 | 560 | 4 | n.d. |
| 76 | 1.49 | 466 | 4 | n.d. |
| 77 | 1.32 | 542 | 4 | n.d. |
| 78 | 0.88 | 473 | 4 | n.d. |
| 79 | 1.06 | 535 | 4 | n.d. |
| 80 | 1.41 | 482 | 4 | n.d. |
| 81 | 1.19 | 444 | 4 | n.d. |
| 82 | 1.11 | 460 | 4 | n.d. |
| 83 | 1.30 | 522 | 4 | n.d. |
| 84 | 1.17 | 460 | 4 | n.d. |

TABLE 2a-continued

LCMS and melting point analytical data ($R_t$: Retention time in minutes; [M + H]$^+$ means the protonated mass of the compound, LCMS procedure refers to the method used for LCMS).

| Comp. Nr. | $R_t$ | [M + H]$^+$ | LCMS Procedure | Melting point (° C.) |
|---|---|---|---|---|
| 85  | 1.20 | 444 | 4 | n.d. |
| 86  | 1.21 | 476 | 4 | n.d. |
| 87  | 1.25 | 415 | 4 | n.d. |
| 88  | 1.26 | 480 | 4 | n.d. |
| 89  | 1.14 | 444 | 4 | n.d. |
| 90  | 1.14 | 460 | 4 | n.d. |
| 91  | 1.13 | 515 | 4 | n.d. |
| 92  | 1.11 | 474 | 4 | n.d. |
| 93  | 1.32 | 429 | 4 | n.d. |
| 94  | 1.26 | 522 | 4 | n.d. |
| 95  | 1.27 | 492 | 4 | n.d. |
| 96  | 1.18 | 456 | 4 | n.d. |
| 97  | 1.16 | 549 | 4 | n.d. |
| 98  | 1.25 | 442 | 4 | n.d. |
| 99  | 1.25 | 536 | 4 | n.d. |
| 101 | 1.14 | 430 | 4 | n.d. |
| 102 | 1.28 | 506 | 4 | n.d. |
| 103 | 1.26 | 577 | 4 | n.d. |
| 104 | 1.16 | 429 | 4 | n.d. |
| 105 | 1.32 | 506 | 4 | n.d. |
| 106 | 0.99 | 473 | 4 | n.d. |
| 107 | 1.34 | 441 | 4 | n.d. |
| 108 | 1.30 | 491 | 4 | n.d. |
| 109 | 1.45 | 492 | 4 | n.d. |
| 110 | 1.34 | 505 | 4 | n.d. |
| 111 | 1.29 | 441 | 4 | n.d. |
| 112 | 1.24 | 464 | 4 | n.d. |
| 113 | 1.44 | 481 | 4 | n.d. |
| 115 | 1.07 | 474 | 4 | n.d. |
| 116 | 1.35 | 526 | 4 | n.d. |
| 117 | 1.38 | 467 | 4 | n.d. | n.d. = not determined

TABLE 2b

LCMS analytical data - $R_t$ means retention time (in minutes), [M − H]$^-$ means the deprotonated mass of the compound (negative mode), LCMS procedure refers to the method used for LCMS.

| Comp. Nr. | $R_t$ | [M − H]$^-$ | LCMS procedure | Melting point (° C.) |
|---|---|---|---|---|
| 37 | 6.46 | 492 | 1 | 232.4 |

D. Pharmacological Example

A) Measurement of Inhibition of DGAT1 Activity by the Present Compounds

The inhibiting activity of the present compounds on DGAT1 activity was screened in a single well procedure assay using DGAT1 comprising membrane preparations and DGAT1 substrate comprising micelles and determining formed radio-active triacylglycerol coming in close proximity of a flashplate surface by radioluminescence.

Said assay is described in full detail in WO2006/067071, the content of which is incorporated herein by reference.

By DGAT1 activity is meant the transfer of coenzyme A activated fatty acids to the 3-position of 1,2-diacylglycerols, thus forming a triglyceride molecule, by enzyme DGAT1.

Step 1 of the Assay: Expression of DGAT1 human DGAT1 (NM012079.2) was cloned into the pFast-Bac vector, containing translation start, a FLAG-tag at the N-terminus as described in literature and a viral Kozak sequence (AAX) preceding the ATG to improve expression in insect cells. Expression was done as described in literature (Cases, S., Smith, S. J., Zheng, Y., Myers H. M., Lear, S. R., Sande, E., Novak, S., Collins, C., Welch, C. B., Lusis, A. J., Erickson, S. K. and Farese, R. V. (1998) *Proc. Natl. Acad. Sci. USA* 95, 13018-13023) using SF9 cells.

Step 2 of the Assay: Preparation of DGAT1 Membranes 72 h transfected SF9 cells were collected by centrifugation (13000 rpm-15 min-4° C.) and lysed in 2×500 ml lysisbuffer (0.1M Sucrose, 50 mM KCl, 40 mM KH$_2$PO$_4$, 30 mM EDTA pH 7.2. Cells were homogenized by cell disruptor. After centrifugation 1380 rpm-15 min-4° C. (SN discarded), pellet was resuspended in 500 ml lysisbuffer and total cell membranes collected by ultracentrifugation at 34000 rpm (100 000 g) for 60 min (4° C.). The collected membranes were resuspended in lysis buffer, divided in aliquots and stored with 10% glycerol at −80° C. until use.

Step 3 of the Assay: Preparation of DGAT Substrate Comprising Micelles

Materials a) 1,2-dioleoyl-sn-glycerol, 10 mg/ml (1,2-diacylglycerol (DAG))

Dissolve in acetonitrile; evaporate the acetonitrile solution under nitrogen and reconstitute in chloroform at a final concentration of 10 mg/ml.

b) L-α-phosphatidylcholine, 1 mg/ml (phosphatidylcholine (PC))

Dissolve in chloroform at a final concentration of 1 mg/ml and store at 4° C.

c) L-α-phosphatidyl-L-serine, 1 mg/ml (phophatidylserine (PS))

Dissolve in chloroform at a final concentration of 1 mg/ml and store at 4° C.

Method

Add 1 ml dioleoyl-sn-glycerol (10 mg/ml) to 10 ml of L-α-phosphatidylcholine (1 mg/ml) and 10 ml of L-α-phosphatidyl-L-serine (1 mg/ml) in a thick glass recipient. Evaporate under nitrogen and put on ice for 15 minutes. Reconstitute in 10 ml Tris/HCl (10 mM, pH 7.4) by sonication on ice. The sonication process consists of sonification cycles of 10 seconds in the sonification bath followed by 10 seconds cool down on ice and repeating this sonification cycle till a homogeneous solution is obtained (takes about 15 minutes). The thus obtained micelles are stored at −20° C. till later use and contain DAG at a final concentration of 1.61 mM.

Step 4 of the Assay: DGAT FlashPlate™ Assay

Materials a) Assaybuffer 50 mM Tris-HCl (pH 7.4), 150 mM MgCl$_2$, 1 mM EDTA, 0.2% BSA.

b) N-ethylmaleimide, 5M

Dissolve 5 g into a final volume of 8 ml DMSO 100% and store at −20° C. in aliquots till later use.

c) Substrate mix (for 1 384 well plate=3840 μl)

612 μl micelles stock (51 μM final)

16.6 μl oleoylCoA 9.7 mM

23 μl [$^3$H]-oleoylCoA (49 Ci/mmol, 500 μCi/ml)

3188.4 μl Tris pH 7.4, 10 mM d) Enzyme mix (for 1 384 well plate=3520 μl) (5 mg/ml)

Add 11.73 μl of DGAT membrane stock (1500 μg/ml stock) to 3508 μl assay buffer.

e) Stop mix (for 1 384 well plate=7.68 ml) (250 mM)

Add 384 μl of N-ethylmaleimide (5M) to 3.456 ml DMSO 100%, and further dilute 3.84 ml of said solution with 3.84 ml DMSO 10%.

Method

DGAT activity in membrane preparations was assayed in 50 mM Tris-HCl (pH 7.4), 150 mM MgCl$_2$, 1 mM EDTA and 0.2% BSA, containing 50 μM DAG, 32 μg/ml PC/PS and 8.4

μM [$^3$H]-oleoylCoA (at a specific activity of 30 nCi/well) in a final volume of 50 μl in 384-well format using the red shifted Basic Image FlashPlate™ (Perkin Elmer Cat. No. SMP400).

In detail, 10 μl enzyme mix and 10 μl substrate mix were added to 30 μl of assay buffer, optionally in the presence of 1 μl DMSO (blank and controls) or 1 μl of the compound to be tested. This reaction mixture was incubated for 120 minutes at 37° C. and the enzymatic reaction stopped by adding 20 μl of the stop mix. The plates were sealed and the vesicles allowed to settle overnight at room temperature. Plates were centrifuged for 5 minutes at 1500 rpm and measured in Leadseeker.

Experiments with different concentrations of the test compound were performed and curves were calculated and drawn based on % CTRL. (% of normalized control). % CTRL$_{min}$ was calculated according to equation 1, $$\% \ CTRL_{min} = (sample - LC)/(HC - LC) \qquad \text{Equation 1:}$$

where HC (high control) refers to the median of radioluminescence value measured in the wells with enzyme and substrate but without test compound, LC (low control) refers to median background radioluminescence value measured in the wells with substrate without enzyme and without test compound, and sample refers to the radioluminescence value measured in the wells with substrate, enzyme and test compound at a particular concentration.

The calculated % CTRL$_{min}$ values form a sigmoidal dose response descending curve and from this curve pIC$_{50}$ values were calculated (−log IC$_{50}$ where IC$_{50}$ represents the concentration at which the test compound gives 50% inhibition of DGAT1 activity). Table 3 shows the pIC$_{50}$ values for the compounds of formula (I).

In order to determine selectivity of the present compounds for DGAT1 compared to DGAT2, the inhibiting activity of the compounds on DGAT2 was also determined in the above assay, slightly modified to obtain optimal assay conditions for DGAT2. The tested compounds did not show inhibiting activity for DGAT2 (Human DGAT2 (NM032564) was cloned and expressed as described in J. Biolog. Chem. 276(42), pp 38870-38876 (2001)).

TABLE 3 pIC$_{50}$ values (IC$_{50}$ values expressed in M)

| Co. No. | pIC$_{50}$ (mean if tested more than once) | Co. No. | pIC$_{50}$ (mean if tested more than once) |
|---|---|---|---|
| 7 | 5.61 | 103 | 5.38 |
| 26 | 5.74 | 79 | 5.74 |
| 25 | 6.13 | 99 | 5.42 |
| 6 | 6.52 | 108 | 5.31 |
| 20 | 5.88 | 95 | 5.45 |
| 3 | 6.30 | 105 | 5.36 |
| 19 | 5.99 | 94 | 5.45 |
| 21 | 5.24 | 116 | 5.04 |
| 17 | 5.17 | 83 | 5.51 |
| 11 | 5.71 | 97 | 5.44 |
| 16 | 5.19 | 96 | 5.45 |
| 14 | 5.46 | 102 | 5.39 |
| 12 | 5.55 | 110 | 5.14 |
| 15 | 5.31 | 77 | 5.86 |
| 18 | 5.05 | 68 | 6.89 |
| 10 | 6.50 | 75 | 5.94 |
| 13 | 5.46 | 49 | 5.73 |
| 2 | 6.96 | 33 | 6.98 |
| 23 | 5.93 | 44 | 6.03 |
| 22 | 6.00 | 48 | 5.76 |
| 4 | 6.39 | 46 | 5.93 |
| 9 | 8.19 | 50 | 5.71 |
| 8 | 7.52 | 39 | 6.40 |
| 1 | 8.05 | 37 | 6.76 |

TABLE 3-continued pIC$_{50}$ values (IC$_{50}$ values expressed in M)

| Co. No. | pIC$_{50}$ (mean if tested more than once) | Co. No. | pIC$_{50}$ (mean if tested more than once) |
|---|---|---|---|
| 27 | 6.92 | 28 | 7.60 |
| 24 | 6.35 | 38 | 6.56 |
| 5 | 6.18 | 51 | 5.52 |
| 45 | 6.03 | 35 | 6.84 |
| 29 | 7.51 | 34 | 6.85 |
| 42 | 6.13 | 63 | 6.12 |
| 47 | 5.77 | 57 | 7.63 |
| 30 | 7.49 | 65 | 5.81 |
| 41 | 6.22 | 59 | 7.13 |
| 32 | 7.08 | 36 | 6.82 |
| 40 | 6.39 | 61 | 6.82 |
| 115 | 5.05 | 62 | 6.47 |
| 70 | 6.74 | 31 | 7.39 |
| 58 | 7.33 | 67 | 7.07 |
| 56 | 7.76 | 112 | 5.10 |
| 53 | 7.91 | 66 | 7.10 |
| 60 | 7.01 | 90 | 5.47 |
| 55 | 7.82 | 85 | 5.50 |
| 64 | 5.92 | 92 | 5.47 |
| 43 | 6.12 | 89 | 5.47 |
| 93 | 5.46 | 78 | 5.79 |
| 74 | 6.02 | 84 | 5.50 |
| 117 | 5.04 | 82 | 5.54 |
| 107 | 5.32 | 81 | 5.58 |
| 80 | 5.69 | 86 | 5.48 |
| 113 | 5.09 | 91 | 5.47 |
| 76 | 5.87 | 106 | 5.33 |
| 73 | 6.04 | 88 | 5.48 |
| 109 | 5.27 | 72 | 6.08 |
| 71 | 6.10 | 101 | 5.39 |
| 98 | 5.43 | 69 | 6.78 |
| 111 | 5.12 | 100 | 5.40 |
| 87 | 5.48 | 104 | 5.37 |
| 54 | 7.88 | 52 | n.d. |
| 114 | 5.07 | | |

B) In Vivo Study for Effect of Test Compound on GLP-1 Plasma Levels

Elevation of GLP-1 Plasma Levels by a DGAT Inhibitor can be Studied as Follows:

Dogs are deprived from food for a period of 22 hours. At time 0, animals are given a liquid meal, containing 18% fat (w/w), by gavage with a stomach tube. The test compound is given orally together with the meal. Afterwards, a postprandial plasma profile is determined for GLP-1. Therefore, blood is collected at predetermined time intervals in ice-cooled Vacutainers EDTA-plasma tubes and GLP-1 levels are measured in the samples taken at 0 hour (just before the meal) and at 0.5, 1, 2, 4, 6, 8 and 24 hours after dosing. Six dogs (3 males and 3 females) are included per dosage group and the plasma GLP-1 profile is compared with their own GLP-1 profile previously determined in the same conditions but without administration of the test compound.

GLP-1 determinations in plasma are performed with a Glucagon-like peptide-1 (active) ELISA kit 96-well plate of LINCO Research.

E. Composition Examples

"Active ingredient" (a.i.) as used throughout these examples relates to a compound of formula (I), including any stereochemically isomeric form thereof, a N-oxide thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

The invention claimed is:

1. A compound of formula

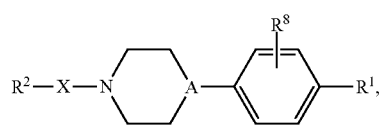

(I)

including any stereochemically isomeric form thereof, wherein

A represents CH;

X represents —NR$^x$—C(=O)—;

R$^x$ represents hydrogen or $C_{1-4}$alkyl;

R$^1$ represents a 5-membered monocyclic heterocycle containing at least 2 heteroatoms each independently selected from O, S, S(=O)p or N; wherein said heterocycle may optionally be substituted with at least one substituent, each substituent independently being selected from the group consisting of hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl—C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)-aminocarbonyl; $C_{1-6}$alkylcarbonyl; nitro; amino; mono-or di($C_{1-6}$alkyl)amino; R$^5$R$^4$N—$C_{1-6}$alkyl; $C_{3-6}$cycloalkyl-NR$^x$—; aryl-NR$^x$—; $C_{3-6}$cycloalkyl-$C_{1-4}$alkyl-NR$^x$—; aryl$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; and aryl-C(=O)—$C_{1-4}$alkyl;

R$^2$ represents R$^3$;

R$^3$ represents phenyl, wherein said phenyl may optionally be substituted with at least one substituent, each substituent independently selected from the group consisting of hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; cyano; $C_{1-6}$alkylcarbonyl; nitro; and amino;

R$^4$ represents hydrogen; $C_{1-4}$alkyl optionally substituted with hydroxyl or $C_{1-4}$alkyloxy; $C_{1-4}$alkyloxy;

R$^5$ represents hydrogen or $C_{1-4}$alkyl;

R$^8$ represents hydrogen; halo; $C_{1-4}$alkyl; or $C_{1-4}$alkyl substituted with hydroxyl;

aryl represents phenyl or phenyl substituted with at least one substituent, each substituent independently being selected from the group consisting of hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; and —S(=O)$_p$—$C_{1-4}$alkyl;

p represents 1 or 2;

a N-oxide thereof, a pharmaceutically acceptable salt thereof or a solvate thereof.

2. The compound as claimed in claim 1 having the following formula

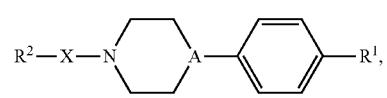

(I)

including any stereochemically isomeric form thereof, wherein

A represents CH;

X represents —NR$^x$—C(=O)—;

R$^1$ represents a 5-membered monocyclic heterocycle containing at least 2 heteroatoms each independently selected from O, S, S(=O)p or N; wherein said heterocycle may optionally be substituted with at least one substituent, each substituent independently being selected from the group consisting of hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl) aminocarbonyl; $C_{1-6}$alkylcarbonyl; nitro; amino; mono- or di($C_{1-6}$alkyl)amino; $C_{3-6}$cycloalkyl-NR$^x$—; aryl-NR$^x$—; $C_{3-6}$cycloalkyl$C_{1-4}$alkyl-NR$^x$—; aryl$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—;

R$^2$ represents R$^3$;

R$^3$ represents phenyl wherein said phenyl may optionally be substituted with at least one substituent, each substituent independently selected from the group consisting of hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; cyano; $C_{1-6}$alkylcarbonyl; nitro; amino;

$R^4$ represents hydrogen; $C_{1-4}$alkyl optionally substituted with hydroxyl or $C_{1-4}$alkyloxy; $C_{1-4}$alkyloxy;

$R^5$ represents hydrogen or $C_{1-4}$alkyl;

aryl represents phenyl or phenyl substituted with at least one substituent, each substituent independently being selected from the group consisting of hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; and —S(=O)$_p$—$C_{1-4}$alkyl;

p represents 1 or 2;

a N-oxide thereof, a pharmaceutically acceptable salt thereof or a solvate thereof.

3. The compound as claimed in claim 1 wherein the compound has the following formula

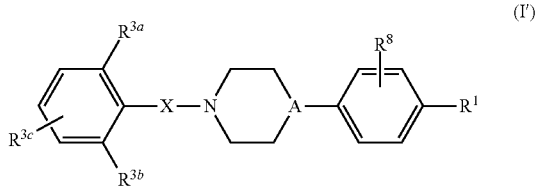

(I')

wherein $R^{3a}$ and $R^{3b}$ each independently represent hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; cyano; $C_{1-6}$alkylcarbonyl; nitro; or amino; and wherein $R^{3c}$ represents hydrogen; hydroxyl; carboxyl; halo;
$C_{1-6}$alkyl; polyhalo$C_{1-6}$alkyl; $C_{1-6}$alkyloxy optionally substituted with $C_{1-4}$alkyloxy;

$C_{1-6}$alkylthio; polyhalo-$C_{1-6}$alkyloxy; cyano; $C_{1-6}$alkylcarbonyl; nitro; or amino.

4. The compound as claimed in claim 1 wherein the compound has the following formula

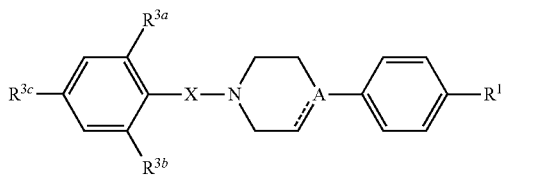

(I")

wherein $R^{3a}$ and $R^{3b}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; cyano; $C_{1-6}$alkylcarbonyl; nitro; or amino; and wherein $R^{3c}$ represents hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; cyano; $C_{1-6}$alkylcarbonyl; nitro; or amino.

5. The compound as claimed in claim 3 wherein $R^{3a}$ and $R^{3b}$ each independently represent halo or $C_{1-6}$alkyl.

6. The compound as claimed in claim 3 wherein both $R^{3a}$ and $R^{3b}$ represent halo.

7. The compound as claimed in claim 1 wherein $R^8$ represents hydrogen.

8. The compound as claimed in claim 1 wherein $R^x$ represents hydrogen; $R^1$ represents a 5-membered monocyclic heterocycle containing at least 2 heteroatoms each independently selected from O, S, S(=O)p or N; wherein said heterocycle may optionally be substituted with one or two substituents, each substituent independently being selected from the group consisting of oxo; $C_{1-6}$alkyl optionally substituted with $C_{1-4}$alkyl-oxycarbonyl; hydroxy$C_{1-6}$alkyl optionally substituted with aryl; mono-or di($C_{1-6}$alkyl)-amino; $R^5R^4N$—$C_{1-6}$alkyl; aryl$C_{1-4}$alkyl-NR$^x$—; $C_{3-6}$cycloalkyl; $C_{3-6}$cyclo-alkyl $C_{1-4}$alkyl; aryl; aryl$C_{1-4}$alkyl; and aryl-C(=O)—$C_{1-4}$alkyl; $R^3$ represents phenyl, wherein said phenyl may optionally be substituted with one or two substituents, each substituent independently selected from the group consisting of hydroxyl; carboxyl; halo; $C_{1-6}$alkyl optionally substituted with hydroxy; polyhalo$C_{1-6}$alkyl; $C_{1-6}$alkyloxy; or $C_{1-6}$alkylthio;

$R^4$ represents hydrogen or $C_{1-4}$alkyl;

$R^5$ represents hydrogen or $C_{1-4}$alkyl; $R^8$ represents hydrogen; aryl represents phenyl or phenyl substituted with at least one substituent, said substituent being selected from the group consisting of halo; $C_{1-6}$alkyl; and $C_{1-6}$alkyloxy.

9. A compound for the treatment of obesity, hypercholesterolemia, hyperlipidemia, dyslipidemia, mixed dyslipidemia, hypertriglyceridemia, fatty liver, nonalcoholic fatty liver disease, liverfibrosis, non-alcoholic steatohepatitis and diabetes, wherein the compound has the following formula

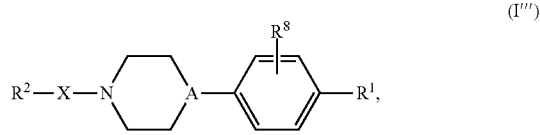

(I''')

including any stereochemically isomeric form thereof, wherein

A represents CH;

X represents —NR$^x$—C(=O)—;

$R^x$ represents hydrogen or $C_{1-4}$alkyl;

$R^1$ represents a 5-membered monocyclic heterocycle containing at least 2 heteroatoms each independently selected from O, S, S(=O)p or N; wherein said heterocycle may optionally be substituted with at least one substituent, each substituent independently being selected from the group consisting of hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)-aminocarbonyl; $C_{1-6}$alkylcarbonyl; amino; mono-or di($C_{1-6}$alkyl)amino; $R^5R^4N$—$C_{1-6}$alkyl; $C_{3-6}$cycloalkyl-NR$^x$—; aryl-NR$^x$—; $C_{3-6}$cycloalkyl-$C_{1-4}$alkyl-NR$^x$—; aryl$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C (=O)—; aryl; aryloxy; arylC$_{1-4}$alkyl; aryl-C(=O)—; and aryl-C(=O)—C$_{1-4}$alkyl;

R$^2$ represents R$^3$;

R$^3$ represents phenyl wherein said phenyl may optionally be substituted with at least one substituent, each substituent independently selected from the group consisting of hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; cyano; C$_{1-6}$alkylcarbonyl; nitro; and amino;

R$^4$ represents hydrogen; C$_{1-4}$alkyl optionally substituted with hydroxyl or C$_{1-4}$alkyloxy; C$_{1-4}$alkyloxy;

R$^5$ represents hydrogen or C$_{1-4}$alkyl;

R$^8$ represents hydrogen; halo; C$_{1-4}$alkyl; or C$_{1-4}$alkyl substituted with hydroxyl;

aryl represents phenyl or phenyl substituted with at least one substituent, each substituent independently being selected from the group consisting of hydroxyl; carboxyl; halo; C$_{1-6}$alkyl optionally substituted with C$_{1-4}$alkyloxy, amino or mono-or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono-or di(C$_{1-4}$alkyl)aminocarbonyl; C$_{1-6}$alkylcarbonyl; nitro; amino; mono- or di(C$_{1-4}$alkyl)amino; and —S(=O)$_p$—C$_{1-4}$alkyl;

p represents 1 or 2;

a N-oxide thereof, a pharmaceutically acceptable salt thereof or a solvate thereof.

10. A pharmaceutical composition comprising a pharmaceutically acceptable carrier, and as active ingredient a therapeutically effective amount of a compound as claimed in claim 1.

* * * * *